US009726659B2

(12) United States Patent
Wheeler et al.

(10) Patent No.: US 9,726,659 B2
(45) Date of Patent: Aug. 8, 2017

(54) CMPF AS A BIOMARKER FOR DIABETES AND ASSOCIATED METHODS

(71) Applicant: The Governing Council of the University of Toronto, Toronto (CA)

(72) Inventors: Michael Wheeler, Toronto (CA); Kacey Prentice, Toronto (CA); Feihan Dai, Toronto (CA); Ravi Retnakaran, Toronto (CA)

(73) Assignee: The Governing Council of the University of Toronto, Toronto, ON (CA)

( * ) Notice: Subject to any disclaimer, the term of this patent is extended or adjusted under 35 U.S.C. 154(b) by 0 days.

(21) Appl. No.: 14/429,977

(22) PCT Filed: Sep. 20, 2013

(86) PCT No.: PCT/CA2013/000798
§ 371 (c)(1),
(2) Date: Mar. 20, 2015

(87) PCT Pub. No.: WO2014/043793
PCT Pub. Date: Mar. 27, 2014

(65) Prior Publication Data
US 2015/0247839 A1 Sep. 3, 2015

Related U.S. Application Data

(60) Provisional application No. 61/703,867, filed on Sep. 21, 2012, provisional application No. 61/787,718, filed on Mar. 15, 2013.

(51) Int. Cl.
| | |
|---|---|
| G01N 33/50 | (2006.01) |
| A61K 31/198 | (2006.01) |
| A61K 31/43 | (2006.01) |
| C07D 307/68 | (2006.01) |
| A61K 31/195 | (2006.01) |
| A61K 31/196 | (2006.01) |
| A61K 38/17 | (2006.01) |
| G01N 33/53 | (2006.01) |
| G01N 30/88 | (2006.01) |

(52) U.S. Cl.
CPC ....... *G01N 33/5005* (2013.01); *A61K 31/195* (2013.01); *A61K 31/196* (2013.01); *A61K 31/198* (2013.01); *A61K 31/43* (2013.01); *A61K 38/177* (2013.01); *C07D 307/68* (2013.01); *G01N 33/507* (2013.01); *G01N 33/5023* (2013.01); *G01N 33/5308* (2013.01); *G01N 2030/8822* (2013.01); *G01N 2800/042* (2013.01); *G01N 2800/50* (2013.01); *G01N 2800/52* (2013.01); *Y10T 436/142222* (2015.01)

(58) Field of Classification Search
None
See application file for complete search history.

(56) References Cited

U.S. PATENT DOCUMENTS

2010/0096329 A1* 4/2010 Kotanko .......... A61M 1/16
210/638

FOREIGN PATENT DOCUMENTS

| WO | 2009/059150 | 5/2009 |
| WO | 2010/045180 | 4/2010 |
| WO | 2011/146683 | 11/2011 |
| WO | 2012/015904 | 2/2012 |
| WO | 2013/059234 | 4/2013 |
| WO | 2013/086365 | 6/2013 |

OTHER PUBLICATIONS

Boden et al. (Exp. Clin. Endocrinol. Diabetes, 111 (2003), pp. 121-124).*
Arkhammar, P., et al., "Glucose-stimulated efflux of FURA-2 in pancreatic beta-cells is prevented by probenecid." Biochemical and Biophysical Research Communications. 1989. 159(1): p. 223-228.
Basford, C.L., et al., "The functional and molecular characterisation of human embryonic stem cell-derived insulin-positive cells compared with adult pancreatic beta cells." Diabetologia, 2012. 55(2): p. 358-71.
Baudoux, T.E.R., et al., "Probenecid prevents acute tubular necrosis in a mouse model of aristolochic acid hephropathy." Kidney International. 2012. 82(10).
Boucher, M.J., et al., "Phosphorylation marks IPF1/PDX1 protein for degradation by glycogen synthase kinase 3-dependent mechanisms." J Biol Chem, 2006. 281(10): p. 6395-403.
Bowes, S.B., et al., "Measurement of glucose metabolism and insulin secretion during normal pregnancy and pregnancy complicated by gestational diabetes." Diabetologia, 1996. 39(8): p. 976-83.
Buchanan, T.A., "Pancreatic B-cell defects in gestational diabetes: implications for the pathogenesis and prevention of type 2 diabetes." J Clin Endocrinol Metab, 2001. 86(3): p. 989-93.
Butler, D., "Wartime tactic doubles power of scarce bird-flu drug." Nature, 2005. 438(7064): p. 6.
Costigan, M.G. and Lindup, W.E., "Plasma clearance in the rat of a furan dicarboxylic acid which accumulates in uremia." Kidney Int, 1996. 49(3): p. 634-8.

(Continued)

*Primary Examiner* — Kortney L Klinkel
*Assistant Examiner* — William Lee
(74) *Attorney, Agent, or Firm* — Bereskin & Parr LLP/S.E.N.C.R.L., s.r.l.; I. Laurence MacPhie

(57) ABSTRACT

Provided are methods for identifying or monitoring a subject having, or at risk of developing, impaired glucose homeostasis. Carboxy-4-methyl-5-propyl-2-furanpropanoic acid (CMPF) is shown to be a biomarker for impaired glucose homeostasis and/or conditions characterized by β-cell dysfunction. Comparing a test level of CMPF in a subject to a control level identifies subjects having, or at risk of developing, impaired glucose homeostasis. Also provided are methods of causing impaired glucose homeostasis or β-cell dysfunction and methods of screening for compounds that affect the activity of β-cells. Also provided are methods for the treatment of β-cell dysfunction by reducing the physiological levels of CMPF in a subject as well as the use of a OAT modulator for the treatment of β-cell dysfunction.

14 Claims, 39 Drawing Sheets

(56) References Cited

OTHER PUBLICATIONS

Deguchi, T., et al., "Characterization of uremic toxin transport by organic anion transporters in the kidney." Kidney Int, 2004. 65(1): p. 162-74.
Deguchi T., et al., "Renal clearance of endogenous hippurate correlates with expression levels of renal organic anion transporters in uremic rats." J Pharmacol Exp Ther, 2005. 314(2): p. 932-8. (A).
Deguchi,T.,et al., "Differential contributions of rOat1 (Slc22a6) and rOat3 (Slc22a8) to the in vivo renal uptake of uremic toxins in rats." Pharm Res, 2005. 22(4): p. 619-27. (B).
Deguchi, T., et al., "Involvement of organic anion transporters in the efflux of uremic toxins across the blood-brain baffier." J Neurochem, 2006. 96(4): p. 1051-9.
Diao, J., et al., "UCP2 is highly expressed in pancreatic alpha-cells and influences secretion and survival." Proc Natl okcad Sci U S A, 2008. 105(33): p. 12057-62.
Dominguez, V., et al., "Class II phosphoinositide 3—kinase regulates exocytosis of insulin granules in pancreatic beta cells." J Biol Chem, 2011. 286(6): p. 4216-25.
Elks, M.L., "Chronic perifusion of rat islets with palmitate suppresses glucose-stimulated insulin release." Endocrinology, 1993. 133(1): p. 208-14.
Everts, et al., "Effects of a furan fatty acid and indoxyl sulfate on thyroid hormone uptake in cultured anterior pituitary cells." Am J Physiol 1995;268:E974-E979.
Hue, L. and Taegtmeyer, H. "The Randle cycle revisited: a new head for an old hat." Am J Physiol Endocrinol Metab, 2009. 297(3): p. E578-91.
Humphrey, R.K., et al., "Glucose regulates steady-state levels of PDX1 via the reciprocal actions of GSK3 and AKT kinases." J Biol Chem, 2010.285(5): p. 3406-16.
Joseph, J.W., et al., "Free fatty acid-induced beta-cell defects are dependent on uncoupling protein 2 expression." J Biol Chem, 2004. 279(49): p. 51049-56.
Kahn, S.E., "The relative contributions of insulin resistance and beta-cell dysfunction to the pathophysiology of Type 2 diabetes." Diabetologia, 2003. 46(1): p. 3-19.
Kamoda, T., et al., "The serum levels of proinsulin and their relationship with IGFBP-1 in obese children." Diabetes Obes Metab, 2006. 8(2): p. 192-6.
Kashemsant, N. and Chan, C.B., "Impact of uncoupling protein-2 overexpression on proinsulin processing." J Mol Endocrinol, 2006. 37(3): p. 517-26.
Kawamori, D., et al., "Oxidative stress induces nucleo-cytoplasmic translocation of pancreatic transcription factor PDX-1 through activation of c-Jun NH(2)-terminal kinase." Diabetes, 2003. 52(12): p. 2896-904.
Kawamori, D., et al., "The forkhead transcription factor Foxo1 bridges the JNK pathway and the transcription factor PDX-1 through its intracellular translocation." J Biol Chem, 2006. 281(2): p. 1091-8.
Kuhl, C., "Insulin secretion and insulin resistance in pregnancy and GDM. Implications for diagnosis and management." Diabetes, 1991, 40 Suppl 2: p. 18-24.
Kutlu, B., et al., "Detailed transcriptome atlas of the pancreatic beta cell." BMC Med Genomics, 2009. 2: p. 3.
Lee, S.C., et al., "Uncoupling protein 2 regulates reactive oxygen species formation in islets and influences susceptibility to diabetogenic action of streptozotocin." J Endocrinol, 2009. 203(1): p. 33-43.
Lee, E., et al., "Antioxidant treatment may protect pancreatic beta cells through the attenuation of islet fibrosis in an animal model of type 2 diabetes." Biochem Biophys Res Commun, 2011. 414(2): p. 397-402.
Lim, C.F., et al., "A naturally occurring furan fatty acid enhances drug inhibition of thyroxine binding in serum." Metabolism (1993). 42(11); p. 1468-74.
Liu, Y., et al., "Adiponectin Corrects High-Fat Diet-Induced Disturbances in Muscle Metabolomic Profile and Whole-Body Glucose Homeostasis." Diabetes, Mar. 2013, vol. 62, No. 3, p. 743-752.

Mabuchi, H, and Nakahashi, H. "A major endogenous ligand substance involved in renal failure." Nephron (1988). 49(4); 277-80.
Mason, R.M., "Studies on the effect of probenecid (benemid) in gout." Ann Rheum Dis, 1954. 13(2): p. 120-30.
Mishra, R., et al., "Adipose differentiation—related protein and regulators of lipid homeostasis identified by gene expression profiling in the murine db/db diabetic kidney." Am J Physiol Renal Physiol, 2004. 286(5): p. F913-21.
Miyamoto, Y., et al., "A uremic toxin, 3-carboxy-4-methyl-5-propyl-2-furanpropionate induces cell damage to proximal tubular cells via the generation of a radical intermediate." Biochem Pharmacol, 2012. 84(9): p. 1207-14.
More, V.R., et al., "Severe diabetes and leptin resistance cause differential hepatic and renal transporter expression in mice." Comp Hepatol, 2012. 11(1): p. 1.
Poitout, V. and Robertson, R.P., "Glucolipotoxicity: fuel excess and beta-cell dysfunction." Endocr Rev, 2008. 29(3): p. 351-66.
Niwa, T., et al., "Inhibition of mitochondrial respiration by furancarboxylic acid accululated in uremic serum in its albumin-bound and non-diabyzable form." Clin Nephrol (1993). 39(2); 92-96.
Prentki, M. and Nolan, C.J., "Islet beta cell failure in type 2 diabetes." J Clin Invest, 2006. 116(7): p. 1802-12.
Retnakaran, R., et al., "Beta-cell function declines within the first year postpartum in women with recent glucose intolerance in pregnancy." Diabetes Care, 2010. 33(8): p. 1798-804.
Robertson, R.P., "Chronic oxidative stress as a central mechanism for glucose toxicity in pancreatic islet beta cells in diabetes." J Biol Chem, 2004. 279(41): p. 42351-4.
Robson-Doucette, C.A., et al., "Beta-cell uncoupling protein 2 regulates reactive oxygen species production, which influences both insulin and glucagon secretion." Diabetes, 2011. 60(11): p. 2710-9.
Saadeh, M., et al., "Reactive oxygen species stimulate insulin secretion in rat pancreatic islets: studies using mono-oleoyl-glycerol." PLoS One, 2012. 7(1): p. e30200.
Sassa, T., et al., "Measurement of furancarboxylic acid, a candidate for uremic toxin, in human serum, hair, and sweat, and analysis of pharmacological actions in vitro." Arch Toxicol Feb. 2000; 73(12) :649-54.
Sato, M., et al., "Reduced renal clearance of furancarboxylic acid, a major albumin-bound organic acid, in undialyzed uremic patients." Nephron (1996). 74(2); 419-21.
Sekine, T., et al. "Molecular physiology of renal organic anion transporters." Am J Physiol Renal Physiol, 2006. 290(2): p. F251-61.
Sweet, D.H., et al., "Impaired organic anion transport in kidney and choroid plexus of organic anion transporter 3 (Oat3 (Slc22a8)) knockout mice." J Biol Chem, 2002. 277(30): p. 26934-43.
Tsutsumi, Y., et al., "Interaction between two dicarboxylate endogenous substances, bilirubin and an uremic toxin, 3-carboxy-4-methyl-5-propyl-2-furanpropanoic acid, on human serum albumin." Pharmaceutical Research (1999). 16(6); 916.
Wijendran, V., et al., "Maternal plasma phospholipid polyunsaturated fatty acids in pregnancy with and without gestational diabetes mellitus: relations with maternal factors." Am J Clin Nutr, 1999. 70(1): p. 53-61.
International Search Report (completed on Nov. 21, 2013) and Written Opinion (completed on Nov. 28, 2013) for corresponding PCT Application No. PCT/CA2013/000798.
Prentice, K.J., et al., "The furan fatty acid metabolite CMPF is elevated in diabetes and induces β cell dysfunction." Cell Metab, Apr. 1, 2014;19(4): p. 653-66.
Steller, F., et al., "3-Hydroxyglutaric acid is transported via the sodium-dependent dicarboxylate transporter NaDC3." J Mol Med (Berl), Jul. 2007;85(7): p. 763-70.
Schulze, M.B., et al., "Biomarkers and risk prediction of type 2 diabetes; Biomarker und RisikoprA diktion des Typ-2-Diabetes." Der Diabetologe, Springer, Berlin, DE, vol. 8, No. 1, Jan. 15, 2012, pp. 18-25.
Simon, M.-C., et al., "Biomarkers and type 1 diabetes; Biomarker und Typ-1-Diabetes." Der Diabetologe, Springer, Berlin, DE, vol. 8, No. 1, Jan. 27, 2012, pp. 11-17.

(56) References Cited

OTHER PUBLICATIONS

Extended European Search Report completed Mar. 8, 2016 for corresponding European Patent Application No. 13839563.7.

* cited by examiner

| Formal Name | 3-carboxy-4-methyl-5-propyl-2-furanpropanoic acid |
|---|---|
| Molecular Formula | $C_{12}H_{16}O_5$ |
| Formula Weight | 240.3 |
| Formulation | A crystalline solid |
| $\lambda_{max}$ | 260 nm |

CMPF AS A BIOMARKER FOR DIABETES AND ASSOCIATED METHODS

CROSS REFERENCE TO RELATED APPLICATIONS

This application is a national phase entry of PCT/CA2013/000798 filed Sep. 20, 2013 (which designates the U.S.) which claims priority to U.S. Provisional Patent Application No. 61/703,867 filed on Sep. 21, 2012 (now abandoned), and U.S. Provisional Patent Application No. 61/787,718 filed on Mar. 15, 2013 (now abandoned), the contents of which are both hereby incorporated by reference in their entirety.

FIELD

The present invention relates to the field of diabetes and more specifically to 3-carboxy-4-methyl-5-propyl-2-furanpropanoic acid (CMPF) as a biomarker for subjects having, or at risk of developing, impaired glucose homeostasis and/or diabetes.

INTRODUCTION

Rising obesity rates, increasingly sedentary lifestyles and an aging population continue to drive dramatic increases in the prevalence of type 2 diabetes (T2D). An estimated 260 million people worldwide are affected by T2D, with millions more living with pre-diabetes, a condition of impaired glucose tolerance (IGT) which puts an individual at higher risk of developing T2D, and a further 7 million people being newly diagnosed annually. While obesity and insulin resistance contribute to the development of T2D, it is ultimately the inability of the $\beta$ cell to respond to changing metabolic demands that leads to the development of the disease.

Importantly, the occurrence of another form of diabetes, Gestational Diabetes Mellitus (GDM) is also increasing. GDM currently afflicts 3-14% of pregnant women and is a condition in which women with no previous history of diabetes exhibit IGT during late pregnancy when there is severe insulin resistance. This severe acquired insulin resistance provides a significant physiological stress on $\beta$ cell compensatory capacity, similar to that observed in T2D, wherein appropriate adaptation results in normal glucose tolerance (NGT), indicative of a low risk of future T2D, and insufficient $\beta$ cell compensation leads to GDM, which identifies a very high risk of future development of T2D (~20-50% within 5 years).

Current diagnostic tests for T2D rely on direct and indirect measurements of blood glucose levels. Measurements of glycated hemoglobin (HbA1c) are indirectly indicative of the average blood sugar levels over the previous 2-3 months, with >6.5% of hemoglobin being glycated indicating high average blood glucose and thus T2D. More direct methods include random or fasted blood glucose tests, or an oral glucose tolerance test (OGTT), as is used in the diagnosis of GDM, which directly measures one's ability to clear glucose from the blood in a set period of time following ingestion.

There remains a need for new and improved methods for identifying and/or monitoring subjects with impaired glucose homeostasis and/or diabetes.

SUMMARY

In one aspect of the disclosure, CMPF has been identified as a biomarker for impaired glucose homeostasis and/or diabetes. In one embodiment, CMPF is a biomarker for type II diabetes. CMPF has also been identified as a biomarker for conditions characterized by impaired glucose homeostasis such as, but not limited to gestational diabetes mellitus and impaired glucose tolerance. CMPF has also been shown to be increased in subjects with type II diabetes relative to normal controls. High levels of CMPF have also been shown to impair $\beta$-cell function and prevent glucose stimulated insulin secretion in vitro and in vivo.

In one embodiment there is provided a method of identifying a subject having, or at risk of developing, impaired glucose homeostasis comprising:
(a) determining a test level of 3-carboxy-4-methyl-5-propyl-2-furanpropanoic acid (CMPF) in a sample from a subject; and
(b) comparing the test level of CMPF to a control level wherein a difference or similarity in the test level of CMPF relative to the control level is indicative of the subject having, or at risk of developing, impaired glucose homeostasis.

In one embodiment, the control level is representative of a level of CMPF in subjects without impaired glucose homeostasis and an increased test level of CMPF relative to the control is indicative of the subject having, or at risk of developing impaired glucose homeostasis. In one embodiment, the control level is representative of a level of CMPF in subjects with impaired glucose homeostasis and a similar or greater test level of CMPF relative to the control is indicative of the subject having, or at risk of developing impaired glucose homeostasis. Optionally, the method further comprises treating a subject identified as having, or at risk of developing, impaired glucose homeostasis. For example, in one embodiment, a subject identified as having impaired glucose homeostasis is treated with a CMPF inhibitor. In one embodiment, the subject is treated with insulin. In one embodiment, the subject is treated with metformin, GLP-1 receptor agonists, GLP-1 analogs, sulfonylureas or an insulin sensitizer. In some embodiments, treating a subject comprises administering to the subject an agent suitable for the treatment of impaired glucose homeostasis such as a CMPF inhibitor, insulin, metformin, GLP-1 receptor agonists, GLP-1 analogs, sulfonylureas, or insulin sensitizers etc.

In another embodiment, there is provided a method of monitoring a subject having impaired glucose homeostasis comprising:
(a) determining a test level of 3-carboxy-4-methyl-5-propyl-2-furanpropanoic acid (CMPF) in a sample from the subject; and
(b) comparing the test level of CMPF to a level of CMPF from the subject at an earlier time point, wherein an increase in the level of CMPF is indicative of more severe impaired glucose homeostasis in the subject or a decrease in the level of CMPF is indicative of improved glucose homeostasis in the subject.

In one embodiment, the methods described herein for identifying or monitoring a subject having impaired glucose homeostasis include obtaining or providing a sample from the subject prior to determining a test level of CMPF. In one embodiment a subject having, or at risk of developing, impaired glucose homeostasis has, or is at risk of developing a condition characterized by $\beta$-cell dysfunction. In one embodiment, the condition characterized by $\beta$-cell dysfunction is impaired glucose tolerance, pre-diabetes, gestational diabetes mellitus, insulin resistance or type 2 diabetes. Optionally, the step of determining the test level of CMPF in the sample comprises detecting CMPF in the sample. For example, in one embodiment CMPF is detected in the sample using mass spectrometry, spectroscopy or immunohistochemistry. In one embodiment, CMPF is detecting using an antibody specific for CMPF, such as in an enzyme-linked immunosorbent assay. In one embodiment, CMPF is detected using gas chromatography/mass spectrometry (GC-MS) or liquid chromatography mass spectrometry (LC-MS).

In another embodiment, there is provided a method of causing β-cell dysfunction in one or more β-cells comprising contacting the one or more β-cells with CMPF. Optionally, the β-cells are in vivo, in vitro or ex vivo. In one embodiment, contacting the β-cells with CMPF causes impaired insulin secretion. In one embodiment, the method comprises contacting the cells with a concentration of CMPF greater than 20 µM, 50 µM, 100 µM, 150 µM, 200 µM, 300 µM or 500 µM. Optionally, the β-cells are in a subject in vivo and the method comprises administering CMPF to the subject. In one embodiment, the subject is an animal such as a mouse or rat. Optionally, the methods described herein of causing β-cell dysfunction are useful for generating in vitro or in vivo models of β-cell dysfunction. In some embodiments, such models are useful for screening test agents to identify candidates useful for treating conditions associated with impaired glucose homeostasis or β-cell dysfunction.

In one embodiment, there is provided a method of screening for agents that affect the activity of β-cells comprising:
(a) providing one or more β-cells wherein the activity of the β-cells has been reduced by contacting the β-cells with 3-carboxy-4-methyl-5-propyl-2-furanpropanoic acid (CMPF);
(b) contacting the β-cells with a test agent; and
(c) determining the effect of the test agent on the activity of the β-cells.

In one embodiment, the method further comprises identifying the test agent as effective if its effect on the activity of the β-cells is above a threshold level. In one embodiment, the activity is insulin secretion. In one embodiment, the activity is insulin exocytosis. In one embodiment, the activity is glucose stimulated insulin secretion (GSIS). In one embodiment, the activity is fatty acid or amino acid stimulated insulin secretion. In one embodiment, the activity is insulin secretion as regulated by the incretin hormones. In one embodiment, the activity is the transcription or translation of genes that control insulin biosynthesis and/or secretion (exocytosis), insulin-regulating genes or glucose-sensing genes. In one embodiment, the activity is the transcription or translation of one or more genes that directly or indirectly affect insulin transcription, insulin translation, insulin biosynthesis and/or secretion (exocytosis), insulin-regulating genes or glucose-sensing genes. In one embodiment, the one or more genes are selected from SLC2A1, SLC2A2, GCK, Kir6.2, ABCC8, CACNA1D, CACNA1A, CACNA1H, KCNB1, SNAP25, STX1A, VAMP2, SYN1A, PDX1, MAFA, NKX6.1, INS (in mice INS1 or INS2), PCSK1, PCSK2 and CPE. In one embodiment, the activity is β-cell mass expansion or β-cell loss. Optionally, test agents that affect the activity of β-cells are identified as candidates useful for the treatment of a condition characterized by β-cell dysfunction.

In another embodiment, there is provided a method of treating β-cell dysfunction in a subject in need thereof, comprising administering to the subject a 3-carboxy-4-methyl-5-propyl-2-furanpropanoic acid (CMPF) inhibitor. In one embodiment, there is also provided the use of a CMPF inhibitor for the treatment of β-cell dysfunction in a subject in need thereof. In one embodiment, there is also provided a CMPF inhibitor for use in the treatment of β-cell dysfunction in a subject in need thereof. Also provided is the use of a CMPF inhibitor in the manufacture of a medicament for the treatment of β-cell dysfunction. Optionally, the subject has, or is suspected of having, impaired glucose homeostasis, impaired glucose tolerance, pre-diabetes, insulin resistance, gestational diabetes mellitus or type 2 diabetes. In one embodiment, the CMPF inhibitor is an OAT inhibitor. In one embodiment, the CMPF inhibitor is an OAT activator.

In one embodiment, the CMPF inhibitor lowers the physiological concentration of CMPF in the blood. In one embodiment, the CMPF inhibitor lowers the physiological concentration of CMPF in pancreatic islet cells. In one embodiment, the CMPF inhibitor lowers the physiological concentration of CMPF in insulin producing cells such as β-cells. In one embodiment, the CMPF inhibitor is an OAT modulator. In one embodiment, the OAT modulator is an inhibitor of OAT1, OAT3 and/or OAT4. Examples of OAT-specific inhibitors include, but are not limited to probenecid, p-aminohippurate (PAH), pravastatin, novobiocin, sulfinpyrazone, and benzylpenicillin/Penicillin G (PCG), cilastatin and KW-3902. In one embodiment, the OAT inhibitor is a non-specific OAT inhibitor such as probenecid. In one embodiment, the OAT inhibitor is specific for OAT1 such as PAH. In one embodiment, the OAT inhibitor is specific for OAT3 such as PCG or Pravastatin.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF VARIOUS EMBODIMENTS

Figure 1:
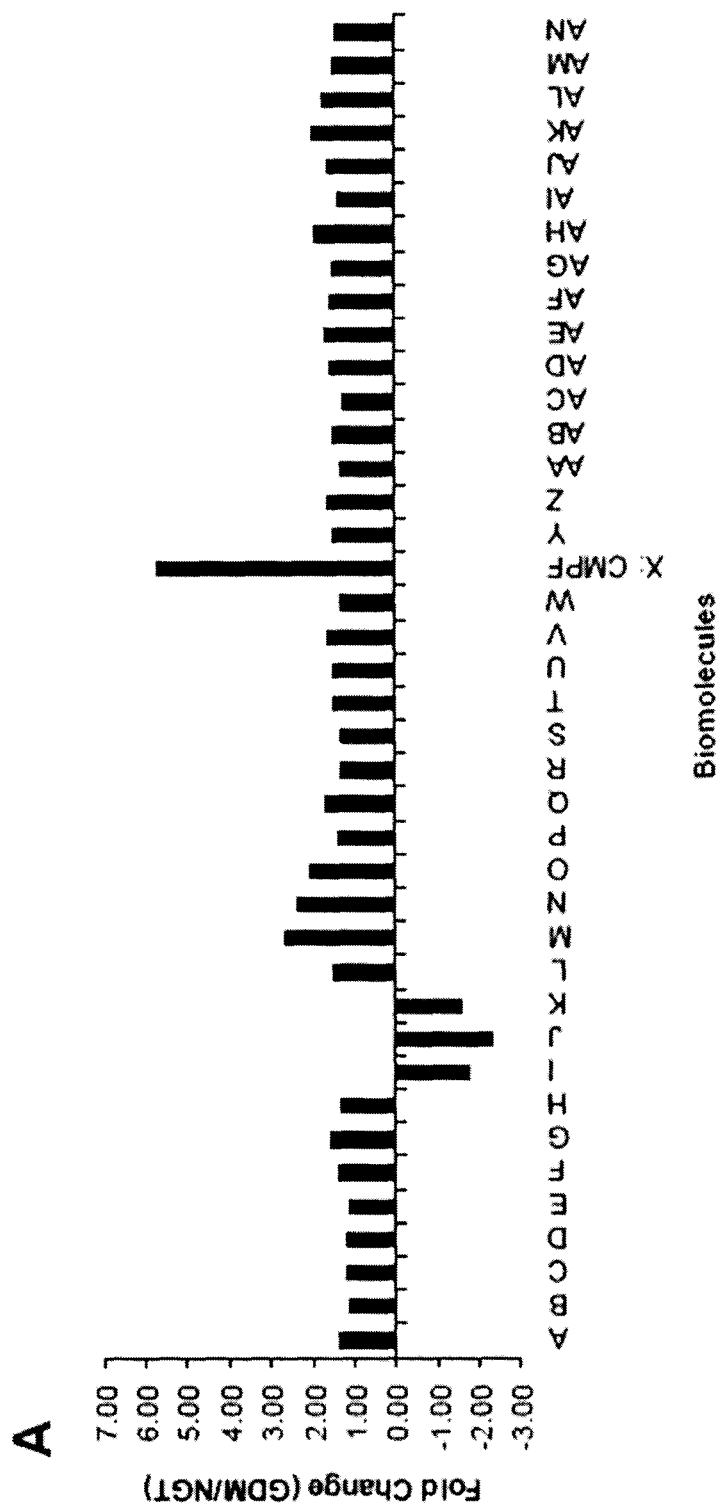
FIG. 1. A) Histogram showing fold change in biomolecules significantly changed in GDM vs. NGT patient plasma based on metabolomic profiling. CMPF is the most highly upregulated with a 5.69 fold increase in GDM vs. NGT. B) Results of two independent metabolomic screens on unique cohorts showing a similar fold increase in CMPF in GDM compared to NGT patients. First run in black, second run in white, average of two runs in grey. GDM values are all significantly elevated compared to respective NGT populations, *P<0.01.
Figure 1:
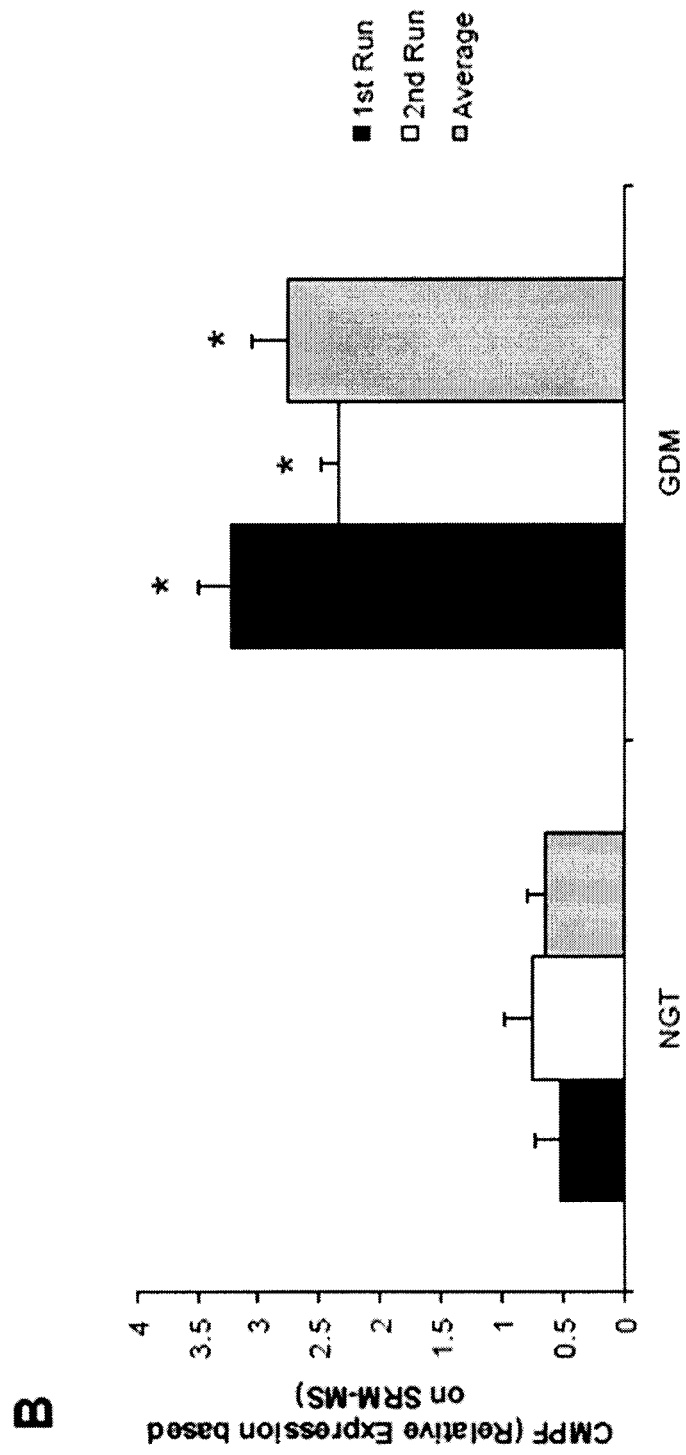

In one aspect of the description, 3-carboxy-4-methyl-5-propyl-2-furanpropanoic acid (CMPF) has been shown to be a biomarker useful for identifying subjects having, or at risk of developing, impaired glucose homeostasis. As set out in Example 1, levels of the furan fatty acid CMPF were found to be elevated in subjects with gestational diabetes mellitus (GDM) compared to subjects with normal glucose tolerance. Women who developed impaired glucose tolerance within 1 year post-partum following GDM were also found to have particularly elevated levels of CMPF compared to women who maintained normal glucose tolerance over the same time period. In another aspect of the disclosure, high physiologically relevant levels of CMPF have been shown to impair insulin secretion in vitro. Furthermore, injections of CMPF have been shown to impair β-cell function and prevent glucose stimulated insulin secretion in vivo. CMPF therefore impairs glucose disposal as measured by a glucose tolerance test and is associated with the pathogenesis of impaired glucose homeostasis and conditions characterized by β-cell dysfunction such as GDM, impaired insulin secretion, glucose intolerance and type II diabetes. The use of a CMPF inhibitor such as probenecid has been shown to abolish the effect of CMPF on glucose-stimulated insulin secretion. Remarkably, the administration of probenecid has also been shown to elevate circulating CMPF levels in vivo without altering glucose tolerance. CMPF inhibitors that reduce the physiological levels of CMPF in the blood and/or pancreatic islets cells are therefore expected to be useful for the treatment of β-cell dysfunction, such as in subjects with impaired glucose homeostasis.

The present description therefore provides methods for identifying subjects having, or at risk of developing, impaired glucose homeostasis as well as methods for monitoring subjects with impaired glucose homeostasis. Optionally, subjects having or at risk of developing impaired glucose homeostasis have β-cell dysfunction or a condition characterized by β-cell dysfunction. Optionally, the methods described herein are useful for identifying or monitoring subjects with impaired glucose homeostasis who do not have β-cell dysfunction.

Also provided are methods for causing β-cell dysfunction by contacting one or more cells with CMPF. Methods for causing β-cell dysfunction are useful for generating in vitro or in vivo models of impaired glucose homeostasis and conditions characterized by β-cell dysfunction. The present disclosure also provides methods of screening for compounds that affect the activity of β-cells. Also provided are methods for the treatment of β-cell dysfunction or a condition characterized by β-cell dysfunction comprising administering to the subject a CMPF inhibitor, or the use of a CMPF inhibitor for the treatment of β-cell dysfunction or a condition characterized by β-cell dysfunction. In one embodiment, the CMPF inhibitor is an OAT activator and treatment with the OAT activator helps reduce the levels of CMPF in the blood. Optionally, the CMPF inhibitor is an OAT inhibitor such as probenecid, p-aminohippurate (PAH) or benzylpenicillin (PCG), or combinations thereof. In one embodiment, treatment with an OAT inhibitor helps reduce the levels of CMPF in pancreatic islet cells.

Definitions

As used herein, "impaired glucose homeostasis" refers to a transient or persistent condition wherein a subject is unable to maintain normal levels of glucose in the blood. Examples of impaired glucose homeostasis include, but are not limited to, impaired insulin secretion, impaired glucose tolerance, pre-diabetes, gestational diabetes mellitus, insulin resistance or type 2 diabetes. Optionally, subjects with impaired glucose homeostasis also have β-cell dysfunction.

As used herein, the term "β-cell dysfunction" refers to a condition wherein the viability or physiological activity of β-cells is impaired. In one embodiment, β-cell dysfunction refers to the inability of beta cells to secrete sufficient bioactive insulin to maintain normal levels of glucose, fatty acids and other nutrients in the blood and tissues. In one embodiment, β-cell dysfunction refers to inappropriately exaggerated insulin secretion by β-cells that contributes to the development of insulin resistance β-cell dysfunction is optionally a condition of one or more cells in vitro, ex vivo, or in vivo. Examples of β-cell dysfunction include, but are not limited to, impaired insulin secretion, impaired glucose tolerance, pre-diabetes, gestational diabetes mellitus, insulin resistance or type 2 diabetes.

As used herein, the term "subject" refers to any member of the animal kingdom that has β-cells which store and release insulin in order to control levels of glucose in the blood. In one embodiment, the subject is a human. In one embodiment, the subject has, or is suspected of having, a condition characterized by β-cell dysfunction. In one embodiment, the subject is an animal such as a rat or mouse.

The term "sample" refers to any fluid or other specimen from a subject which can be assayed for CMPF. For example, in one embodiment, the sample is blood or a blood derivative such as serum or plasma. Optionally, the sample is plasma in the form of EDTA (sodium, K2 or K3) or heparin. In one embodiment, the sample is urine or sweat. In one embodiment, levels of CMPF are determined in a test sample from a subject. Optionally, the test sample may be a frozen or archived sample.

The term "control level" as used herein refers to a level of CMPF in sample from a subject or a group of subjects who are either known as having a particular condition or as not having a particular condition. The control can vary depending on what is being monitored, assessed or identified. For example, in one embodiment a difference or similarity in the test level of CMPF relative to the control level is indicative of the subject having, or at risk of developing, impaired glucose homeostasis. In one embodiment a difference or similarity in the test level of CMPF relative to the control level is indicative of the subject having, or at risk of developing, the condition characterized by β-cell dysfunction. The control can also be a predetermined standard, average or reference range of values. Optionally, the term "control level" includes a level of CMPF in a test sample from a subject determined at an earlier time point. In one embodiment, the control is an age or sex-matched control. In some embodiments, the control level is indicative of a subject without impaired glucose homeostasis, optionally about 20 μM. In some embodiments, the control level is indicative of a subject with impaired glucose homeostasis, optionally about 50 μM, 100 μM, 150 μM or 200 μM. In some embodiments, a level of CMPF greater than the control level indicates that a subject has, or is at risk of developing, impaired glucose homeostasis.

As used herein "agent" refers to a molecule, compound or substance of determined or undetermined composition including but not limited to organic or inorganic molecules, polypeptides, antibodies, polysaccharides or other biomolecules or an extract made from biological materials such as bacteria, plants, fungi, or animal cells or tissues. Optionally the agent is a molecule, compound or substance in an array such as a combinatorial small molecule array or display library. In one embodiment, the agent is an organic compound such as probenecid, p-aminohippurate (PAH) or benzylpenicillin (PCG).

As used herein, "activity of β-cells" refers to any changes in the size, viability or physiological activity of β-cells that impacts the sensing of nutrients or the synthesis, storage or release of insulin. Examples of the activity of β-cells include, but are not limited to glucose stimulated insulin secretion, transcription or translation of insulin genes or glucose-sensing genes, a change in the number of β-cells or an expansion, depletion or failure in expansion in β-cell mass. Optionally, the methods described herein include determining the effect of a test agent on a single activity or two or more activities of one or more β-cells.

As used herein, the term "impaired glucose tolerance" refers to a condition marked by a pre-diabetic state of hyperglycemia that is associated with insulin resistance. The term "insulin resistance" refers to a physiological condition wherein insulin becomes less effective at lowering blood sugar levels. The term "gestational diabetes mellitus" refers to a condition in which women without previously diagnosed type 2 diabetes exhibit high blood glucose levels during pregnancy. As used herein, the term "pre-diabetes" refers to a condition wherein a subject exhibits impaired fasting glycemia and/or impaired glucose tolerance which has not progressed to diabetes mellitus or type 2 diabetes. As used herein, the term "type 2 diabetes" also known as non-insulin-dependent diabetes mellitus (NIDDM) is a metabolic disorder characterized by high blood glucose in the context of insulin resistance and relative insulin deficiency. Optionally, type 2 diabetes refers to subjects with fasting plasma glucose ≥7.0 mmol/l (126 mg/dl). Suitable criteria for the identifying subjects with impaired glucose homeostasis, diabetes, β-cell dysfunction and/or related conditions are found in *Standards of Medical Care in Diabetes*—2012 Diabetes Care, volume 35, supplement 1, January 2012, hereby incorporated by reference.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and domain antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Antibodies for CMPF are commercially available from Life Sciences Advanced Technology Inc. (St. Petersburg, Fla.) or Noventein Biosciences (Cambridge, Mass.). However, a person skilled in the art will appreciate that one could produce other antibodies that are specific for CMPF or for biomarkers associated with CMPF metabolism or degradation. To produce monoclonal antibodies, antibody producing cells (lymphocytes) can be harvested from an immunized animal with the antigen of interest (e.g. CMPF) and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the antigen of interest and the monoclonal antibodies can be isolated.

As used herein the term "CMPF inhibitor" includes any agent which sequesters or lowers the physiological concentration of CMPF in blood or plasma and/or lowers the physiological concentration of CMPF in pancreatic islet cells. In one embodiment, the CMPF inhibitor increases the clearance of CMPF from plasma. In one embodiment, the CMPF inhibitor is an OAT activator. In one embodiment, the OAT activator increases the clearance of CMPF from plasma. In one embodiment, the CMPF inhibitor lowers the physiological concentration of CMPF in pancreatic β-cells. In one embodiment, the CMPF inhibitor inhibits the activity of an Organic Anion Transporter (OAT) expressed in pancreatic islet cells. In one embodiment, the CMPF inhibitor is an OAT inhibitor.

As used herein, "OAT inhibitor" refers to any agent that inhibits the expression or activity of an Organic Anion Transporter (OAT). In one embodiment, the OAT inhibitor inhibits the expression or activity of OAT1 (also known as SLC22A6), OAT3 (also known as SLC22A8) and/or OAT4 (also known as SLC22A11). Examples of OAT inhibitors include, but are not limited to, probenecid, benzylpenicillin (PCG) and p-aminohippurate (PAH).

As used herein "OAT activator" refers to any agent that increases the expression or activity of an Organic Anion Transporter (OAT). In one embodiment, the OAT activator is specific for OAT4 (also known as SLC22A11).

"Treating" or "Treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease (e.g. maintaining sufficient insulin and/or physiologically normal levels of blood glucose), preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. In one embodiment, treatment methods comprise administering to a subject a therapeutically effective amount of a CMPF inhibitor as described herein and optionally consists of a single administration, or alternatively comprises a series of administrations. In one embodiment, "treating" includes improving β-cell function in a subject with impaired glucose homeostasis.

As used herein, the phrase "effective amount" or "therapeutically effective amount" means an amount effective, at dosages and for periods of time necessary to achieve the desired result. For example in the context of treating impaired glucose homeostasis, an effective amount is an amount that helps improve β-cell function or helps stabilize levels of insulin and/or glucose at physiologically normal concentrations compared to the response obtained without administration of the compound. Effective amounts may vary according to factors such as the disease state, age, sex and weight of the subject. The amount of a given compound that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art.

In one embodiment, the compounds such as the CMPF inhibitors described herein are prepared or formulated for administration to a subject in need thereof as known in the art. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999.

Methods of Identifying or Monitoring β-cell Dysfunction

In one embodiment, there is provided a method of identifying a subject having, or at risk of developing, impaired glucose homeostasis. In one embodiment, the method comprises:

(a) determining a test level of 3-carboxy-4-methyl-5-propyl-2-furanpropanoic acid (CMPF) in a sample from a subject; and (b) comparing the test level of CMPF to a control level wherein a difference or similarity in the test level of CMPF relative to the control level is indicative of the subject having, or at risk of developing, impaired glucose homeostasis.

There is also provided a method of monitoring a subject having impaired glucose homeostasis comprising:

(a) determining a test level of 3-carboxy-4-methyl-5-propyl-2-furanpropanoic acid (CMPF) in a sample from the subject; and (b) comparing the test level of CMPF to a level of CMPF from the subject at an earlier time point, wherein an increase in the level of CMPF is indicative of more severe impaired glucose homeostasis in the subject and a decrease in the level of CMPF is indicative of improved glucose homeostasis in the subject.

In one embodiment, the methods described herein for identifying or monitoring subjects with impaired glucose homeostasis are useful for identifying or monitoring subjects having, or at risk of developing, β-cell dysfunction. Optionally, the methods described herein include obtaining or providing a sample from the subject. For example, in one embodiment, the sample is a blood, plasma, serum or urine sample or another biological sample that can be analyzed for CMPF levels.

In one embodiment the methods described herein are useful for identifying or monitoring conditions wherein the regulation of blood glucose levels is impaired. Examples of conditions characterized by impaired glucose homeostasis include, but are not limited to, β-cell dysfunction, impaired glucose tolerance, pre-diabetes, gestational diabetes mellitus (GDM), insulin resistance or type 2 diabetes. In one embodiment, the magnitude of the CMPF level in a subject reflects the severity of the impairment of the regulation of blood glucose levels in the subject. In one embodiment, the magnitude of the CMPF level in a subject reflects the severity of β-cell dysfunction in the subject.

A skilled person will appreciate that differences or similarities between the levels of CMPF observed in a test sample from a subject and a control level can be used to identify or monitor subjects having or suspected of having impaired glucose homeostasis.

For example, if one is identifying or monitoring gestational diabetes mellitus (GDM), the control can be from a subject or group of subjects who are known not to have GDM and a higher level of CMPF in the test subject relative to the control is indicative of GDM or an increased risk of GDM in the test subject. Optionally, the control can be from a subject or group of subjects who are known to have GDM and a similar level of CMPF in the test subject relative to the control is indicative of GDM or an increased risk of GDM in the test subject.

In one embodiment, the control is from a subject or group of subjects who are known not to have impaired glucose tolerance and a higher level of CMPF in the test subject relative to the control is indicative of impaired glucose tolerance or an increased risk of impaired glucose tolerance in the test subject. Optionally, the control can be from a subject or group of subjects who are known to have impaired glucose tolerance and a similar level of CMPF in the test subject relative to the control is indicative of impaired glucose tolerance or an increased risk of impaired glucose tolerance in the test subject.

In one embodiment, the control is from a subject or group of subjects who are known not to have pre-diabetes and a higher level of CMPF in the test subject relative to the control is indicative of pre-diabetes or an increased risk of pre-diabetes in the test subject. Optionally, the control can be from a subject or group of subjects who are known to have pre-diabetes and a similar level of CMPF in the test subject relative to the control is indicative of impaired glucose tolerance or an increased risk of pre-diabetes in the test subject.

In one embodiment, the control is from a subject or group of subjects who are known not to have insulin resistance and a higher level of CMPF in the test subject relative to the control is indicative of insulin resistance or an increased risk of insulin resistance in the test subject. Optionally, the control can be from a subject or group of subjects who are known to have insulin resistance and a similar level of CMPF in the test subject relative to the control is indicative of insulin resistance or an increased risk of insulin resistance in the test subject.

In one embodiment, the control is from a subject or group of subjects who are known not to have type 2 diabetes and a higher level of CMPF in the test subject relative to the control is indicative of type 2 diabetes or an increased risk of type 2 diabetes in the test subject. Optionally, the control can be from a subject or group of subjects who are known to have type 2 diabetes and a similar level of CMPF in the test subject relative to the control is indicative of type 2 diabetes or an increased risk of type 2 diabetes in the test subject.

In one embodiment, the control level is representative of a level of CMPF in subjects with normal glucose tolerance and an increased level of CMPF in the test sample relative to the control level is indicative of impaired glucose tolerance.

Levels of CMPF in plasma of subjects without impaired glucose homeostasis are generally in the range of about 10 μM to 30 μM, typically about 20 μM. In one embodiment, plasma CMPF levels in a test subject significantly higher than about 20 μM are indicative of impaired glucose homeostasis. In one embodiment, a level of CMPF in plasma greater than 50 μM, 100 μM, 150 μM, 200 μM, 300 μM or 500 μM is indicative of impaired glucose homeostasis. In one embodiment, the magnitude of the level of CMPF in a subject is indicative of the severity of impaired glucose homeostasis in the subject.

In one embodiment, the step of determining the test level of CMPF in the sample comprises detecting CMPF in the sample. In one embodiment, the step of determining the test level of CMPF includes detecting or determining the level of a metabolite or analyte of CMPF in the sample that is representative of CMPF levels. For example, in one embodiment, the methods described herein include detecting or determining the level of one or more precursor molecules that give rise to CMPF, or by-products of CMPF metabolism or degradation. In one embodiment, the methods described herein include detecting or determining the level of one or more albumin-bound proteins/metabolites/peptides such as thyroxine (thyroid hormone) which have altered abundance due to increased plasma levels of CMPF. CMPF is highly albumin-bound and can out-compete other albumin-bound proteins. (Lim et al., Metabolism (1993), 42(11); 1468). Therefore, elevated levels of CMPF in the blood may cause displacement of other albumin bound proteins such as thyroxine, increasing their free (non-albumin bound) levels in the blood.

Optionally, the methods described herein include processing the sample prior to detecting CMPF. For example, in one embodiment the sample is processed to remove constituents from the sample and/or isolate or purify CMPF in the sample that may interfere with the detection of CMPF. In one embodiment, the sample may be processed using chromatography. In one embodiment, the sample is processed to remove highly abundant proteins such as albumin prior to detecting CMPF in the sample.

Different methods known to a skilled person for detecting CMPF are useful for the purposes of the methods described herein. For example in one embodiment CMPF is detected using mass spectrometry (MS), optionally gas chromatography/mass spectrometry (GC-MS) or liquid chromatography mass spectrometry (LC-MS). In one embodiment, the step of detecting CMPF includes using High Performance Liquid Chromatography (HPLC) or Nuclear Magnetic Resonance (NMR) spectroscopy.

In one embodiment, immunohistochemical methods are useful for detecting CMPF. For example, CMPF is readily detected using antibodies that specifically bind CMPF. In one embodiment, CMPF is detected using an Enzyme-Linked Immunosorbent Assay (ELISA). Any method of labeling the antibody that facilitates detection would be useful (e.g. radioactively labeled peptide, enzyme or fluorescently tagged peptide). Other assays useful for detecting CMPF may include, but are not limited to: radioimmunoassay, enzyme-linked immunosorbent assay (ELISA), "sandwich" assays, precipitin reactions, gel diffusion immunodiffusion assay, agglutination assay, fluorescent immunoassays and immunoelectrophoresis assays.

Methods of Causing β-cell Dysfunction

In one aspect of the disclosure, higher than normal levels of CMPF have been shown to cause β-cell dysfunction. Accordingly, in one embodiment, there is provided a method of causing β-cell dysfunction in one or more β-cells comprising contacting the one or more β-cells with CMPF. Optionally, the β-cells are islet cells. In one embodiment, the β-cells are in vitro, in vivo or ex vivo. The methods described herein for causing β-cell dysfunction are useful for generating in vitro, in vivo or ex vivo models of conditions characterized by β-cell dysfunction such as diabetes.

In one embodiment, contacting β-cells with supra-physiological concentrations of CMPF will cause β-cell dysfunction. For example, in one embodiment, β-cells are contacted with a concentration of CMPF of greater than 50 μM, 100 μM, 150 μM, 200 μM, 300 μM or 500 μM. A skilled person will appreciate that the greater the concentration of CMPF the greater the dysfunction caused in β-cells.

In one embodiment, the β-cells are in vitro and contacting the β-cells with CMPF causes impaired insulin secretion. Alternatively the β-cells are in vivo, such as in an animal model of β-cell dysfunction. In one embodiment the β-cells are in a subject in vivo, and the method comprises administering CMPF to the subject. In one embodiment, the subject is an animal with β-cells that store and release insulin, such as a mouse or rat.

A skilled person will appreciate administering a suitable dosage of CMPF in order to elicit the desired level of β-cell dysfunction in vitro, or in the subject in vivo. In one embodiment, the method comprises administering at least 5 mg/kg CMPF to the subject. In one embodiment, the method comprises administering at least 7 mg/kg, at least 10 mg/kg or at least 20 mg/kg to the subject. Optionally, CMPF can be administered orally, by injection or by any other means such that the level of CMPF is increased in the blood. For example, CMPF can be administered by intraperitoneal, intravenous, subcutaneous or intramuscular injections as well as through oral gavage or through an enriched diet with CMPF or the precursor fatty acid. In one embodiment, there is provided a composition comprising CMPF and one or more pharmaceutically acceptable carriers useful for administration to a subject.

In one embodiment, contacting one or more β-cells with CMPF causes a conditions characterized by β-cell dysfunction selected from impaired glucose tolerance, pre-diabetes, gestational diabetes mellitus, insulin resistance or type 2 diabetes. A skilled person will appreciate that causing β-cell dysfunction in vitro, ex vivo or in vivo using the methods described herein can be used for generating models of β-cell dysfunction. In one embodiment, the methods described herein include using β-cells or subjects that have been administered CMPF as an animal model for a condition characterized by β-cell dysfunction.

Methods of Screening for Compounds

In one aspect, there is provided a method of screening for agents that affect the activity of β-cells. As described herein, CMPF can be used to generate models of β-cell dysfunction. Agents that restore or improve β-cell function in cells that have higher than physiologically normal levels of CMPF are therefore candidates for the treatment of conditions characterized by β-cell dysfunction. In one embodiment, there is provided a screening method comprising:

(a) providing one or more β-cells wherein the activity of the β-cells has been reduced by contacting the β-cells with 3-carboxy-4-methyl-5-propyl-2-furanpropanoic acid (CMPF)

(b) contacting the β-cells with a test agent; and (c) determining the effect of the test agent on the activity of the β-cells.

Optionally, the β-cells are in vivo, in vitro or ex vivo. In one embodiment, the β-cells are islet cells. In one embodiment, the test agent is identified as effective if its effect on activity is above a threshold level. For example, in one embodiment, test agent may be identified as effective if it restores at least 10%, at least 20%, at least 30%, at least 40% or at least 50% of the activity of the β-cells compared to the activity of the β-cells before their activity had been reduced by contacting the cells with CMPF. In one embodiment, the activity is any activity of the β-cell which improves the storage or secretion of insulin or the regulation of glucose in the blood. For example, in one embodiment the activity is the size or viability of the β-cells such as determined by detecting β-cell mass expansion or β-cell loss. In on embodiment, the activity is insulin exocytosis. In one embodiment, the activity is glucose stimulated insulin secretion (GSIS). The activity of the β-cells may also be determined by detecting the transcription or translation of insulin or insulin transcription factor genes, glucose-sensing genes or insulin processing genes. In one embodiment, the method includes determining the expression of one or more insulin or insulin transcription factor genes or one or more glucose-sensing genes or one or more insulin processing genes. In one embodiment, the insulin or insulin transcription factor genes are INS, PDX1, MAFA or NKX6.1. In one embodiment, the glucose-sensing genes are GLUT2, GLUT1 or GCK. In one embodiment the insulin processing genes are PCSK1, PCSK2, or CPE. In one embodiment, the genes are selected from SLC2A1, SLC2A2, GCK, Kir6.2, ABCC8, CACNA1D, CACNA1A, CACNA1H, KCNB1, SNAP25, STX1A, VAMP2, SYN1A, PDX1, MAFA, NKX6.1, INS (in mice INS1 or INS2), PCSK1, PCSK2 and CPE. Optionally, the genes described herein are human or their non-human counterparts.

A skilled person in the art will appreciate that a number of different assays may be used to determine the activity of β-cells. For example, expression of relevant genes can be determined by RT-PCR, quantitative RT-PCR, microarrays or by other assays known in the art.

In one embodiment, the screening method described herein is useful for identifying compounds that affect β-cell mass expansion and the activity of the β-cells is determined by a Brdu and/or Ki67 assay. In another embodiment, the methods described herein are useful for identifying compounds that affect β-cell loss and β-cell loss is determined by Annexin 5-propidium iodide staining, trypan blue staining or caspase 3 activity assays/staining.

Treatment of β-cell Dysfunction Using CMPF Inhibitors

As described herein, higher than normal levels of CMPF have been shown to be associated with β-cell dysfunction. Reducing the levels of CMPF circulating in vivo in a subject with elevated levels of CMPF and/or a condition characterized by β-cell dysfunction is therefore expected to have a beneficial effect on β-cell activity. Furthermore, reducing the levels of CMPF in pancreatic islet cells such as β-cells is expected to have a beneficial effect on β-cell activity. As shown in Example 2, OAT transporters are expressed in pancreatic islet cells and inhibition of OATs blocks CMPF-inhibition of β-cell function. Inhibiting OAT transporter function in subjects with a condition characterized by β-cell dysfunction is therefore expected to have a beneficial effect on β-cell activity.

Furthermore, as shown in Example 2 injections of CMPF impair β-cell function and prevent glucose stimulated insulin secretion in vivo. The use of a CMPF inhibitor such as probenecid abolished the effect of CMPF on glucose-stimulated insulin secretion. Remarkably, the administration of probenecid has also been shown to elevate circulating CMPF levels in vivo without altering glucose tolerance. While probenecid raises blood levels of CMPF, it is thought to prevent it from entering the beta cell and therefore protects the beta cell from effects of CMPF. CMPF inhibitors that reduce the physiological levels of CMPF in the blood and/or pancreatic islets cells are therefore expected to be useful for the treatment of β-cell dysfunction, such as in subjects with impaired glucose homeostasis. Similarly, OAT inhibitors and/or specific OAT inhibitors such as PCG which is specific for OAT3 are expected to be useful for the treatment of β-cell dysfunction Accordingly, in one aspect, there is provided a method for the treatment of a condition characterized by β-cell dysfunction by reducing the physiological levels of CMPF in a subject. In one embodiment, the method comprises administering to the subject a 3-carboxy-4-methyl-5-propyl-2-furanpropanoic acid (CMPF) inhibitor. In one embodiment, the method comprises reducing the physiological levels of CMPF in pancreatic islet cells in a subject. Optionally, the subject has, or is suspected of having, impaired glucose tolerance, pre-diabetes, insulin resistance, gestational diabetes mellitus or type 2 diabetes.

In one embodiment, there is also provided the use of a 3-carboxy-4-methyl-5-propyl-2-furanpropanoic acid (CMPF) inhibitor for the treatment of β-cell dysfunction in a subject in need thereof. In some embodiments, the CMPF inhibitor reduces the physiological levels of CMPF in the subject, such as the levels of CMPF circulating in blood and/or the levels of CMPF in pancreatic islet cells. Optionally, the subject has, or is suspected of having, impaired glucose tolerance, pre-diabetes, insulin resistance, gestational diabetes mellitus or type 2 diabetes.

In one aspect, there is provided a method for the treatment of a condition characterized by β-cell dysfunction by modulating the interaction of CMPF with one or more Organic Anion Transporters (OAT) in a subject. For example, in one embodiment the administration or use of an OAT-specific inhibitor such as probenecid or penicillin G (PCG) helps reduce the physiological levels of CMPF in pancreatic islet cells. In one embodiment, the administration or use of an OAT-specific activator helps reduce the physiological levels of CMPF in the blood. In one embodiment, the OAT-specific activator is an activator of OAT4.

Kits for Identifying or Monitoring β-cell Dysfunction

In one embodiment, there is provided pre-packaged kits that comprise some or all of the reagents necessary to perform any of the methods described herein. Optionally, the kits may include one or more control samples. In some embodiments the control sample is known to contain a specific level of CMPF, such as about 20 μM, about 50 μM, about 100 μM, about 150 μM or about 200 μM. In other embodiments, the kits include a negative control that is known not to contain CMPF. In a further embodiment, the control sample is known to contain a certain level of CMPF or correspond to impaired glucose homeostasis or a specific condition characterized by impaired glucose homeostasis or β-cell dysfunction. In some embodiments the kits include at least one antibody selective for CMPF. In some embodiments, the kits will include detailed instructions for carrying out the methods described herein.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application:

EXAMPLE 1

CMPF is a Biomarker for Impaired Glucose Homeostasis

Materials and Methods

Plasma samples were collected from women in either the late second or early third-trimester of pregnancy. Glucose tolerance was tested first using a glucose challenge test (GCT) between 24 and 28 weeks gestation, followed by a 3 hour 100 g-glucose oral glucose tolerance test (OGTT). Based on the results from these tests women were categorized into 4 groups: gestational diabetes mellitus (GDM), gestational impaired glucose tolerance (GIGT), abnormal GCT but normal glucose tolerance by OGTT (abGCT NGT), and normal GCT normal OGTT (NGT). Plasma samples used for analysis were taken after fasting, before the start of the OGTT.

The fasting plasma samples were tested using selected reaction monitoring mass spectroscopy (SRM-MS) in combination with either gas chromatography (GC) or liquid chromatography (LC) for separation of the analytes to quantitatively compare the metabolome of GDM and NGT patients. The metabolome represents the collection of all metabolites in a biological cell, tissue, organ or organism, which are the by-products of metabolism and include but are not limited to carbohydrates, amino acids, and FFAs. The relative abundance of these molecules changes extremely rapidly in response to stimulation such as eating, exercising, and in pathophysiological conditions such as GDM or T2D. Twelve plasma samples from each group were investigated and 342 named biochemicals were quantified in each sample. A low q-value (<0.1) was used to determine confidence in results.

Results

Figure 2:
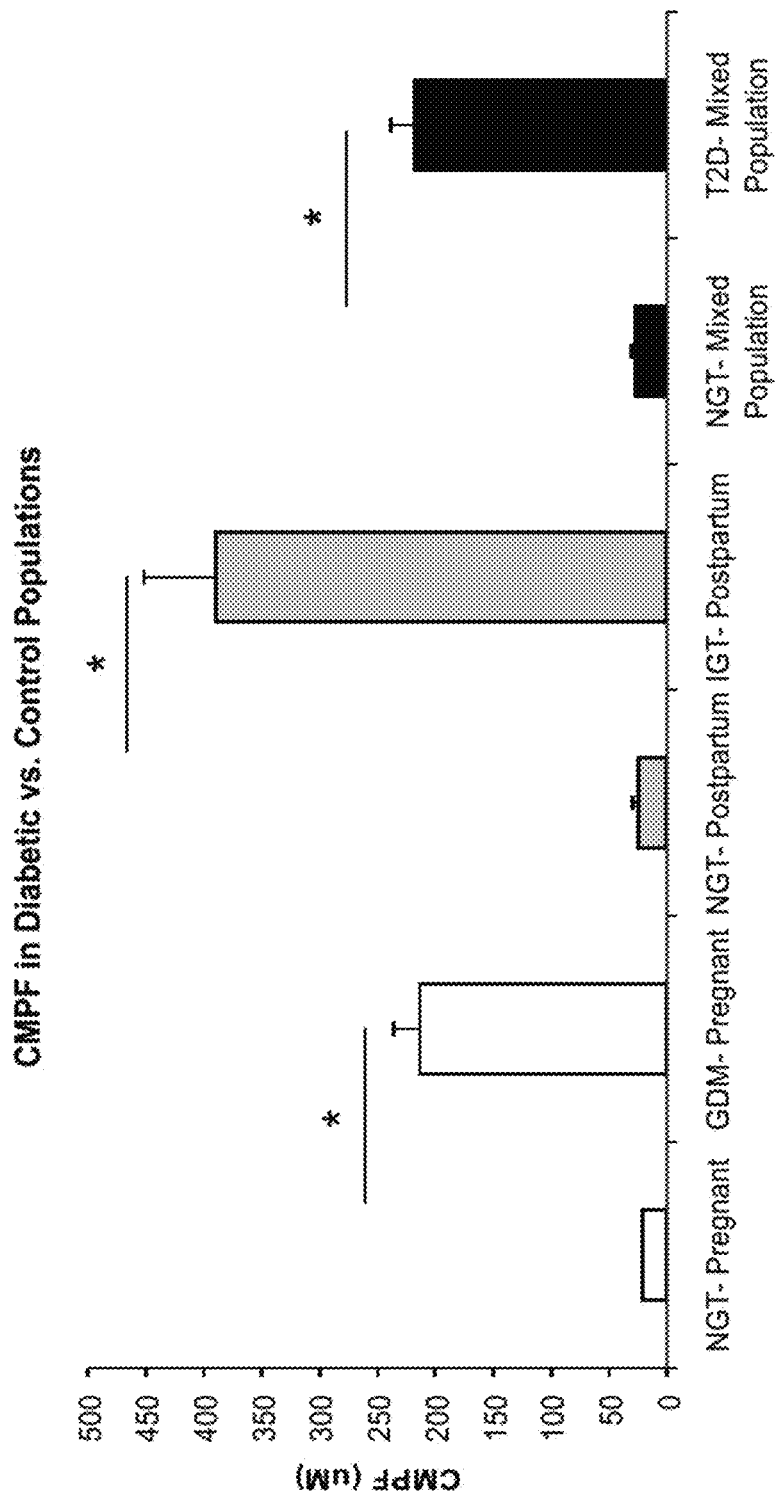
FIG. 2 shows ELISA results showing significantly elevated levels of CMPF in plasma samples of GDM vs. NGT patients taken during pregnancy, IGT vs. NGT patients taken postpartum, and T2D vs. NGT controls in a mixed gender population. GDM-pregnant patients (N=24) have ~10 fold greater plasma concentration of CMPF as compared to NGT-pregnant (N=24) controls, p<0.001. Plasma samples taken from the same pregnant women one year postpartum show that women who had GDM and went on to develop IGT postpartum (N=5) had a 13 fold increase in plasma CMPF compared to women who maintained NGT both during pregnancy and postpartum (N=5). Plasma samples from a mixed gender population of T2D (N=6) show a ~10 fold increase in plasma CMPF as compared to an NGT control population (N=6). In all cases, P<0.05, and samples are matched for age, race, gender and pre-pregnancy BMI. For the pregnancy and postpartum samples, patients are also matched for family history of diabetes.

Of the 342 metabolites investigated, 52 were significantly changed (P<0.05) between the GDM and NGT populations. Grouping of the metabolites based on biological classification revealed that patients with GDM have significantly increased levels of free fatty acids (FFAs) compared to NGT patients, indicating an increased reliance on alternative (non-glucose) sources of energy (FIG. 1a). The most significantly changed metabolite in the screen, 3-carboxy-4-methyl-5-propyl-2-furanpropanoic acid (CMPF), was significantly elevated (5.69 fold) in GDM as compared to NGT samples. An independent screen of a second cohort of samples replicated this result (FIG. 1b). This finding was further validated using an ELISA kit specific for human CMPF in 48 human plasma samples (24 NGT and 24 GDM) (FIG. 2). Importantly, CMPF was shown to be even more significantly elevated in 5 women who developed IGT within one year post-partum following GDM as compared to 5 women who maintained NGT during both of these time periods, as well as in a mixed gender population of T2D patients compared to NGT matched controls (FIG. 2). This strongly suggests that CMPF is involved in the development of T2D as well as GDM. Furthermore, levels of CMPF are therefore useful for predicting impaired glucose homeostasis and type 2 diabetes in subjects with glucose levels that are more or less normal.

Since beta cell failure is a major underlying cause of both GDM and T2D, the effect of increased CMPF on beta cell function was investigated both in vitro and in vivo. Using physiological concentrations of CMPF (20 uM and 200 uM, as observed in our NGT-pregnant and GDM-pregnant samples respectively (FIG. 2)), as well as a vehicle control (EtOH), its effect was studied on glucose-stimulated insulin secretion (GSIS) and insulin secretion in response to direct depolarization using the secretagogue KCl in an immortalized murine beta cell line (MIN6), as well as primary isolated human and murine islets (FIG. 3A). Pre-treatment of monolayer MIN6 cells with 200 uM CMPF for 4 hours significantly impaired GSIS as compared to 20 uM and vehicle controls, while identical treatment with 200 uM CMPF caused an equivalent impairment in both human and murine islets after 24 hours (FIG. 3B, C). Therefore, high physiologically relevant levels of CMPF impair GSIS.

Figure 4:
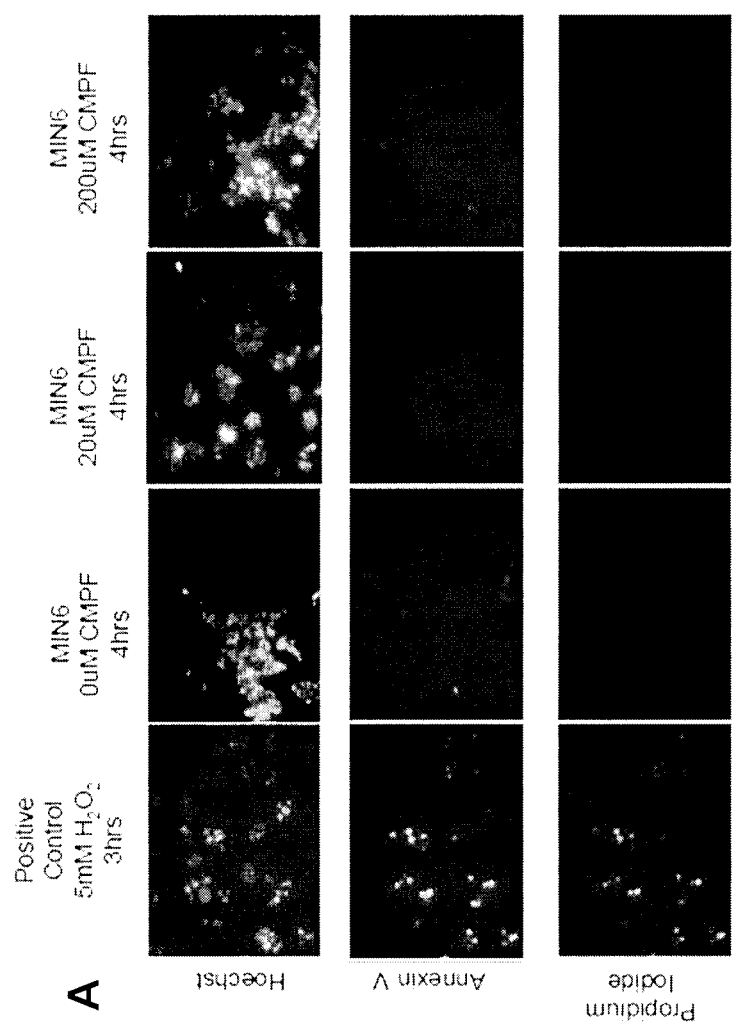
FIG. 4 shows that CMPF treatment does not induce apoptosis or necrosis in in vitro treated cells despite inhibiting GSIS. A) MIN6 cells were treated for 4 hrs with 0 uM (EtOH vehicle control), 20 uM or 200 uM CMPF prior to being loaded with Annexin V and propidium iodide fluorescent dyes, and counterstained with Hoechst dye. Annexin V and propidium iodide staining were only observed in the positive control, MIN6 treated with 5 mM $H_2O_2$ for 3 hrs. B) Primary CD1 islets were dispersed and treated with vehicle control (0 CMPF, black), 20 uM CMPF (grey), or 200 uM CMPF (white) for 48 hours, then stained with Annexin V, Propidium Iodide and Hoechst dye. Quantification of double positive staining was assessed by an Arrayscan VTI HCS reader.
Figure 4:
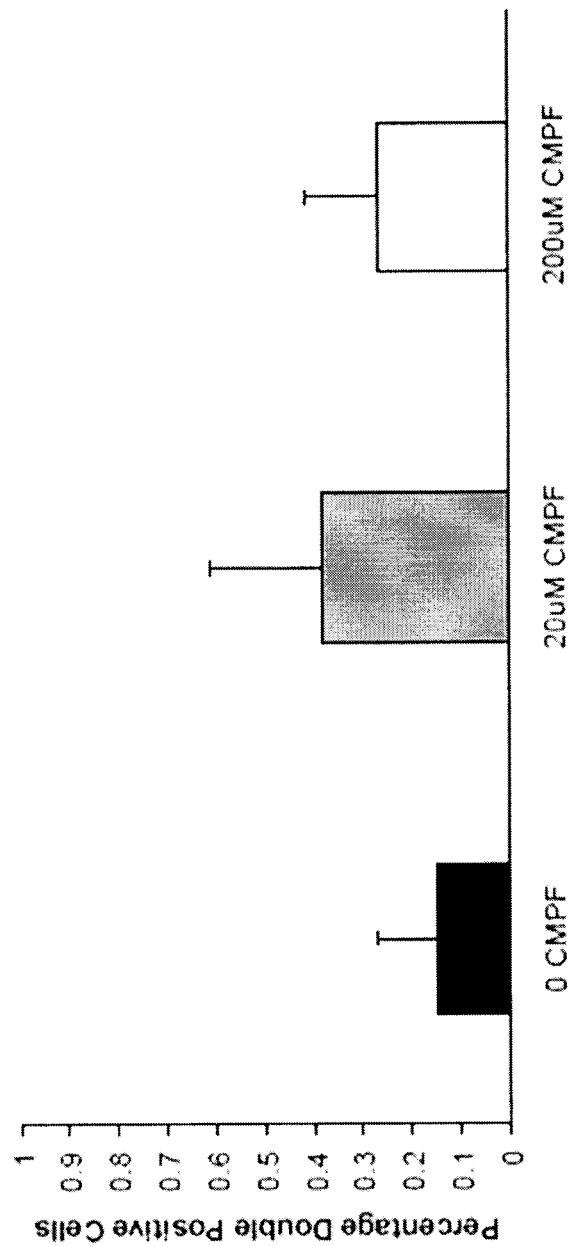

Next the mechanism underlying the observed impairment in GSIS following treatment with CMPF was investigated. To determine whether CMPF was inhibiting GSIS by inducing beta cell apoptosis, Annexin V and Propidium Iodide staining was performed in MIN6 cells treated with vehicle (EtOH), 20 uM or 200 uM CMPF for 4 hrs to look for apoptosis and necrosis respectively. No significant staining was observed in any of the CMPF treatment conditions, despite 200 uM CMPF for 4 hrs causing significant reduction in GSIS. MIN6 cells treated with 5 mM $H_2O_2$ for 3 hrs were used as a positive control (FIG. 4). CMPF does not impair GSIS by inducing beta cell apoptosis or necrosis.

Figure 5:
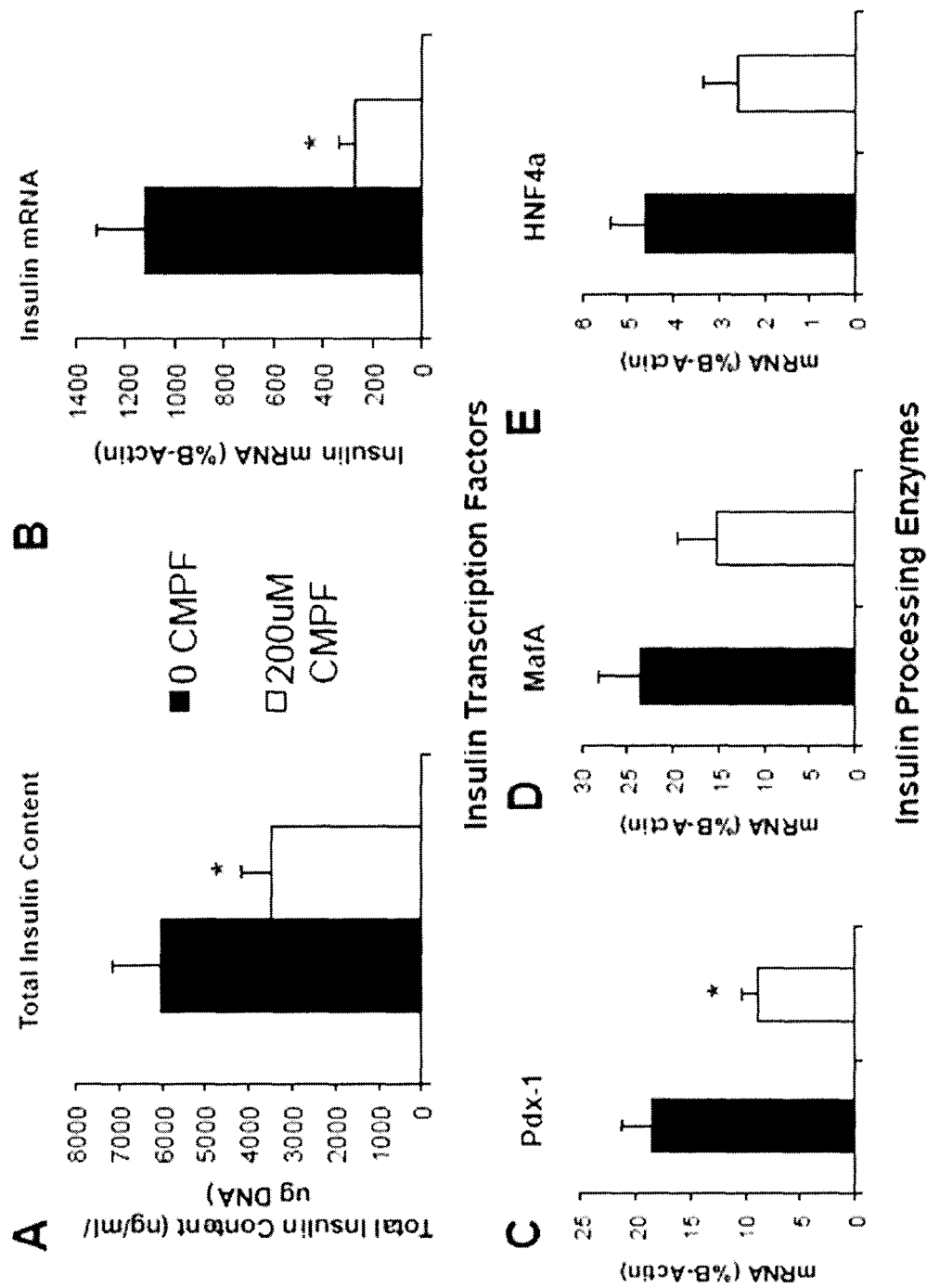
FIG. 5 shows that CMPF treatment reduces total insulin content and expression of genes associated with insulin biosynthesis and glucose sensing. Murine islets were treated for 24 hrs with vehicle control (0 CMPF), 20 uM (20 CMPF), or 200 uM (200 CMPF) CMPF, and assessed for total insulin content and mRNA expression. 200 uM CMPF significantly reduced total insulin content (A) and insulin mRNA (B) as compared to vehicle control. Decreased insulin mRNA expression may be due to decreased expression of insulin transcription factors including Pdx-1, MafA and HNF4a (C), (D) and (E). Decreased expression of insulin processing enzymes PCSK1, 2 and CpE (F), (G), (H) indicate that CMPF may also impair post-translational insulin processing. Finally, CMPF causes decreased expression of the beta cell glucose transporter GLUT2, and GCK, the rate-limiting enzyme critical for glucose metabolism (I) and (J), perhaps impairing glucose sensing and metabolism. In all cases n=4, *P<0.05.
Figure 5:
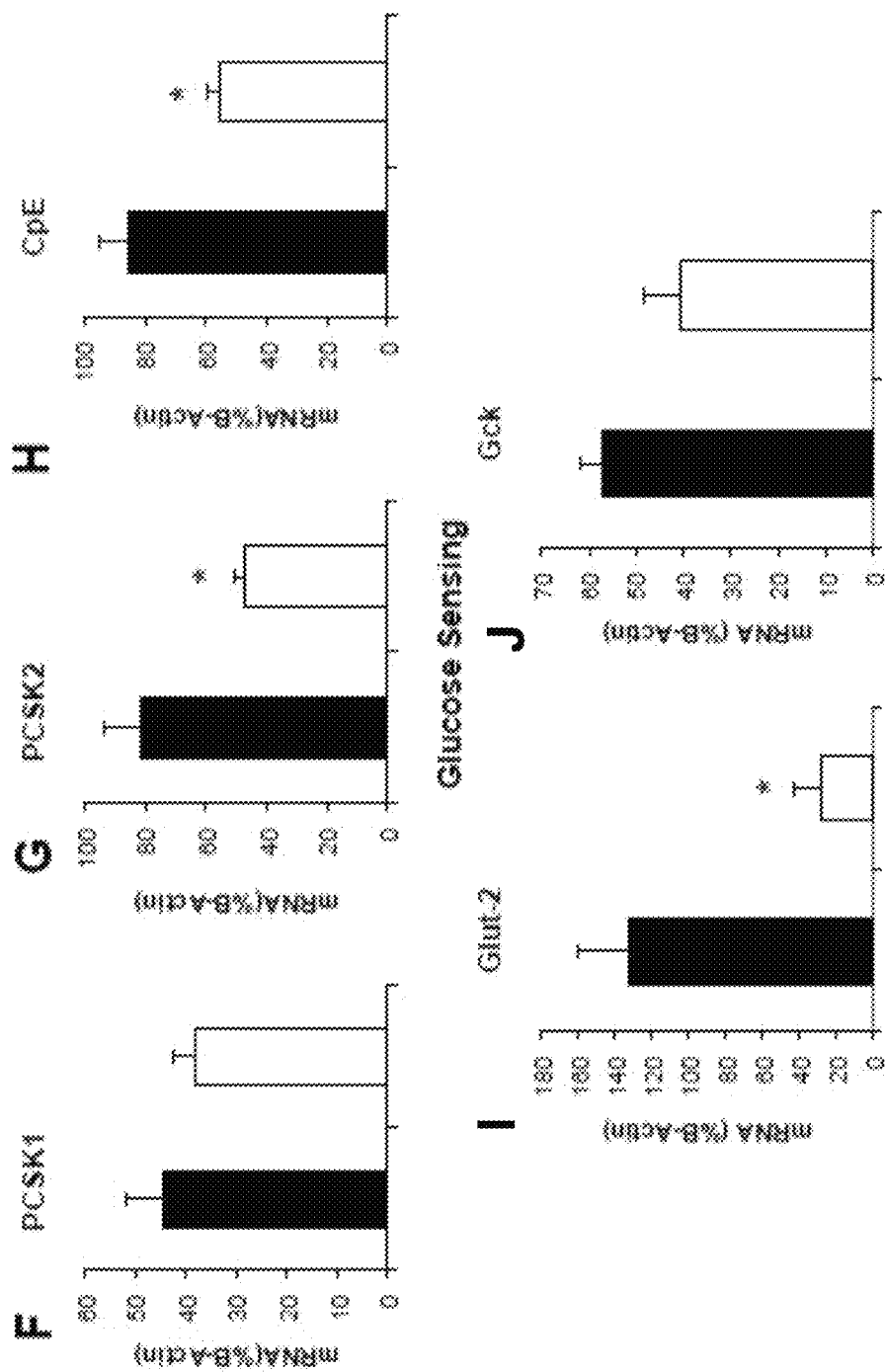

In the absence of apoptosis and necrosis, CMPF must be impairing GSIS by causing beta cell dysfunction. First, the effect of CMPF treatment on insulin biosynthesis was investigated to determine if insulin is available to be released upon stimulation. MIN6, murine and human islets were treated with vehicle control, 20 uM and 200 uM CMPF for 4 hrs (MIN6) or 24 hrs (islets), and total insulin content measured. In all cases, total insulin content was significantly reduced by treatment with 200 uM CMPF as compared to vehicle controls (murine islets used as representative, FIG. 5A). The reduction in total insulin content was observed in the absence of changes in total DNA, validating that CMPF is not inducing apoptosis. Lower total insulin content may be due to either defective insulin processing from proinsulin to mature insulin, or insufficient insulin transcription. To determine the mechanism through which CMPF is reducing total insulin content, quantitative PCR (qPCR) was performed on RNA that was isolated from murine islets treated with either vehicle control or 200 uM CMPF for 24 hrs. A significant reduction in insulin mRNA was observed (FIG. 5B), as well as insulin transcription factors PDX1, MAFA and HNF4a (FIGS. 5C, 5D and 5E), suggesting that CMPF impairs insulin transcription. Additionally, significantly lower levels of mRNA were observed for the insulin processing enzyme CpE, and trending lower levels of PCSK1 and 2 (FIGS. 5F, 5G, 5H). Together these results suggest that CMPF causes beta cell dysfunction by inhibiting insulin transcription and post-translational processing.

The observed significant reduction in the beta cell-specific transcription factor PDX1 suggested investigating a possible inhibition of expression of critical glucose-sensing genes in CMPF treated islets. PDX-1 has been reported to be essential for the transcription of the beta cell glucose transporter GLUT2, as well as the rate-limiting glucose processing enzyme glucokinase (GCK). qPCR was again used to determine that 200 uM of CMPF for 24 hrs on murine islets significantly reduced expression of GLUT2, and caused a trend toward lower expression of GCK compared to vehicle treated controls (FIGS. 5I and 5J). CMPF may therefore impair GSIS by lowering GLUT2 expression, preventing the beta cells from taking up and subsequently metabolizing glucose to stimulate insulin secretion.

Figure 6:
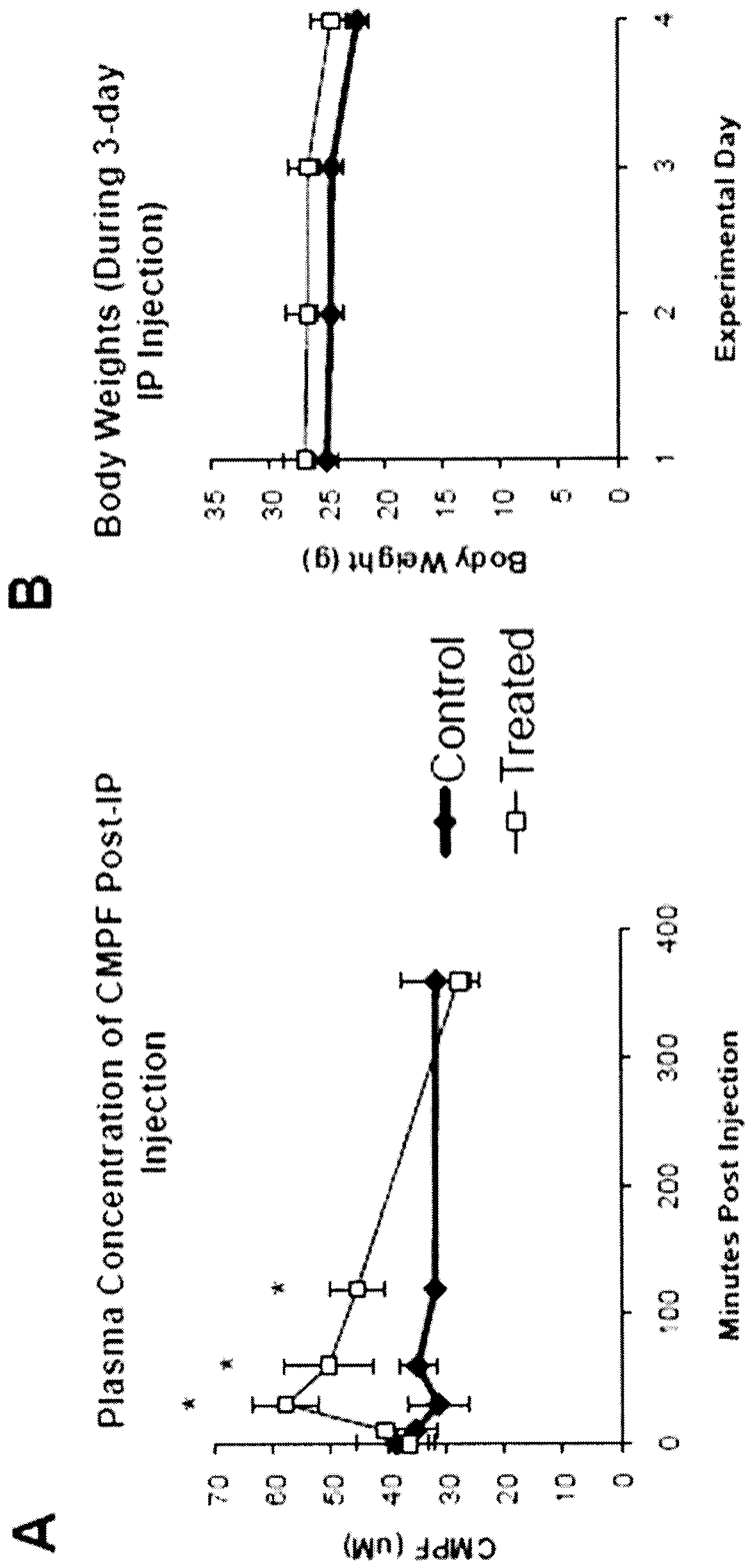
FIG. 6 shows that IP injections of CMPF elevate plasma levels and OGTTs performed following 3 days of IP injection show impaired insulin secretion and impaired glucose tolerance in mice treated with CMPF. CD1 mice were injected IP with either vehicle control (black) or CMPF (white). A) Plasma samples were taken at 10, 30, 60, 120 and 360 minutes post-IP injection and assayed for CMPF. Mice injected with CMPF had significantly elevated (p<0.05) levels of plasma CMPF for up to 2 hours but not at 6 hours post-injection (n=4/group). Over the 3-day course of IP injections, mice were monitored for body weight (B), random-fed blood glucose (C) and plasma insulin (C). There was no difference in any of these parameters. Following 3 consecutive days of CMPF injections, mice were fasted for 14 hrs and OGTTs were performed. CMPF treated mice have significantly impaired insulin secretion compared to vehicle injected controls (D) and impaired glucose tolerance (C) (n=10 per group, p<0.05).
Figure 6:
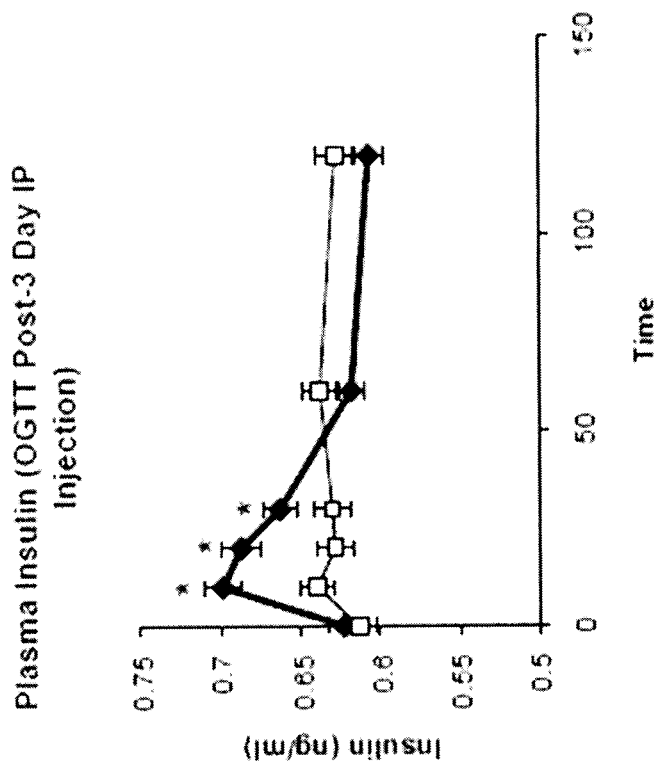
Figure 6:
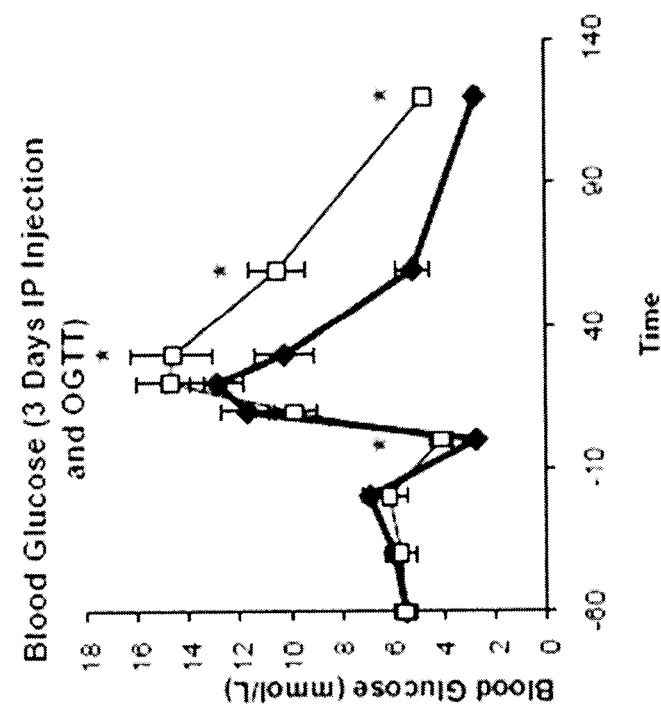
Figure 8:
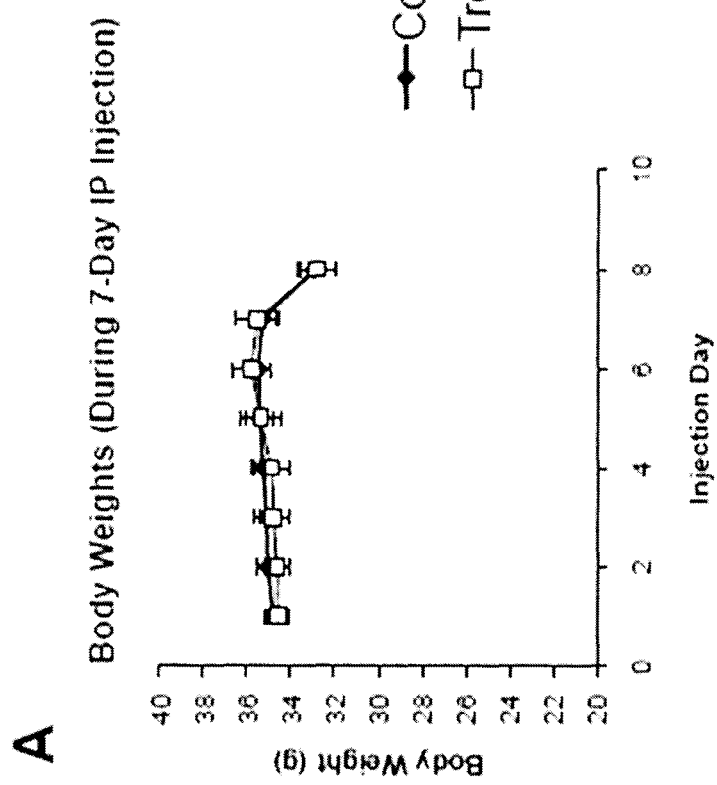
FIG. 8 shows that CMPF may cause insulin resistance and OGTTs performed following 7 days of IP injection show impaired insulin secretion and impaired glucose tolerance in mice treated with CMPF. CD1 mice were injected IP with either vehicle control (black) or CMPF (white). Over the 7-day course of IP injections, mice were monitored for body weight (A), and random-fed blood glucose (B) and plasma insulin (C). There was no difference in either body weight or blood glucose, however the CMPF-treated mice had significantly elevated plasma insulin levels on days 4-7 of injections, indicating that CMPF is contributing to insulin resistance. The lower body weights on day 8 are following a 14-hour fast, immediately prior to the OGTTs. Following 7 consecutive days of CMPF injections, mice were fasted for 14 hrs and OGTTs were performed. CMPF treated mice have significantly impaired glucose tolerance (D) compared to controls, which corresponded to significantly impaired insulin secretion (E). Islets isolated from the mice immediately following the OGTTs showed significantly increased insulin secretion under low glucose and significantly reduced insulin secretion under high glucose in CMPF injected mice relative to controls (F). (n=8 per group, p<0.05).
Figure 8:
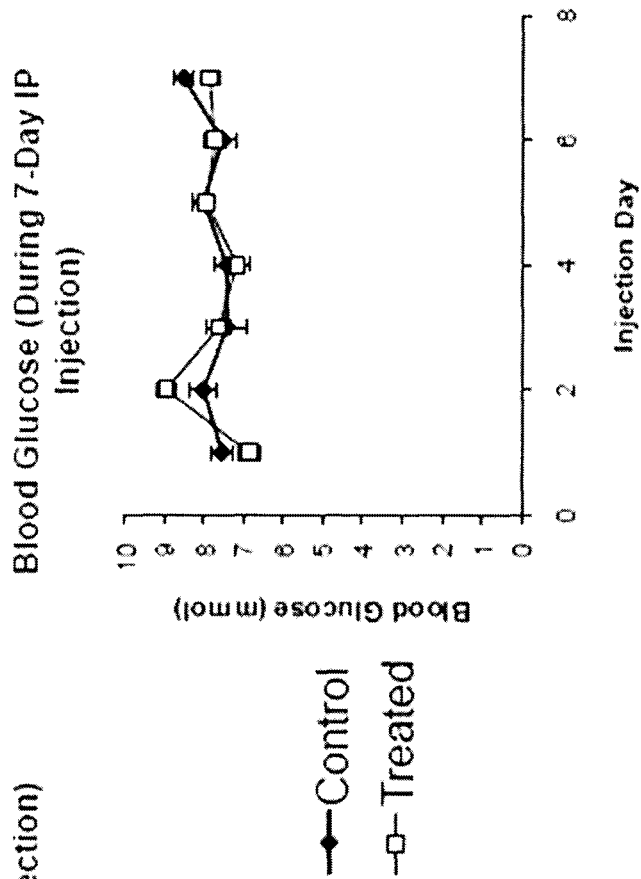
Figure 8:
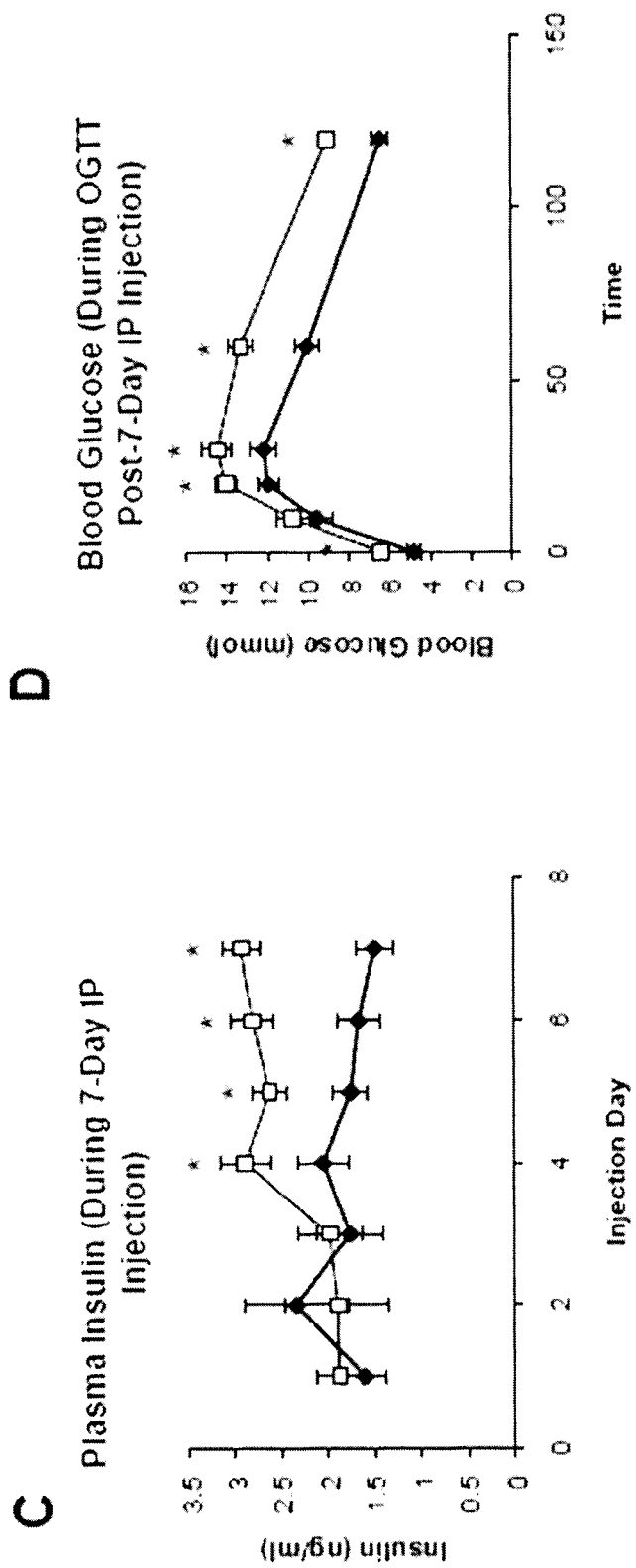
Figure 8:
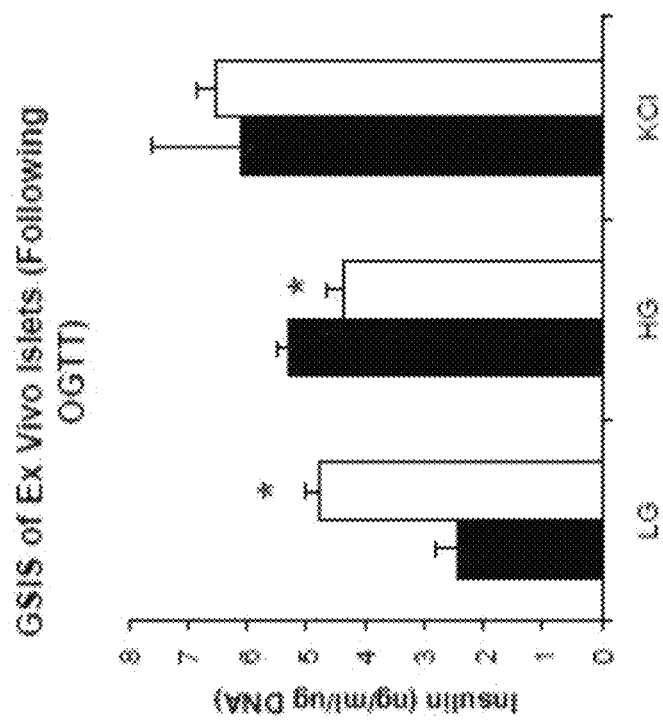
Figure 8:
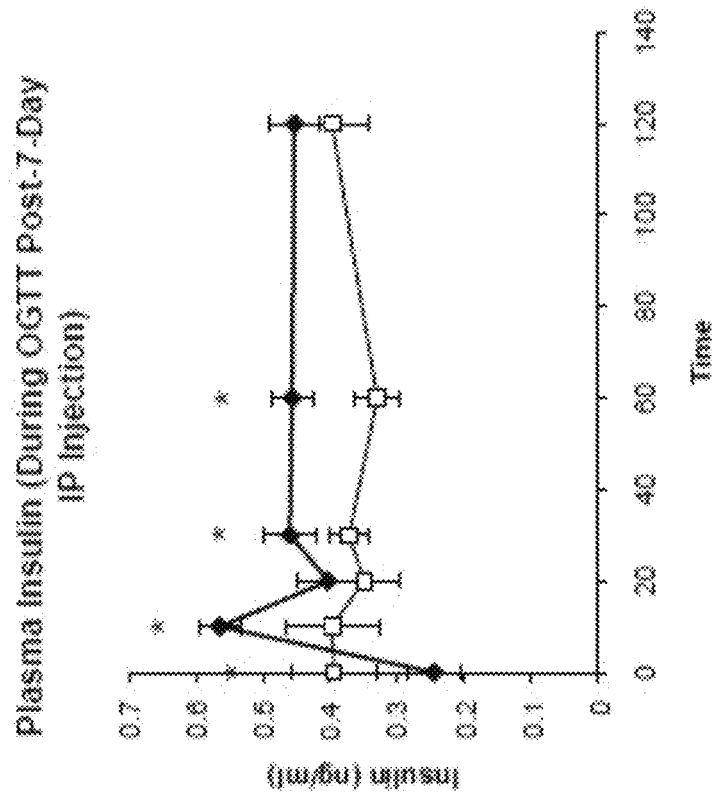
Figure 9:
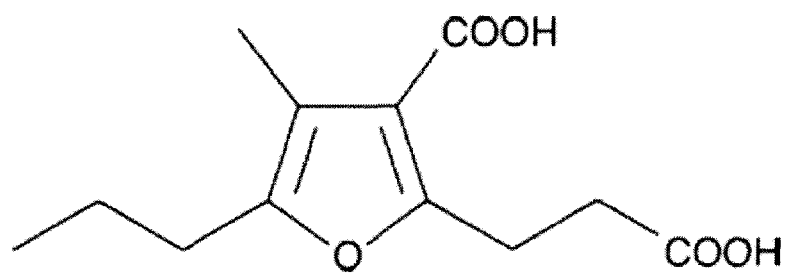
FIG. 9 shows the structure and molecular formula of 3-carboxy-4-methyl-5-propyl-2-furanpropanoic acid (CMPF). CMPF is found endogenously at concentrations of 20 μM in healthy individuals and in excess of 200 μM in uremic individuals.

The discovery that CMPF acts to impair beta cell function, combined with the significant elevation in plasma CMPF concentrations in GDM, IGT and T2D patients suggests that CMPF may play a causative role in the development of GDM and T2D. To investigate the effect of CMPF on glucose homeostasis, (FIG. 8C). The significantly increased plasma insulin levels together with no difference in blood glucose levels suggest that CMPF is inducing insulin resistance in treated mice as compared to controls. Following a 14 hr fast, CMPF injected mice had significantly higher blood glucose and significantly lower plasma insulin levels following three days of IP injection (FIG. 6C,D), while following seven days of IP injection, mice had both significantly higher blood glucose and plasma insulin levels, again suggestive of an insulin resistant phenotype (FIG. 8D). During the OGTTs, the CMPF injected group had significantly impaired insulin secretion at 10, 20 and 30 minutes post gavage, and significantly higher insulin secretion at 120 minutes compared to the vehicle control group after three days of IP injections (FIG. 6D). This impairment in insulin secretion corresponded to a significantly higher blood glucose at 30, 60 and 120 minutes post gavage. Following seven days of IP CMPF treatment mice had significantly higher blood glucose at 20, 30, 60 and 120 minutes post gavage (FIG. 8D), and this corresponded to significantly impaired insulin secretion at 10, 30 and 60 minutes post gavage compared to vehicle injected controls (FIG. 8E). Therefore, elevated plasma CMPF concentrations cause impaired beta cell function and prevent GSIS in vivo, resulting in glucose intolerance. Chronically elevated CMPF levels may also induce insulin resistance. Together these results suggest that CMPF may play a causative role in the pathogenesis of GDM and T2D.

Figure 3:
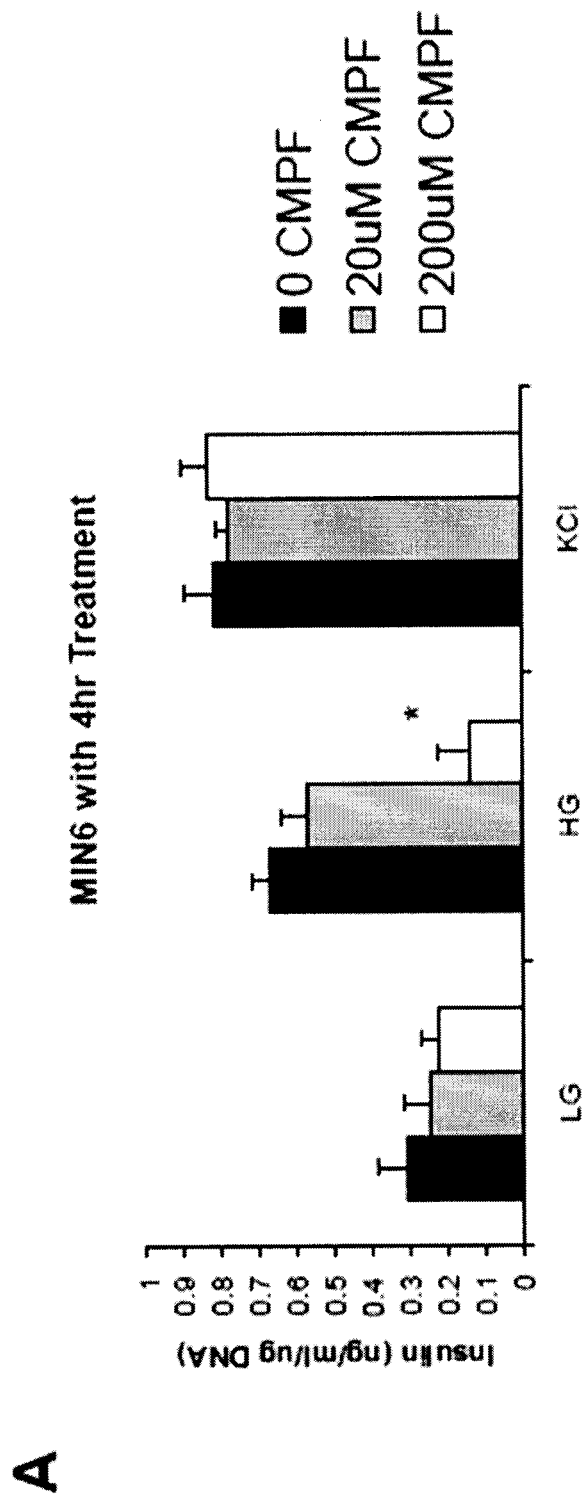
FIG. 3 shows that CMPF significantly impairs GSIS in MIN6 cells and intact primary human and murine islets. A) Treatment of MIN6 cells with either vehicle (0 CMPF, black) or 200 uM CMPF (white), shows that CMPF treatment significantly impairs GSIS and KCl-stimulated insulin secretion after a 4 hour pre-incubation (n=4). Treatment of primary human (B) and murine (C) islets with vehicle (0 CMPF, black), 20 uM CMPF (grey), or 200 uM CMPF (white) demonstrated that 200 uM CMPF impairs GSIS after 24 hour pre-incubation in both human and murine islets as compared to both vehicle and 20 uM CMPF controls (n=5 for human and n=4 for murine islets). LG=2.8 mM glucose, HG=16.7 mM glucose, KCl=16.7 mM glucose+30 mM KCl. *p<0.05.
Figure 3:
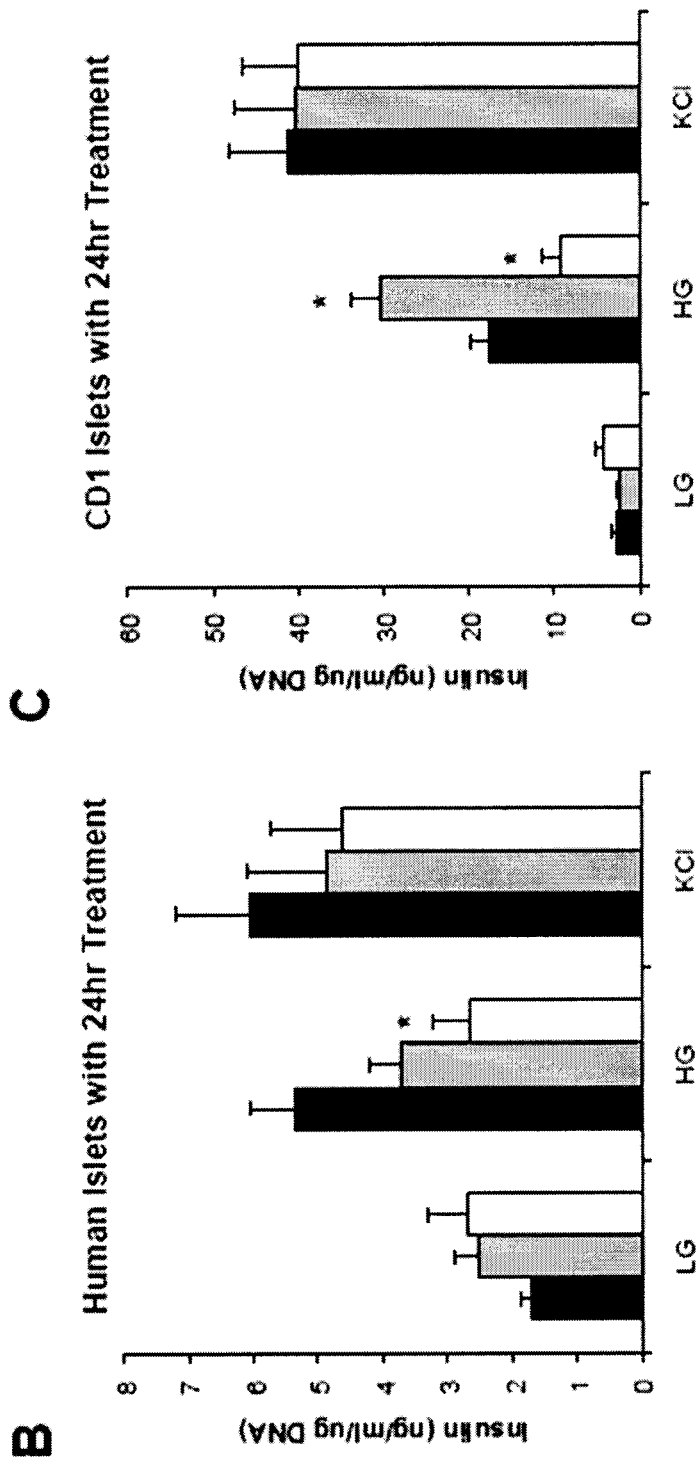
Figure 7:
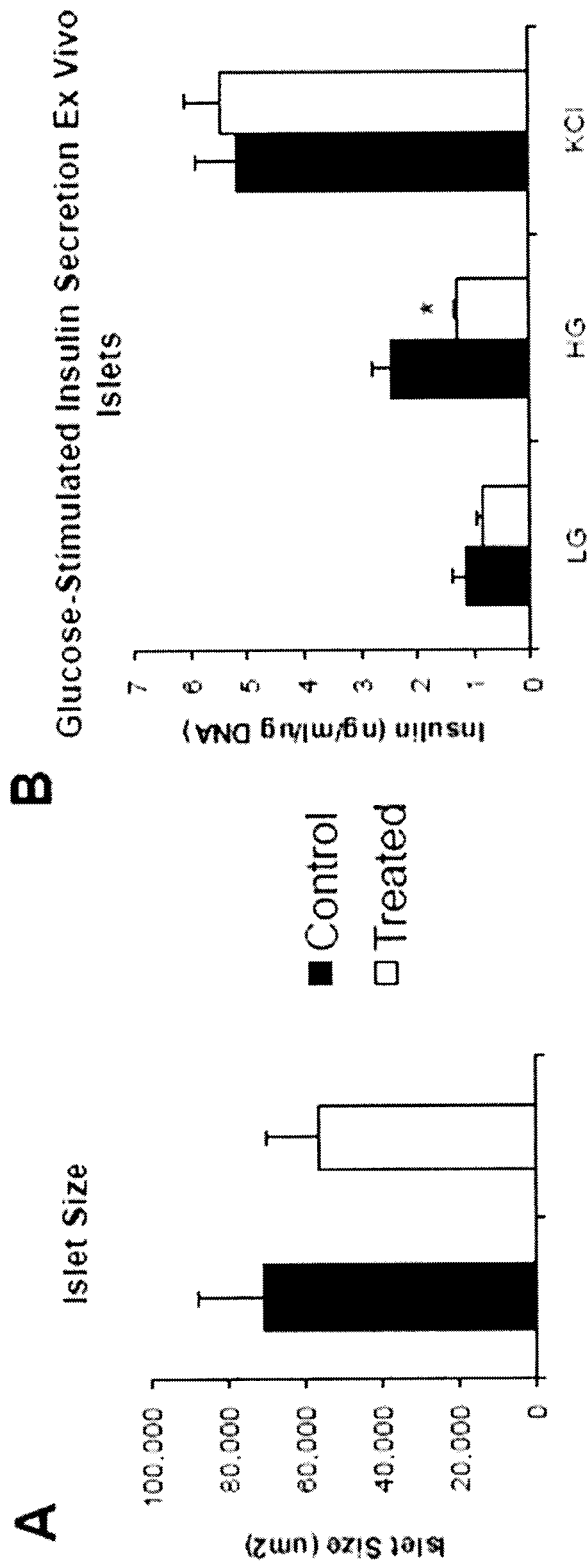
FIG. 7 shows that islets taken from mice injected IP with CMPF for 3 days show impaired GSIS, decreased total insulin content and decreased insulin mRNA. A) There is no significant difference in islet size between CMPF injected mice (Treated, white) and vehicle controls (Control, black). The islets do demonstrate impaired GSIS (B), decreased total insulin content (C) and decreased insulin mRNA (D), consistent with in vitro treatment of isolated primary islets. N=5, *P<0.05.
Figure 7:

To assess the effect of in vivo administration of CMPF directly on the beta cells, the islets were isolated from the 3-day and 7-day IP injected mice immediately following the OGTT. There was no significant difference in islet size between CMPF and vehicle control injected mice in either case, further validating that CMPF does not induce beta cell apoptosis (FIG. 7A, 3-day injected used as representative). Islets from mice treated with CMPF did however have significantly decreased GSIS (FIG. 7B) and lower total insulin content (FIG. 7C, 3-day injected used as representative), confirming the observed reduced insulin secretion during the OGTT. Interestingly, islets isolated from the 7-day CMPF injected mice had significantly elevated insulin secretion under low glucose stimulation as compared to vehicle-injected controls, validating the significantly higher basal plasma insulin levels observed following the 14 hour fast in vivo (FIG. 8F). The reduced total insulin content corresponded to lower insulin mRNA levels (FIG. 7D, 3-day injected used as representative), consistent with the in vitro studies described herein.

The significantly elevated levels of CMPF in the plasma of women with GDM, IGT, and a mixed population of T2D patients compared to NGT controls indicates that this compound may play an important role in the development of diabetes. This is supported by in vitro data in an immortalized beta cell line (MING) and isolated primary human and murine islets demonstrating that concentrations of CMPF observed in diabetic plasma impair GSIS after 24 hr incubation. This impairment of GSIS is not due to beta cell apoptosis or necrosis, but is likely caused by impairment of insulin biosynthesis (transcription and post-translational processing), and decreased capacity for glucose sensing, uptake and metabolism. Acute in vivo studies in mice show that CMPF impairs insulin secretion and causes glucose intolerance. Ex vivo evaluation of these islets demonstrate that there is no difference in islet size (indicating an absence of apoptosis), but a significantly reduced capacity for GSIS. Altogether, this suggests that CMPF may be an underlying cause of beta cell failure associated with GDM and T2D.

The fact that CMPF levels are significantly elevated in the plasma of women with GDM and patient with T2D indicate that CMPF is useful as an early biomarker in the prediction of GDM or T2D from a simple blood test without the use of GCTs or OGTTs, which are time-intensive and highly unpleasant for the patient. This would be especially useful in the diagnosis of GDM as HbA1c tests cannot be used. If CMPF is causally involved in the development of T2D, its levels would be expected to be elevated prior to a high HbA1c reading, allowing for medical intervention before the patient is exposed to an extended period of hyperglycemia.

At physiologically relevant levels observed in diabetic patients (200 uM) CMPF impairs GSIS and causes glucose intolerance in a relatively short period of time (3 days of IP injection), suggesting that CMPF is having a direct effect on the beta cell. The extra-pancreatic effect of insulin resistance is observed beginning at day four of IP CMPF injection, suggesting that CMPF is acting to directly impair beta cell function, as well as to increase insulin resistance in the peripheral tissues Therefore, inhibition of CMPF activity in pre-diabetic and diabetic patients with GDM or T2D may improve beta cell function and improve peripheral insulin sensitivity, and thus be a viable treatment of GDM and/or T2D.

EXAMPLE 2

Inhibition CMPF for the Treatment of β-cell Dysfunction

Figure 10:
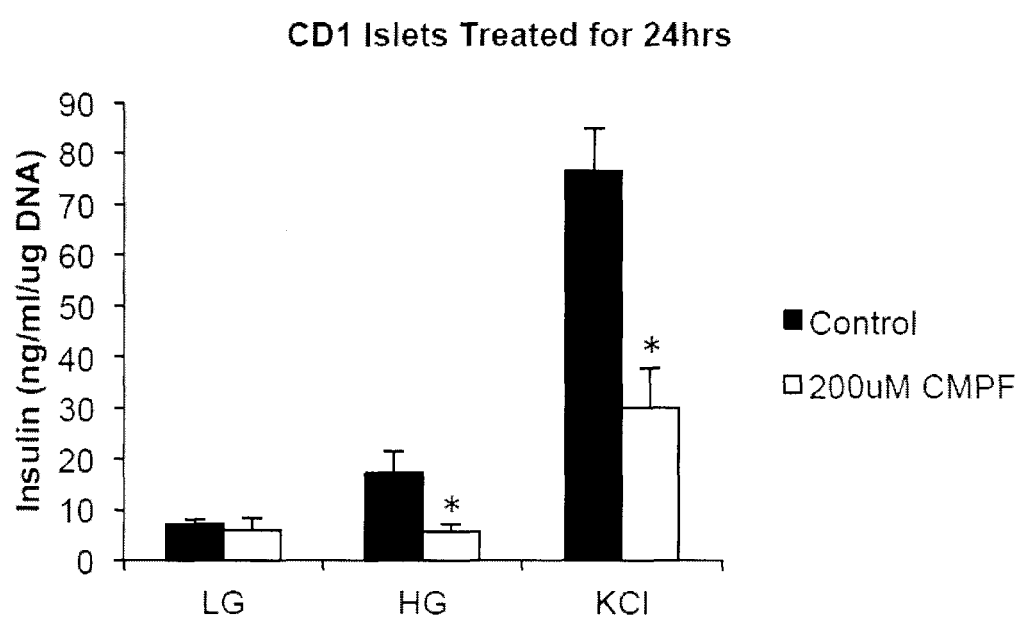
FIG. 10 shows that CMPF impairs beta cell function after 24 hours of treatment. CD1 mouse islets treated for 24 hours with 200 uM CMPF have significantly impaired glucose- and KCl-stimulated insulin secretion compared to vehicle treated controls.
Figure 11:
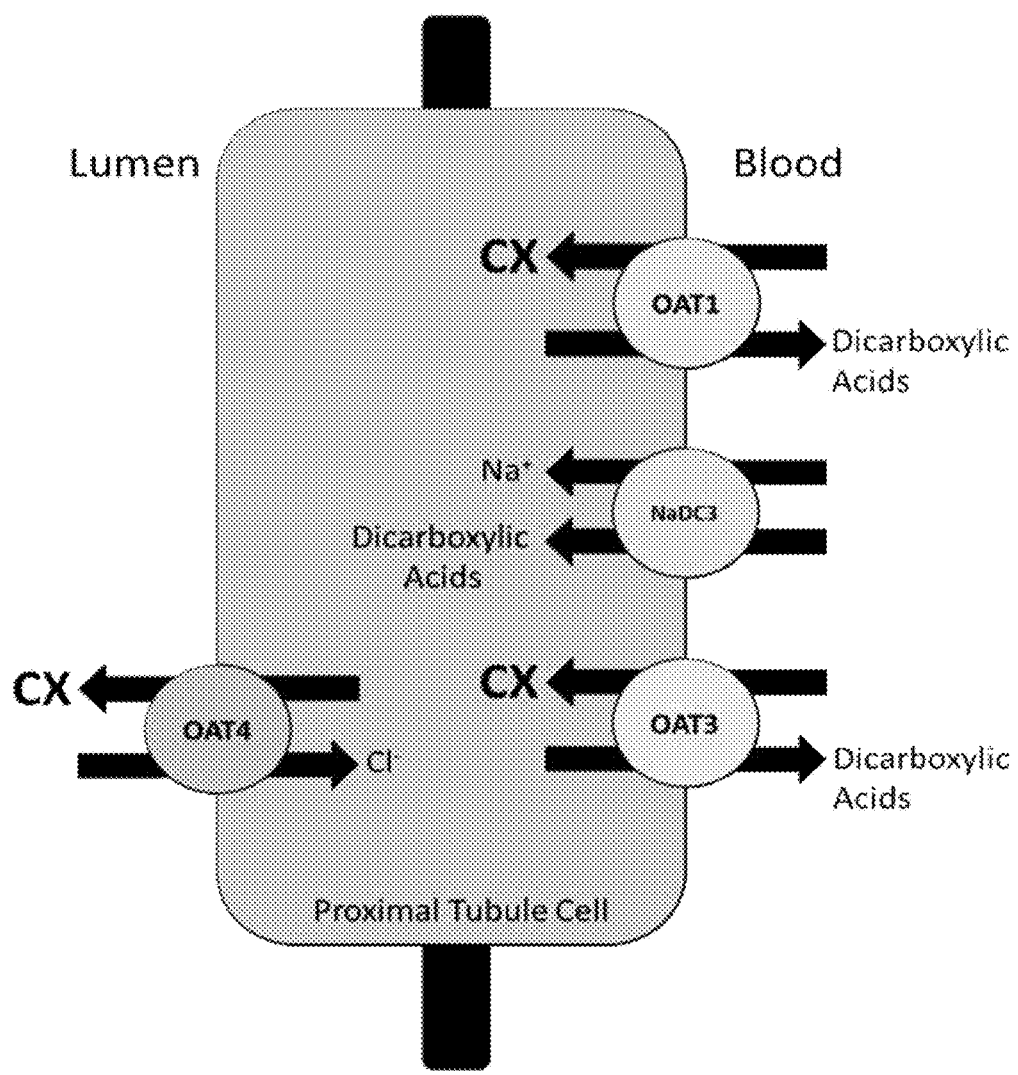
FIG. 11 shows that OAT1 and OAT3 function in CMPF transport into the kidney while OAT4 is responsible for secretion into the kidney lumen. OATs 1 and 3 function as exchangers, absorbing CMPF from the plasma into the proximal tubule cells of the kidney, and releasing dicarboxylic acids into the blood. The co-transporter NaDC3 replenishes dicarboxylic acid in the cells by transporting both dicarboxylic acids and sodium ions into the cells. Once CMPF is in the tubule cells, it is excreted into the kidney lumen by OAT4 in exchange for chloride ions.

As shown in Example 1 and FIG. 10, CMPF impairs beta cell function and whole-body glucose homeostasis at concentrations observed in the plasma of gestational and type 2 diabetic patients. Initially identified as a potential uremic toxin, the majority of research done with CMPF has been focused on identifying its interaction with the kidney. Fairly recent studies have identified two organic anion transporters, OAT1 (SLC22A6) and OAT3 (SLC22A8), which are responsible for the transport of CMPF from the plasma to the proximal tubule cells of the basolateral membrane, and a third, OAT4 (SLC22A11), which is responsible for excretion of CMPF in the urine (Deguchi et al., 2005) (FIG. 11). The OATs function as organic anion exchangers, transporting one anion molecule into the cell and simultaneously transporting one endogenous dicarboxylic acid out of the cell (Sekine et al., 2006). The presence of endogenous dicarboxylic acids within the cell is therefore critical for OAT function, thus they are expressed along with a sodium-dicarboxylate co-transporter, NaDC3 (SLC13A3), which functions to transport dicarboxylic acids back into the cells (FIG. 11).

Effect of CMPF on GSIS

Figure 12:
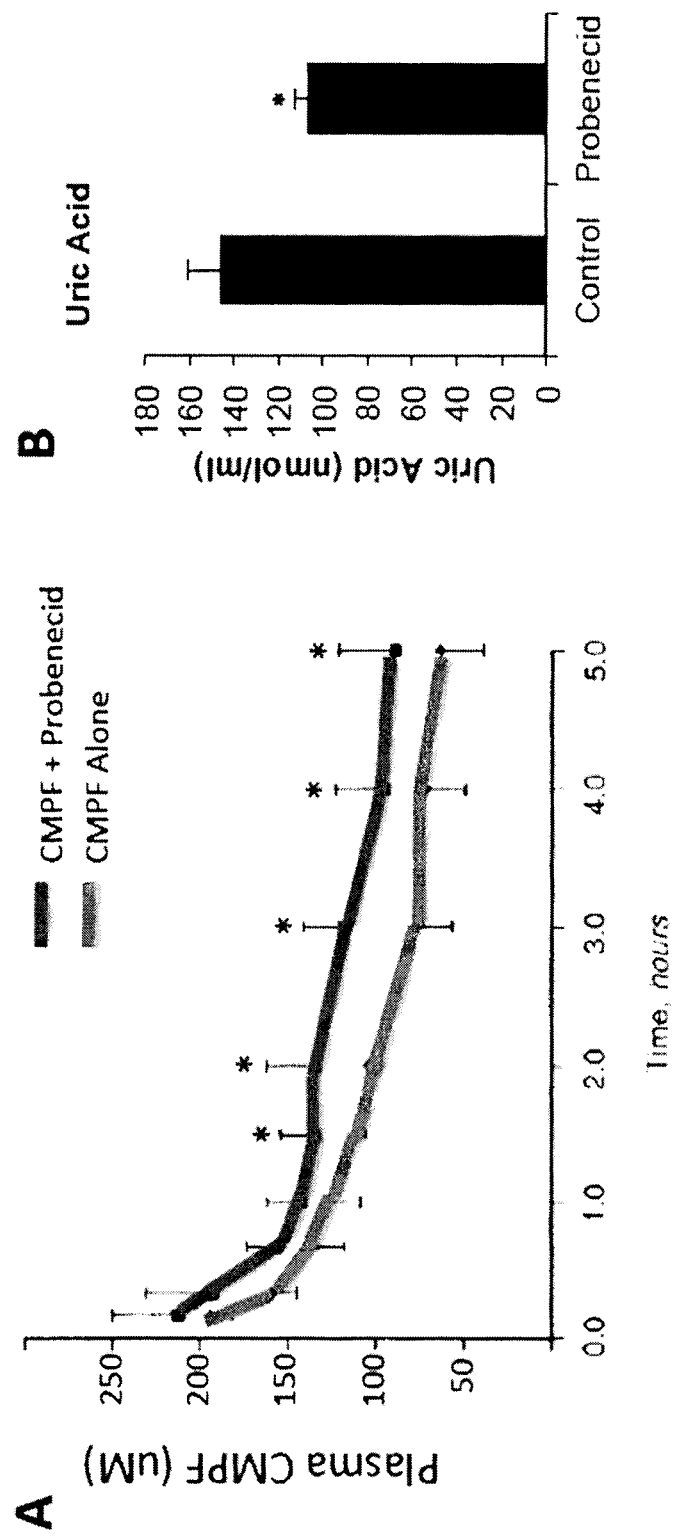
FIG. 12 shows that probenecid blocks OAT transporter function in vivo. Panel (A) is adapted from Costigan et al. 1996 and shows CMPF is cleared from the plasma when 5 mg/kg is administered alone (light grey). When CMPF is co-administered with 150 mg/kg probenecid, its clearance is significantly reduced over time. Panel (B) shows that twice daily injections of 150 mg/kg probenecid in mice inhibits OAT transporter function, as evidenced by significantly reduced plasma uric acid concentrations.

Studies using OAT-specific inhibitors probenecid, p-aminohippurate (PAH) and benzylpenicillin (PCG) have demonstrated that by blocking both OAT1 and OAT3 the secretion of CMPF can be completely inhibited in vivo (Deguchi et al., 2005). Probenecid is a competitive inhibitor of the OATs and acts by preferentially binding the transporters, preventing CMPF and other OAT ligands from transporter binding. In the treatment of gout, Probenecid prevents the re-uptake of uric acid from the urine into the proximal tubules by preventing uric acid binding to OAT4 (a homolog of OAT1 and OAT3 located on the luminal side of proximal tubule cells), limiting the amount of uric acid being returned to the blood supply and thus eliminating gout (Mason, 1954). When given in addition to antibiotics, Probenecid prolongs the circulation of antibiotics in the blood stream by preventing their uptake into the kidneys via OAT1 (Butler, 2005). Administration of probenecid causes a reduction in the clearance of CMPF, resulting in accumulation of CMPF in the plasma (Costigan et al., 1996) (FIG. 12A). Significantly lower uric acid levels in the plasma of probenecid-treated mice, indicating that its re-uptake through OAT transporters is impaired, further support blockage of OAT transporter activity (FIG. 12B). Using concentrations of PCG that selectively inhibit OAT3, it has been shown that 65-75% of CMPF secretion was prevented, indicating that this is the primary transporter of CMPF in the kidney (Deguchi et al. 2005).

OAT Transporters in the Kidney

The expression of OAT transporters is significantly reduced in the kidneys in rodent models of T2D (Mishra et al., 2004). In the db/db mouse model of T2D, both the OAT3 and OAT1 transporters have significantly reduced expression by microarray (Mishra et al., 2004; More et al., 2012). This finding suggests that CMPF levels may be elevated in the plasma of GDM and T2D patients due to a down-regulation of expression of its transporter in the kidney, thus limiting its ability to be secreted in the urine. This hypothesis is consistent with the observed increase in plasma levels of CMPF during kidney failure and uremia. Under these physiological conditions OAT1, 3, 4 and NaDC3 have all been reported to have significantly decreased expression in the kidney (Deguchi et al. 2005)

Figure 13:
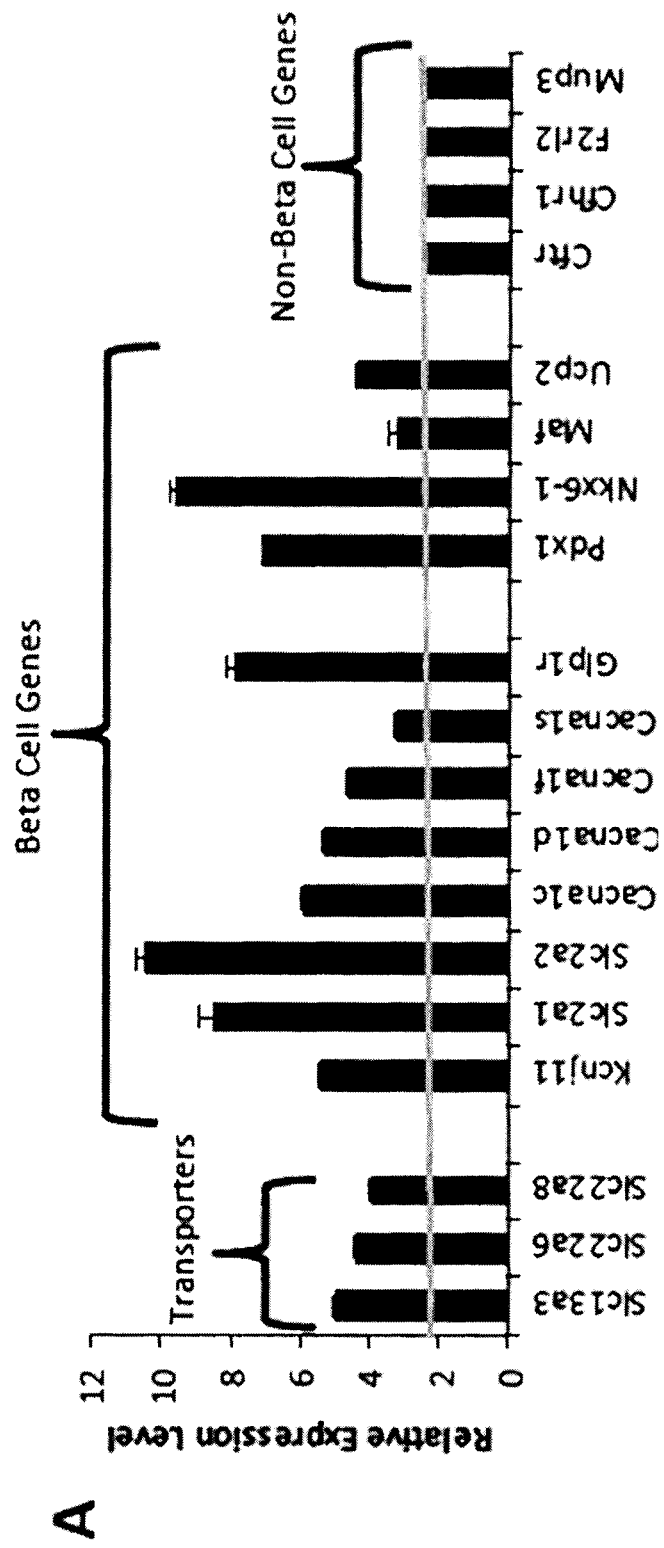
FIG. 13 shows that the OAT transporters and co-transporter are expressed in the pancreatic islet cells. In panel (A) OAT1, OAT3 and NaDC3 are expressed in the mouse islet at levels comparable to other islet genes. Panel (B) shows that OAT3 and NaDC3 are predominantly expressed in insulin-producing cells, while OAT1 and OAT4 are predominantly expressed in noninsulin producing human islet cells. C) Expression of OAT1, OAT3 and NaDC3 is confirmed in human islets by western blotting. The human proximal tubule cell line HK-2 was used as positive control.
Figure 13:
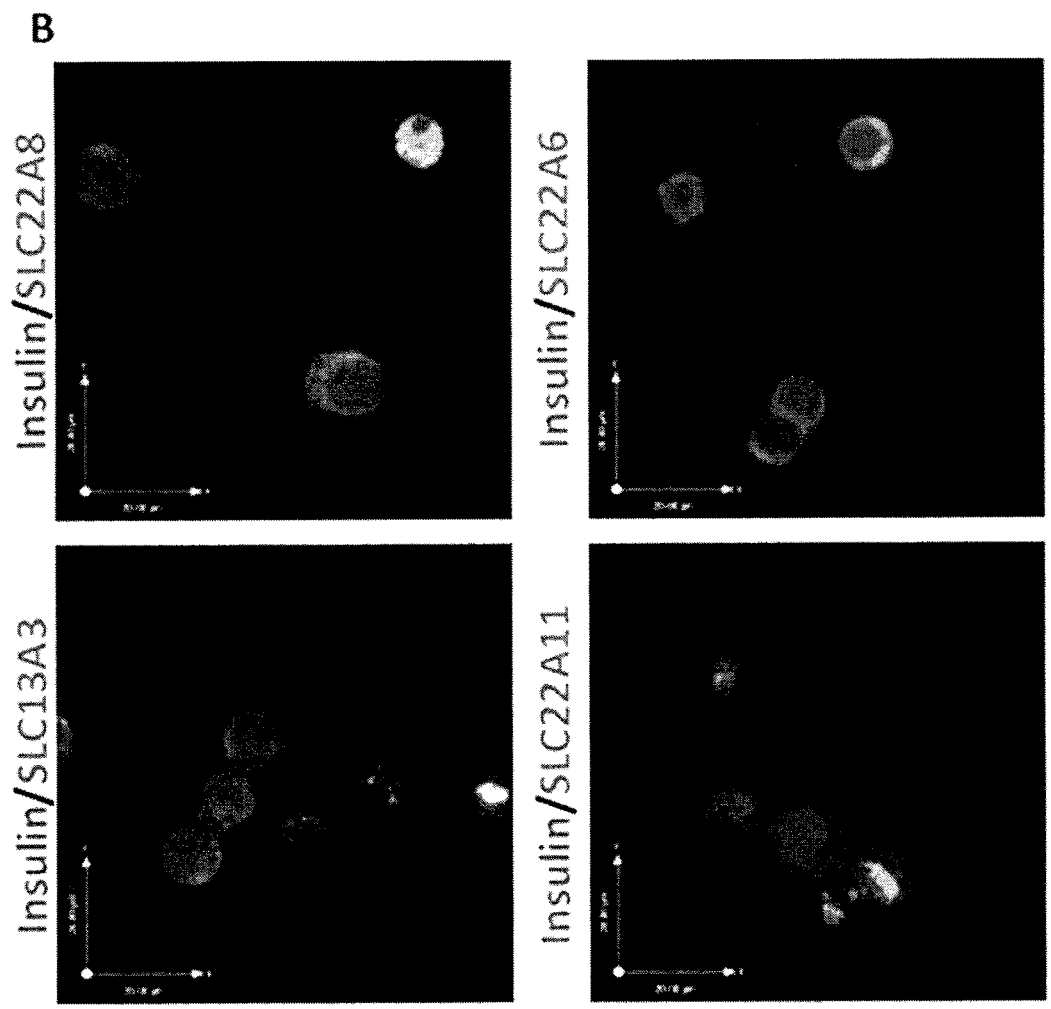
Figure 13:

Blockage of OAT Transporter Function Causes Increased Plasma CMPF Concentrations in Mice The present description provides an unexpected link between OAT1, OAT3, NaDC3 or OAT4 and diabetes. Microarray data of normal glucose tolerant (NGT) mouse and human islets shows strong expression of OAT1, OAT3 and NaDC3 in relation to other proteins known to be expressed in the islet (Mouse islets as representative, FIG. 13A). There is no mouse equivalent of OAT4. This expression profile is further supported by transcriptome analysis of purified human beta cells, mouse islets, and mouse- and rat-derived beta cell lines all showing relatively strong expression of OAT1, 3 and NaDC3 (Kutlu et al. 2009). The finding that these transporters are expressed in the pancreatic islets was further validated in human islets using immunofluorescent staining and western blotting as shown in FIG. 13B,C. Interestingly, the primary CMPF transporter OAT3 and the co-transporter NaDC3 show the strongest staining in insulin expressing (beta) cells, while OAT1 and OAT4 show stronger staining in non-insulin positive cells (presumably alpha, delta, and epsilon cells) (FIG. 13B). By western blot, strong bands corresponding to OAT1, OAT3, OAT4 and NaDC3 are found in human islets and the human proximal tubule cell line HK-2. Studies examining the transcriptome of T2D islets show significantly increased expression of OAT1 and OAT3 in T2D islets compared to healthy controls (Dominguez et al., 2011). It is therefore possible that enhanced OAT1 and OAT3 expression in the pancreatic beta cells is increasing CMPF transport into the beta cells in T2D, thus facilitating CMPF-mediated beta cell dysfunction.

OAT Transporters are Expressed in Pancreatic Islet Cells.

Figure 14:
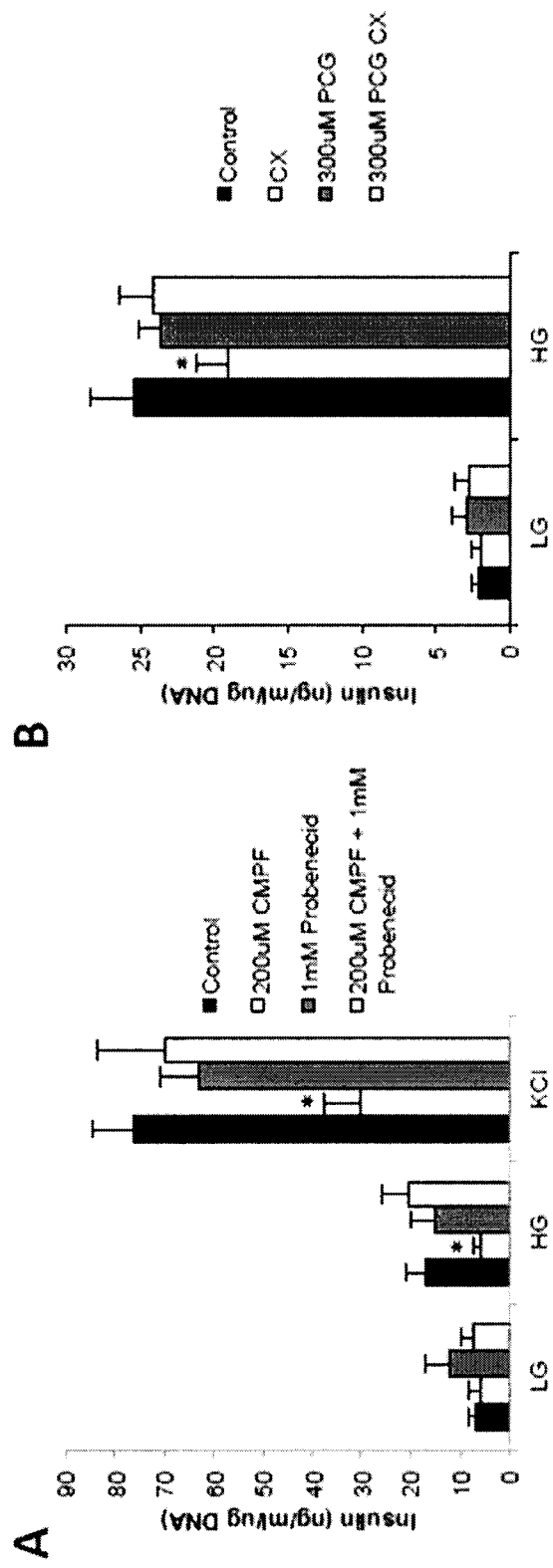
FIG. 14 shows that Inhibition of the OAT transporters blocks CMPF-inhibition of beta cell function. Panel (A) shows that pre-treatment of islets with 1 mM Probenecid prior to 24 hour treatment with 200 uM CMPF preserved insulin secretion in isolated mouse islets. Panel (B) shows that pre-treatment of islets with 300 uM of the OAT3-specific blocker PCG prior to 24 hour treatment with 200 uM CMPF preserved glucose-stimulated insulin secretion in isolated mouse islets.

To determine if the OAT transporters are responsible for CMPF transport into beta cells, CD1 mouse islets were pre-treated 1 mM Probenecid prior to the addition of CMPF to ensure blockage of the channels and complete exclusion of CMPF from the cells. A dosage of 1 mM Probenecid was selected based on previous evidence that this concentration was sufficient to inhibit anion transport from beta cells without any observed effect on glucose-stimulated insulin secretion (Arkhammar et al. 1989). Islets were pre-treated with 1 mM Probenecid for 3 hours prior to the addition of 200 uM CMPF. After 24 hours cells were assessed by GSIS. Treatment with 200 uM CMPF alone produced a significant decrease in GSIS under both high glucose and KCl-stimulated conditions, consistent with previous findings, while treatment with 1 mM Probenecid for 27 hours had no effect on GSIS compared to vehicle controls. Treatment of islets with 1 mM probenecid in addition to 200 uM CMPF (CMPF+P) completely abolished the effect of CMPF on the islets (FIG. 14A). CMPF+P treated islets exhibited high-glucose and KCl-stimulated insulin secretion equal to that of vehicle-treated controls. Therefore, probenecid inhibits the effect of CMPF. Similar results were obtained using the OAT3-specific inhibitor PCG. Islets were again pre-treated for 3 hours with 300 uM PCG prior to 24-hour 200 uM CMPF treatment (FIG. 14B). CMPF alone was able to significantly inhibit insulin secretion under high glucose stimulation, while 300 uM PCG had no significant effect. Treatment with 300 uM PCG and 200 uM CMPF inhibited the effect of CMPF, resulting in control levels of insulin secretion.

Inhibition of the OATs Blocks CMPF-Inhibition of Beta Cell Function

Figure 15:
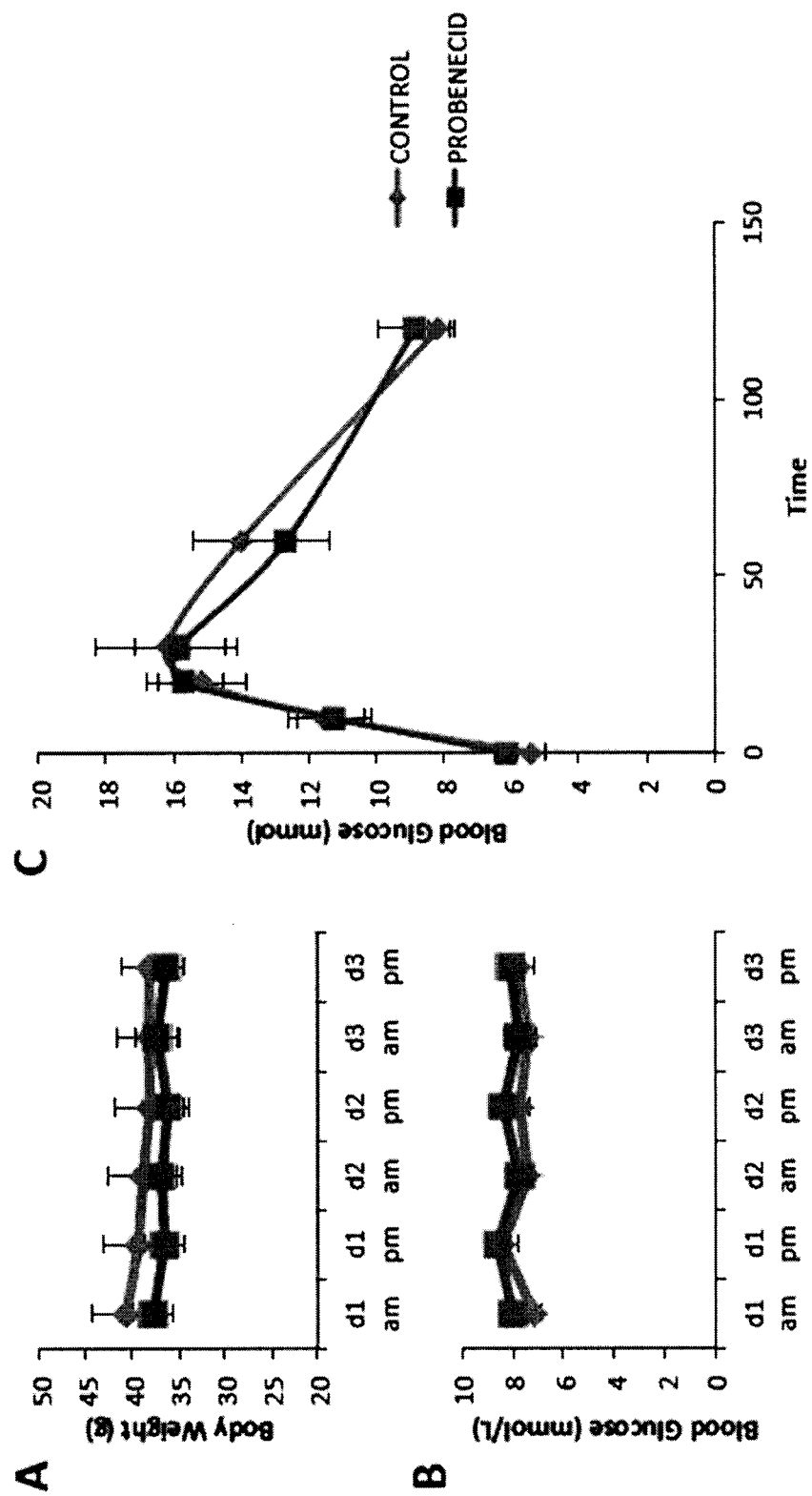
FIG. 15 shows that Probenecid in vivo has no effect on glucose tolerance. Mice injected with 150 mg/kg probenecid twice daily for 3 days had no difference in (A) body weight or (B) blood glucose. Panel (C) shows an OGTT was performed on day 4 and showed no difference in glucose tolerance between vehicle controls and probenecid-injected mice.

While administration of Probenecid elevates circulating CMPF levels, this does not alter glucose tolerance, suggesting that CMPF alters beta cell function in vivo through the OATs. Mice were injected IP with 150 mg/kg probenecid twice daily for 3 days as previously described (Baudoux et al., 2012). No differences were observed in body weight or fasting blood glucose (FIG. 15A,B). On the 4th day, a 2 g/kg OGTT was performed and showed no significant difference in glucose tolerance (FIG. 15C). As 3 days of CMPF-treatment alone was able to induce glucose intolerance, probenecid appears to block the activity of CMPF on the beta cell.

EXAMPLE 3

Characterization of the Effects of CMPF on Beta Cell Function

Gestational diabetes (GDM), a condition with serious health implications for mother and child, results from failure of the beta-cells to adapt to increased metabolic demands. The cause of GDM and the extremely high rate of progression to type-2 diabetes (T2D) remain unknown. As shown in Example 1, the furan fatty acid metabolite CMPF is remarkably elevated in the plasma of humans with GDM, T2D and pre-diabetes. In mice, diabetic-levels of CMPF induced glucose intolerance, impaired glucose-stimulated insulin secretion and decreased glucose utilization. Here, the inventors show that CMPF enters the beta-cell through a novel transport mechanism to be metabolized, resulting in impaired mitochondrial function, oxidative stress, dysregulation of key beta-cell transcription factors PDX1 and FOXO1, and ultimately reduced insulin biosynthesis. Importantly, CMPF-induced beta-cell dysfunction could be prevented by specifically blocking its transport or through anti-oxidant treatment.

Materials and Methods

Hyperinsulinemic Euglycemic Clamps

Hyperinsulinemic euglycemic clamps were performed as previously described (Liu et al., 2012) following 7 days of IP injections with either CMPF or vehicle. Internal and external cannulation was performed on day 3 of the injection protocol.

Gene Expression

Total RNA was extracted from 24 hour vehicle or CMPF-treated islets using the Qiagen RNeasy Plus mini kit (Hilden, Germany). Microarray analysis was performed as previously described (Basford et al. 2012) using the Affymetrix Mouse 430 2.0 Gene Chip at the University Health Network microarray center (Toronto, Canada). Significant changes were defined as $P<0.05$. Microarray data will be available on the NCBI GEO database at the time of publication. Human islet microarray data can be found at GE040709. Reverse transcription from total RNA and quantitative real time PCR (qPCR) analysis was performed as previously described (Basford et al. 2012). Primers were designed using Primer3 software (NCBI). Data were normalized to beta actin mRNA.

ROS Accumulation and Islet Size in Isolated Islets

The level of superoxide and $H_2O_2$ were determined using mitoSOX red and 2',7'-dichlorodihydro fluorescein diacetate (CM-$H_2$-DCFDA) respectively (Molecular Probes, Invitrogen, Canada) in isolated islets treated with either vehicle control or 200 µM CMPF for 4 or 24 hours, as previously described (Lee et al. 2009). Bright field images were used to determine islet size.

Mitochondrial Membrane Potential (MMP)

Dispersed isolated islets were treated with either vehicle control or 200 µM CMPF for 24 hours prior to loading with rhodamine 123 (25 ug/ml, 10 min) in 2.8 mM glucose imaging buffer. 5 mM $NaN_3$ was added to fully depolarize the MMP (Diao et al., 2008).

Western Blotting

CMPF-treated and control mouse islets were lysed in RIPA buffer (Cell Signaling, Danvers, Mass., USA) containing protease inhibitor cocktail (Roche, Mississauga, ON, Canada). Lysates were spun at 12,000 rpm and supernatant was loaded onto a 4-15% SDS-PAGE gradient gel (BioRad, Mississauga, ON, Canada) and transferred onto PVDF membrane using a Turbo Blotter (BioRad). The membrane was probed with the corresponding antibodies, and imaged using Kodak Imager 4000pro (Carestream, Rochester, N.Y., USA).

Immunofluorescent Staining

The cellular localization of FOXO1 and PDX1 were determined in dispersed CD1 mouse islet cells using immunofluorescence. The presence of the organic anion transporters (OATs) were determined in dispersed human islet cells also using immunofluorescence. Staining was performed as previously described (Diao et al., 2008). Images were acquired using a confocal microscope (Quorum Wave FX Spinning Disc; Perkin Elmer, Waltham M L, USA) and Volocity software (Perkin Elmer).

Results

CMPF Reduces Whole-body Glucose Utilization

Figure 16:
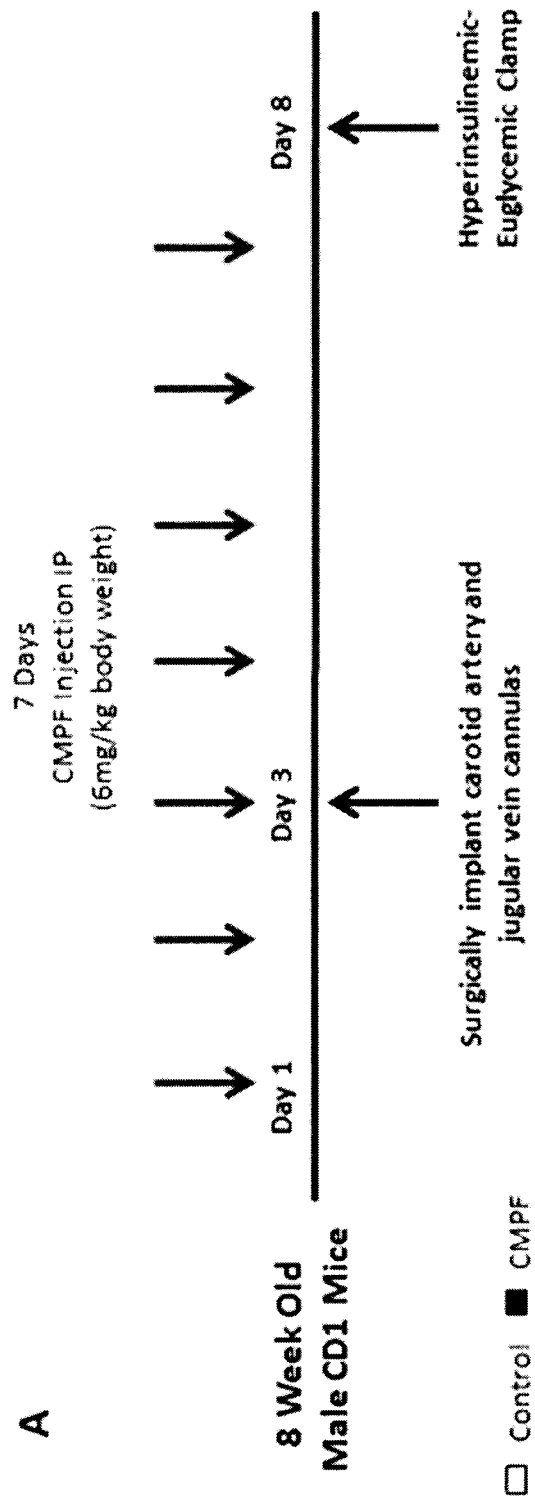
FIG. 16 shows that after 7 days of CMPF injection, mice have reduced glucose utilization based on hyperinsulinemic-euglycemic clamps. A) Schematic illustrating injection and surgical timeline. B) Glucose infusion rate (C) glucose appearance and (D) disappearance rates and (E) glycolytic rate in 7 day CMPF-injected mice compared to vehicle controls (N=4/group). No difference in the post/basal glycolytic rate suggests that CMPF does not induce insulin resistance, but instead decreases glucose appearance and disappearance rates. $P<0.01$, *$P<0.001$. Values mean±SEM.
Figure 16:
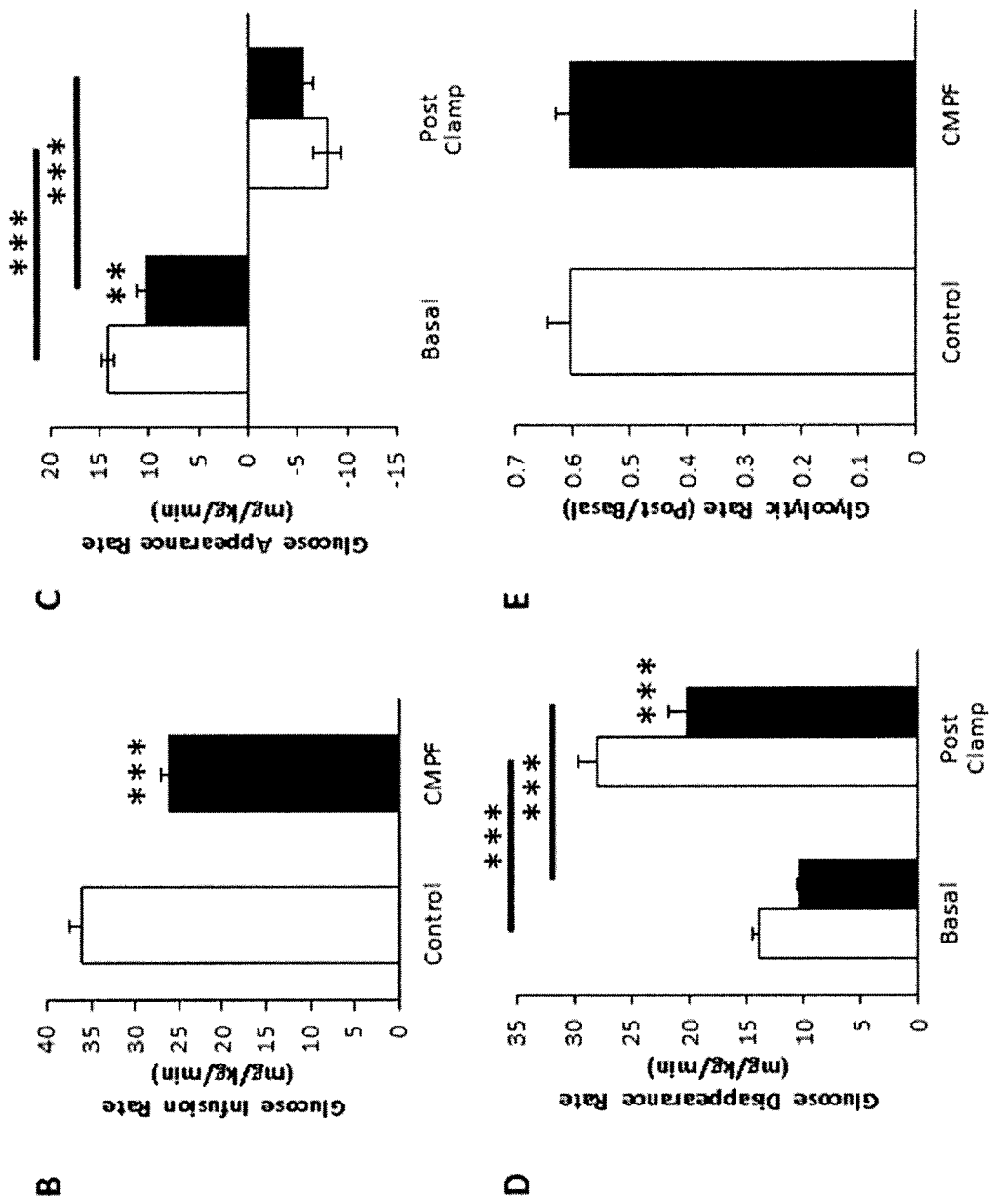

As shown in Example 1, elevated plasma CMPF results in glucose intolerance and impaired insulin secretion. Interestingly, despite defective GSIS, seven-day CMPF treatment was associated with fed-state hyperinsulinemia and hyperglucagonemia. Despite elevated insulin levels, no significant difference in insulin sensitivity was observed between CMPF and vehicle-treated mice by insulin-tolerance testing (ipITT). To more thoroughly examine integrated glucose homeostasis, hyperinsulinemic euglycemic clamps were performed. As shown in FIG. 16, though there is a significant reduction in the glucose infusion rate (FIG. 16b), the overall glycolytic rate indicates that there is no difference in the response to insulin (post clamp/basal) (FIG. 16e). Therefore, the difference in glucose infusion is due to significantly lower glucose appearance basally (FIG. 16c), and significantly reduced insulin appearance post-clamp (FIG. 16d). 7 days of CMPF treatment does not induce insulin resistance, but reduces whole body glucose utilization.

CMPF is Metabolized to Increase ROS

Figure 17:
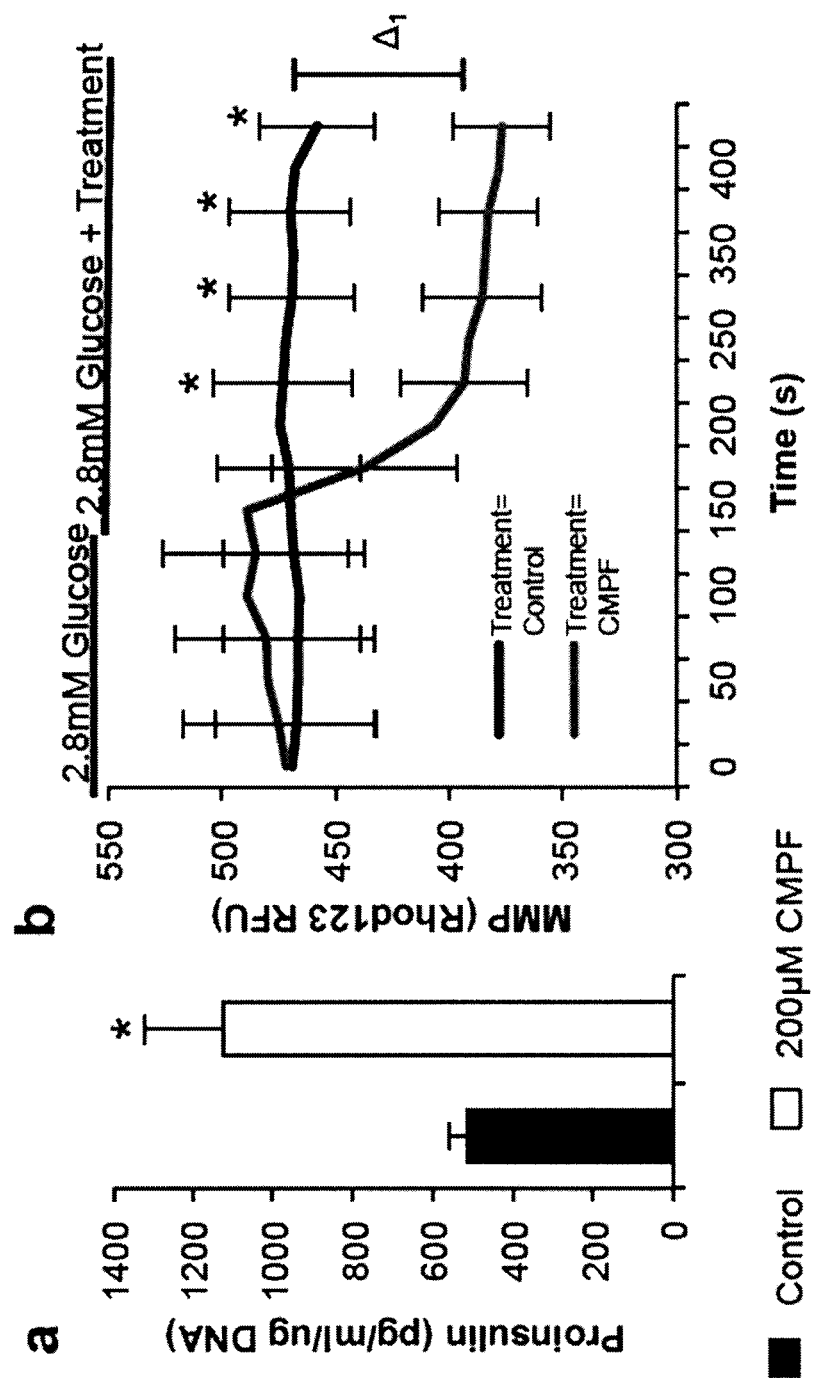
FIG. 17 shows that CMPF is metabolized by beta-cells to increase ROS and alter insulin biosynthesis. A) Proinsulin in the media of 24 hr treated islets (n=4/group). B) Mitochondrial membrane potential (MMP) following acute addition of vehicle control or 200 μM of CMPF (N=3/group). C) ROS levels in 4- and 24-hour treated mouse islets with representative images (N=10-15 islets/mouse from 4 mice/group). D) Expression of antioxidant genes Cat and (e) Ucp2 (n=4/group). F) ROS accumulation in 24 hr-treated islets treated with 500 μM NAC (n=10 islets/mouse from 4 mice/group). G) GSIS and (h) total insulin content from 24 hr-treated islets co-treated with 500 μM NAC (n=4/group). Western blots showing (i) Ser9 phosphorylation of GSK3β, (j) Ser473 phosphorylation of AKT (n=3/group). K) Immunofluorescent staining showing nuclear translocation of FOXO1 and (l) PDX1 with CMPF and NAC treatment (n=3-6). Quantification of nuclear percentage of (m) FOXO1 and (n) PDX1 based on immunofluorescent staining with CMPF and NAC treatment. O) Western blots showing protein abundance of PDX1 and FOXO1. Values are mean+/−SEM. Student's t-test (a, c-j, m-o), one-way ANOVA (b). *$P<0.05$, $P<0.01$, *$P<0.001$.
Figure 17:
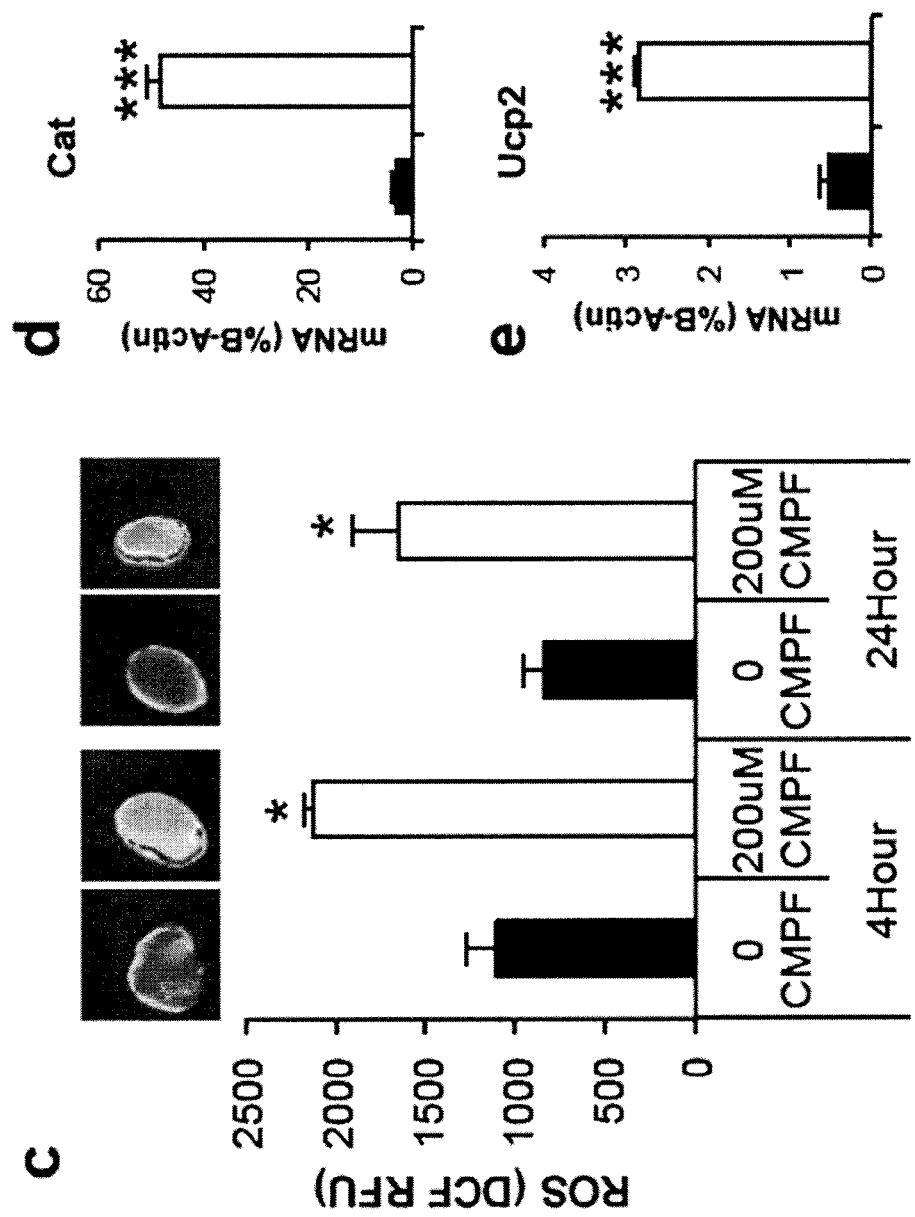
Figure 17:
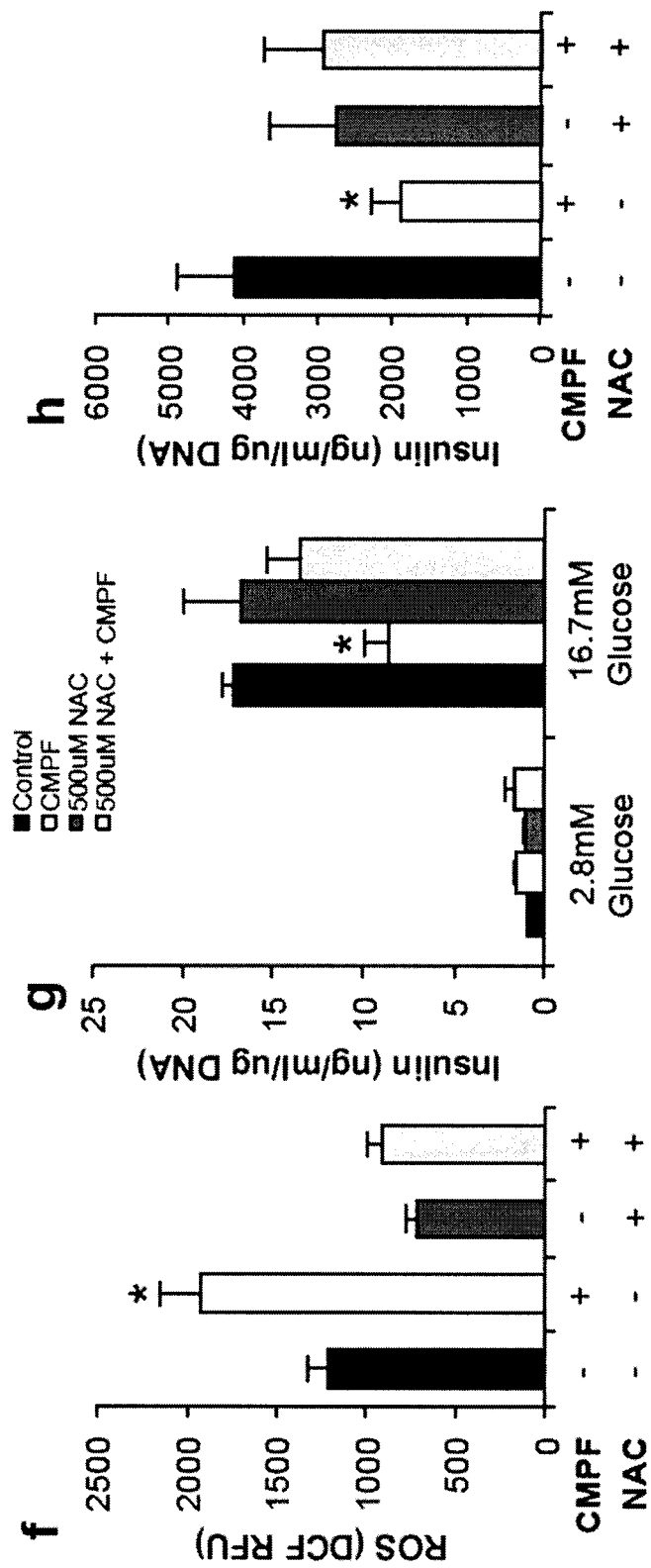
Figure 17:
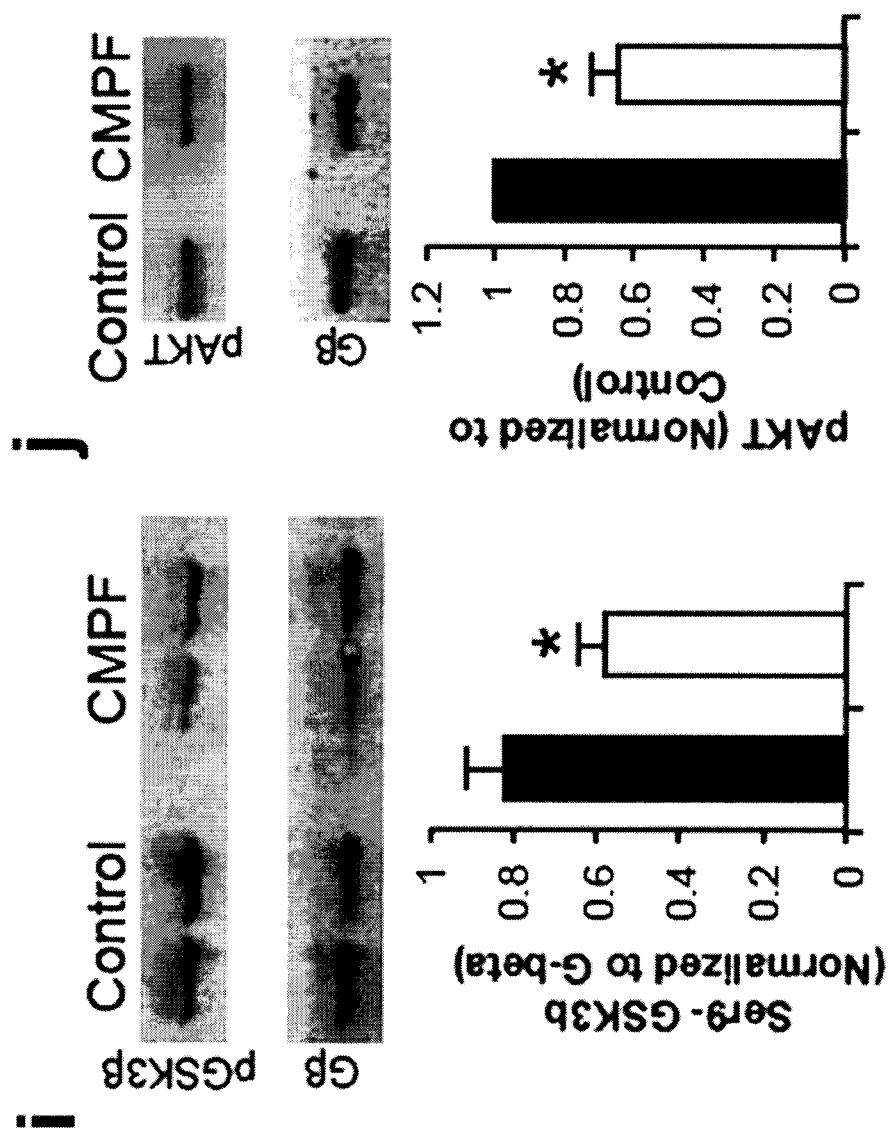
Figure 17:
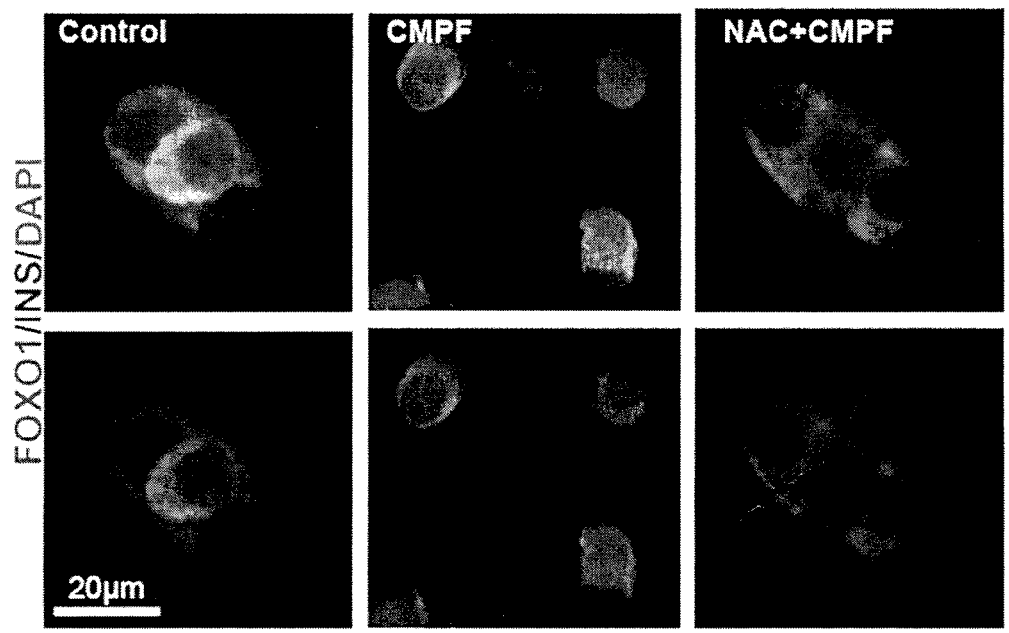
Figure 17:
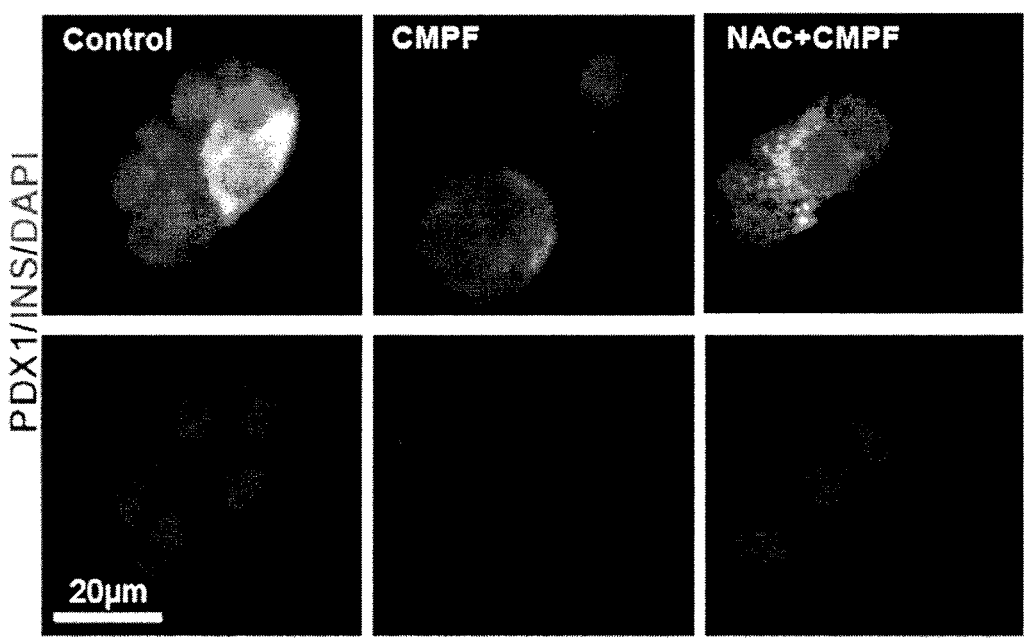
Figure 17:
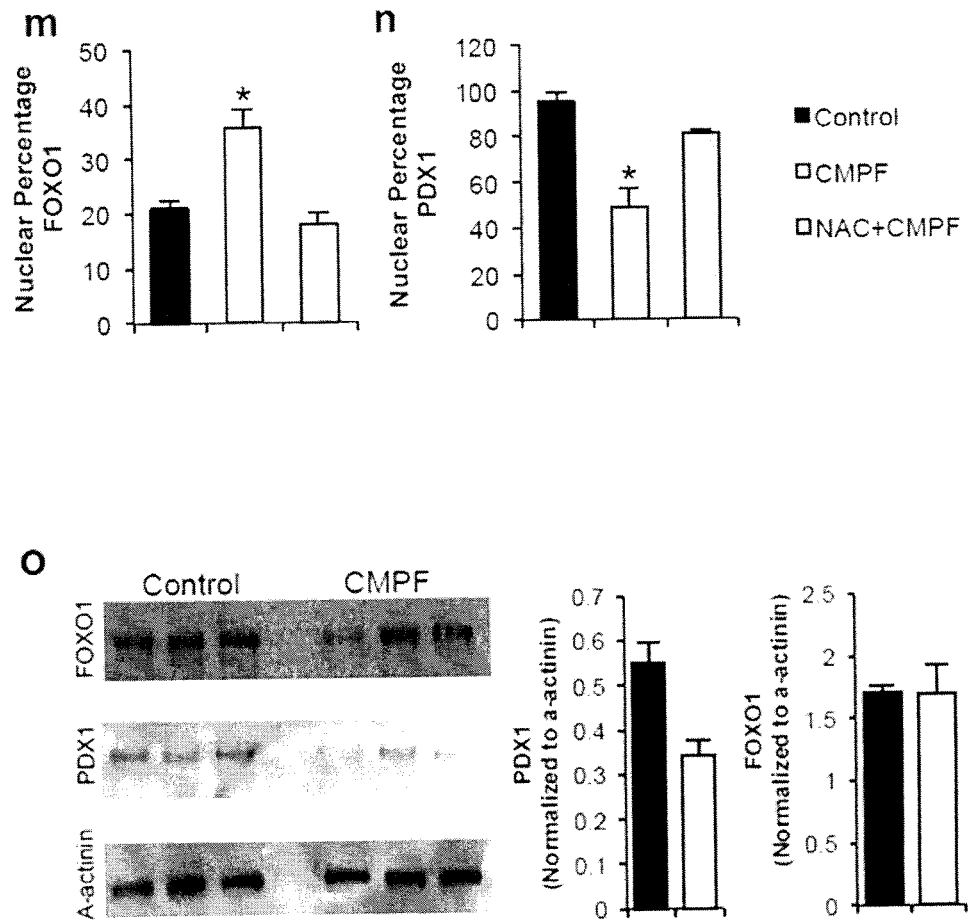

Lower total insulin content may be due to beta-cell exhaustion caused by over-stimulation and/or defective insulin production. To determine the mechanism through which CMPF diminishes insulin content, we measured insulin in the media following 24 hr treatment. There was no difference in accumulation of total insulin (data not shown), however there was substantially more proinsulin in the media of CMPF-treated islets compared to controls, consistent with an altered proinsulin:insulin ratio observed in T2D patients (Kamoda et al. 2006) (FIG. 17a). Impaired insulin processing has previously been associated with elevated levels of the mitochondrial protein uncoupling protein 2 (UCP2) (Kashemsant and Chan, 2006). Excess substrate for the electron transport chain leads to the formation of ROS, which can induce UCP2 expression. To first determine if CMPF is metabolized by beta-cells, we measured changes in mitochondrial membrane potential (MMP) in mouse islets acutely treated with CMPF. CMPF caused a transient membrane hyperpolarization consistent with an increase in proton motive force generated through beta-oxidation (FIG. 17b). This corresponded to a 2-fold increase in ROS in CMPF-treated islets over controls after 4 and 24 hrs of treatment (FIG. 17c). Increased antioxidant gene expression, including Ucp2 and catalase (Cat) after 24 hrs of CMPF treatment suggests that the cells are compensating for the oxidative stress (FIG. 17d,e) (Robson-Doucette et al., 2011). The increase in ROS production caused by CMPF-treatment was inhibited by co-treatment with the antioxidant N-Acetyl-Cysteine (NAC) (FIG. 17f). Importantly, co-treatment with NAC rescued insulin secretion and insulin content to near control levels in CMPF-treated islets (FIG. 17g,h). Therefore, oxidative stress caused by CMPF metabolism impaired GSIS and insulin processing, and is reversible through reducing ROS generation.

CMPF Impairs Insulin Biosynthesis

Figure 18:
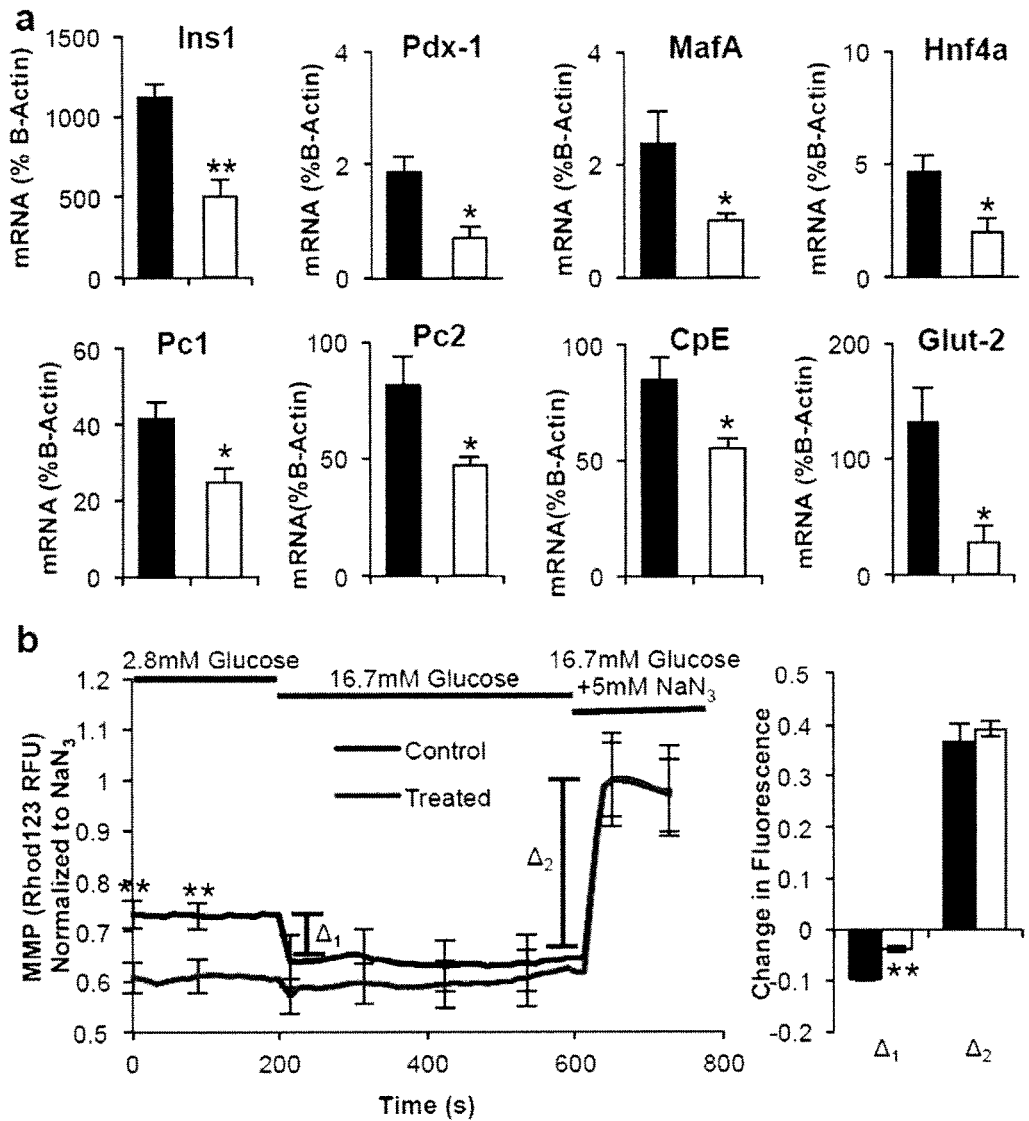
FIG. 18 shows that CMPF causes decreased expression of insulin biosynthesis genes, and altered expression of metabolic genes. A) Expression of insulin, insulin processing enzymes, insulin transcription factors and glucose-sensing genes in 24-hour treated islets (N=5-6/group). B) MMP following 24-hour incubation with control or 200 μM CMPF, and change in fluorescence (N=4/group). C) Classification of significantly changed genes by microarray in 24-hour treated mouse islets based on biological function (N=3, $P<0.05$). Values are mean+/−SEM. Student's t-test (a,c), one-way ANOVA (b). *$P<0.05$, $P<0.01$
Figure 18:
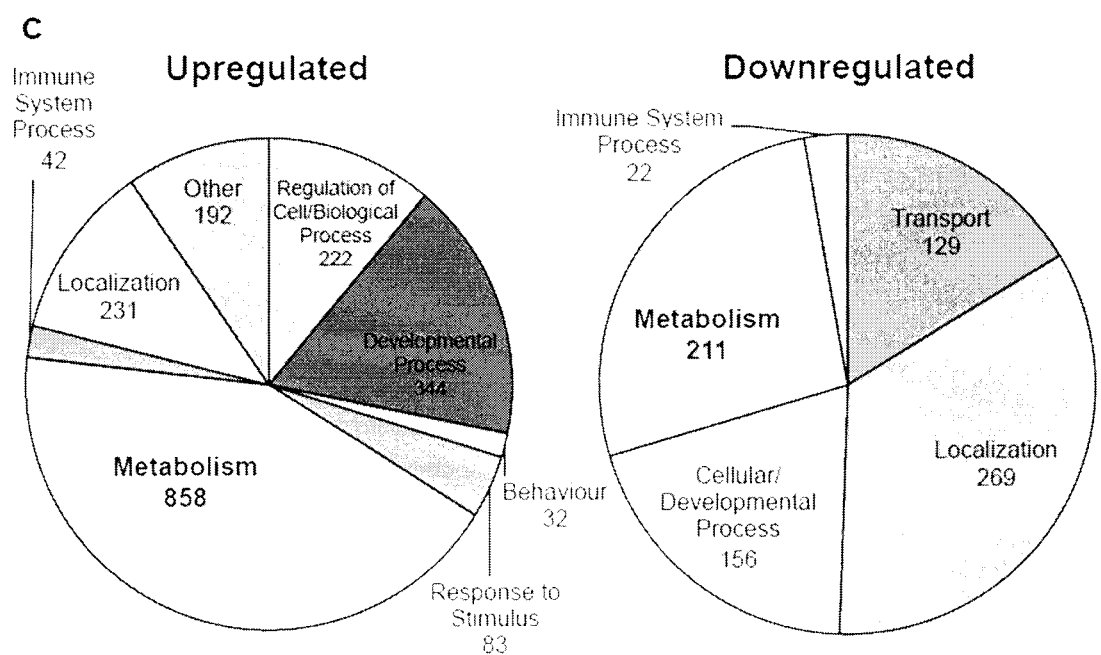

Elevated ROS has been shown to modulate insulin transcription (Poitout and Robertson, 2008; Robertson, 2004) through alterations in AKT and GSK3β activity (Kawamori et al., 2006, Boucher et al., 2006, Kawamori et al., 2003). To determine the mechanism through which CMPF decreases insulin biosynthesis we examined its effect on these key regulators. Under normal conditions, AKT and GSK3β have reciprocal activities. Active pAKT phosphorylates and inactivates GSK3β, preventing phosphorylation of downstream targets (Humphrey et al., 2010). However, under conditions of oxidative stress AKT is inactive (Kawamori et al., 2006). Both AKT and GSK3β phosphorylation were significantly impaired after 24 hr CMPF treatment compared to controls (FIG. 17i,j), indicating decreased AKT and increased GSK3β activity. To determine if these changes had an effect on insulin transcription, the localization of two key insulin transcription factors, PDX1 and FOXO1 were examined using immunofluorescent staining. FOXO1 is normally sequestered in the cytosol due to phosphorylation by AKT (Kitamura et al., 2005). In CMPF-treated islets, FOXO1 is translocated to the nucleus (FIG. 17k,m), reflecting decreased AKT activity (Kawamori et al., 2007). Conversely, PDX1, which is directly phosphorylated by GSK3β (Boucher et al., 2008), is sequestered outside of the nucleus, consistent with increased GSK3β activity (FIG. 17l,n). Absolute levels of these transcription factors were not significantly different, indicating that altered localization is not due to changed protein abundance (FIG. 17o). Translocation of both FOXO1 and PDX1 was prevented by treatment with the antioxidant NAC, indicating that oxidative stress contributes to defective insulin biosynthesis (FIG. 17k-n). Altered activity of these transcription factors is further confirmed by decreased mRNA levels of key target genes including Inst, transcription factors Pdx1 and Mafa, proinsulin processing enzymes CpE, Pc1 and Pc2, and the glucose transporter Glut2 (Boucher et al., 2006; Kaneto et al. 2008) (FIG. 18a).

CMPF Alters Glucose Metabolism

Given that CMPF causes hyperinsulinemia during the fed-state in vivo, and exaggerated secretion of insulin from islets under non-stimulatory conditions in vitro, we rationalized that there must be a defect in glucose-sensing and/or secretion of insulin that could not be solely explained by effects on insulin production. Elevated ROS associated with FFA metabolism has been shown to stimulate insulin secretion under non-stimulatory glucose concentrations (Robson-Doucette et al., 2011; Saddeh et al., 2012; Joseph et al., 2004). Dispersed mouse islets treated for 24 hrs with 200 µM CMPF showed significantly greater hyperpolarization of the MMP under sub-stimulatory glucose concentrations, and significantly reduced MMP hyperpolarization under high glucose conditions when compared to vehicle treated controls, consistent with the elevated ROS (FIG. 17b). These data suggest that CMPF metabolism leads to excessive proton motive force resulting in increased insulin secretion under low glucose conditions and also impairs glucose metabolism and thus GSIS. To confirm changes in mitochondrial function, 24 hr CMPF treated islets were analyzed by microarray. Overall, 6.2% of transcripts were significantly differentially expressed following CMPF treatment. When organized based on biological process, the largest differentially expressed cluster encompassed genes involved in metabolism (38%) (FIG. 17c). Specifically, a significant upregulation of genes related to fat oxidation was observed, which suggests a 'switch' from glucose oxidation-driven metabolism to fat oxidation (Elks et al., 1993). Such a switch can decrease the beta-cell's ability to sense and metabolize glucose, limiting their capacity for GSIS thus may explain CMPF's effect on beta-cells (Hue et al., 2009).

CMPF Enters the Beta-cell through OAT3

Figure 19:
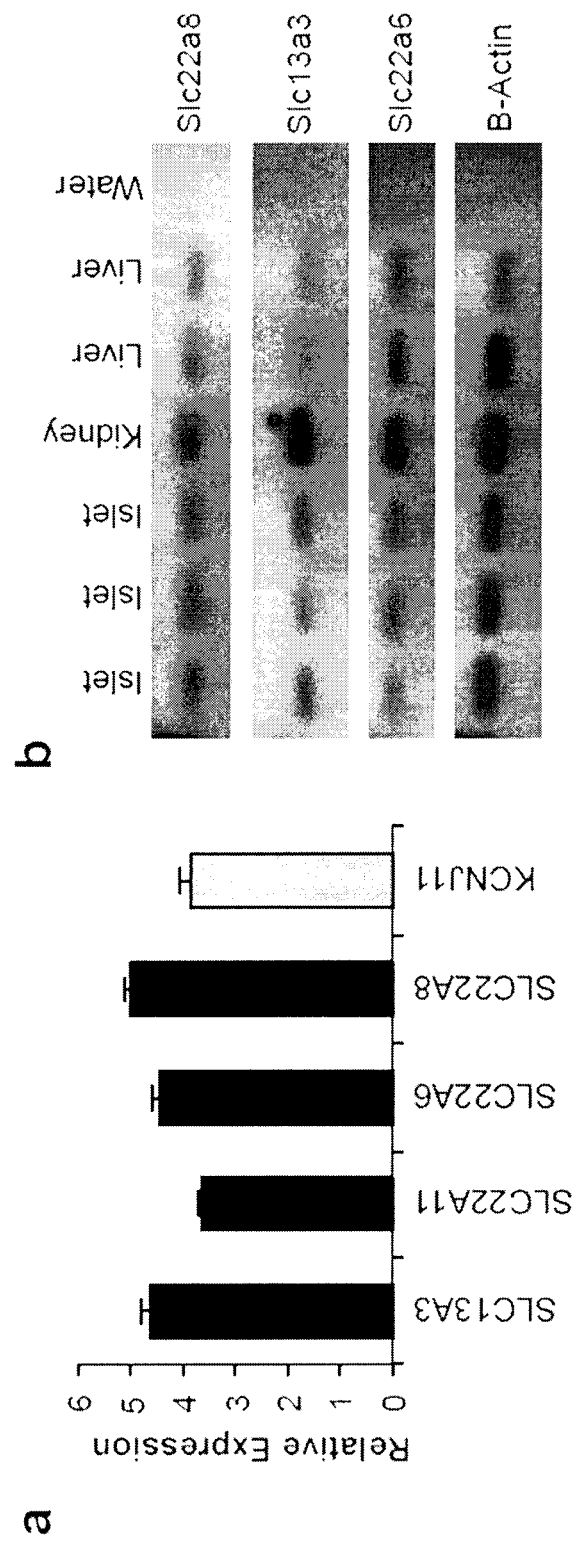
FIG. 19** shows that CMPF enters the beta-cell through Organic Anion Transporter 3. A) Microarray analysis of human islets showing expression of OAT transporters and beta-cell genes (n=3). Validation of OAT expression in human islets by (b) RT-PCR, (c) western blot, and (d) immunofluorescent staining with insulin (n=3-5). Human kidney samples are from the HK2 human proximal tubule cell line. GSIS from murine islets co-treated with OAT inhibitors (e) Probenecid, (f) benzylpenicillin (PCG) and (g) p-aminohippurate (PAH) (n=4/group). h) Total insulin content from murine islets co-treated with CMPF and PCG (n=4). Values mean+/−SEM. Student's t-test (a, e-h). *$P<0.05$, $P<0.01$, *$P<0.001$.
Figure 19:
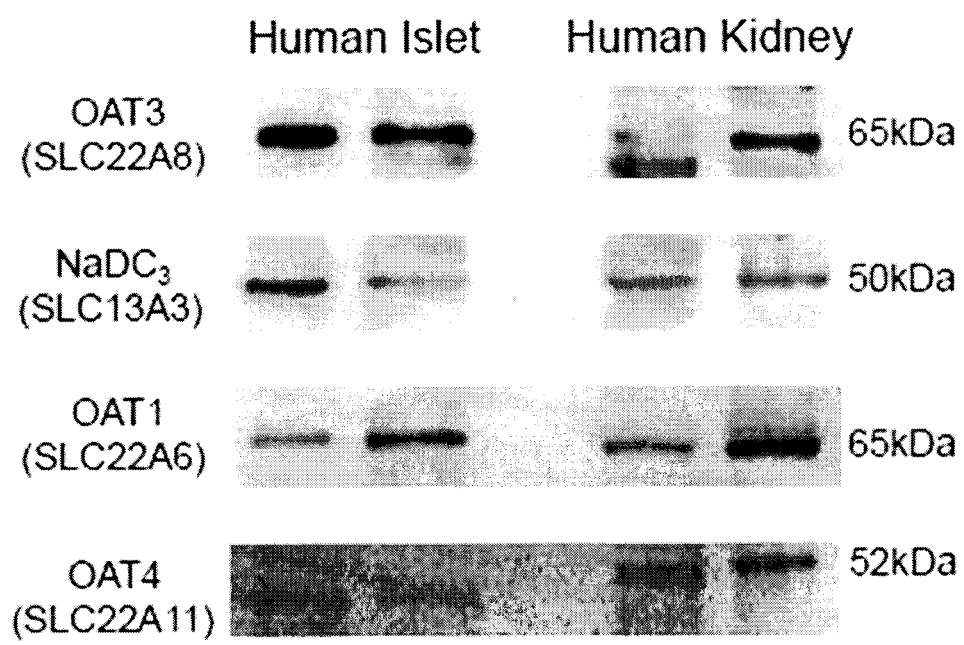
Figure 19:
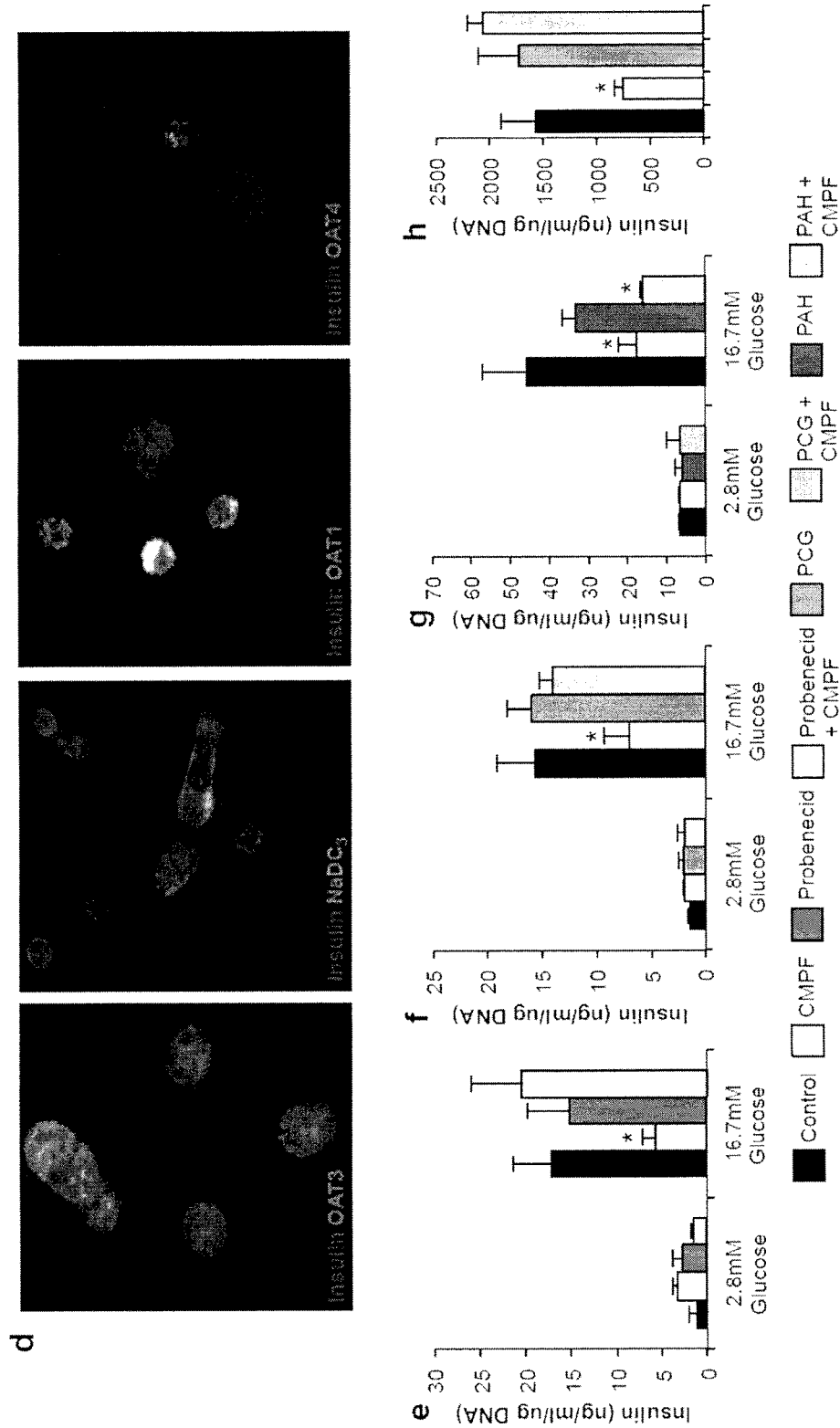
Figure 20:
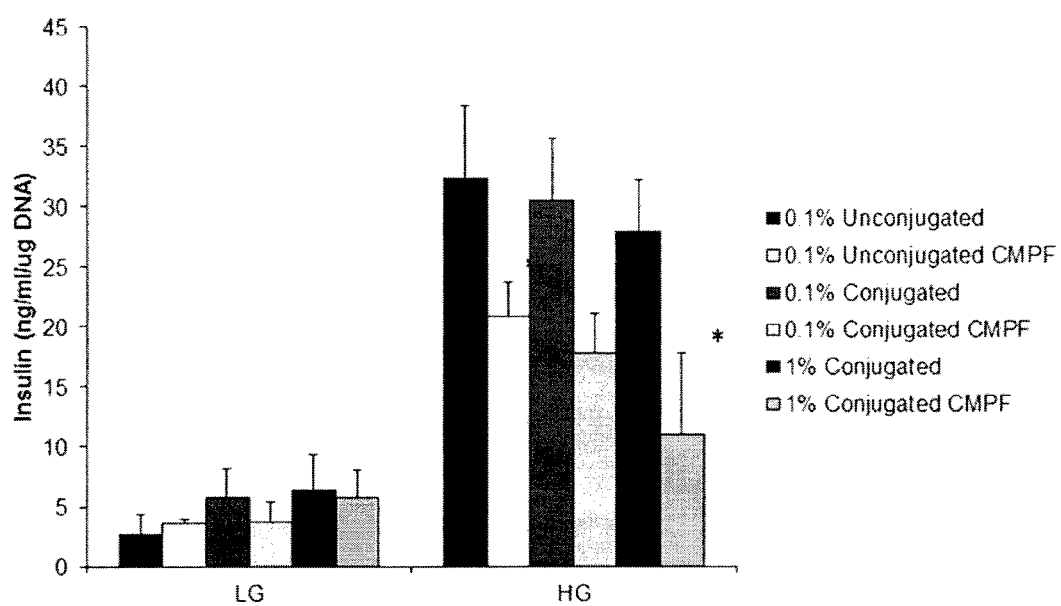
FIG. 20 shows that conjugating CMPF to fatty acid-free BSA has no effect on CMPF-impaired glucose-stimulated insulin secretion. CMPF was conjugated to fatty acid free BSA for 6 hours prior to addition of islets for green and blue bars. The same protocol used for the conjugation of oleate was used. Black and white bars indicate addition of CMPF with 0.1% BSA in the media without pre-conjugation. N=3. *$P<0.05$.

Dibasic urofuran acids, including CMPF, are normally secreted in the urine (Deguchi et al., 2005), and CMPF is known to be elevated in the plasma of uremic patients due to loss of the organic anion transporters (OATs) responsible for their clearance (Sassa et al., 2000). OAT3 (Slc22a8) and OAT1 (Slc22a6) transport CMPF into the kidney proximal tubule cells and require the co-transporter NaDC3 to function (Deguchi et al., 2004). OAT4 (Slc22a11) is the efflux transporter that removes CMPF from the proximal tubule into the kidney lumen in humans (Deguchi et al., 2005). We therefore investigated whether CMPF also enters the beta-cell through these transporters. Microarray analysis of human islets shows expression of all four transcripts at levels comparable to that of the beta-cell KATP channel Kcnj11 (FIG. 19a). This was further validated by RT-PCR, with bands corresponding to each of the transporters, as well as by immunoblotting (FIG. 19b,c). To determine protein localization, we performed immunofluorescent staining in dispersed human islet cells (FIG. 19d). OAT3 and NaDC3 show strong staining in insulin positive beta-cells. OAT1 and OAT4 are predominantly expressed in insulin-negative cells. Costaining with glucagon revealed that OAT4 is also not expressed in glucagon-positive cells. Therefore, the OAT transporters are expressed in the islet, with OAT3 and NaDC3 being strongly expressed in insulin-positive cells.

To determine if OATs are responsible for CMPF transport into beta-cells, we utilized inhibitors of OAT function. Probenecid is a non-specific OAT-blocker (Miyamoto et al., 2012). Treatment of islets with 1 mM probenecid for 24 hrs rescued insulin secretion from CMPF-treated islets to control levels (FIG. 19e). To determine which OAT is primarily responsible for CMPF transport into beta-cells, we treated islets with 300 µM of benzylpenicillin (PCG), an OAT3-specific inhibitor, or 50 µM of paminohippurate (PAH), an OAT1-specific inhibitor (Deguchi et al., 2005). Consistent with previous reports that OAT3 is the dominant CMPF transporter (Deguchi et al., 2005), PCG was able to rescue insulin secretion and insulin content from CMPF-treated islets to control levels (FIG. 19f,h). However, treatment with PAH had no effect on secretion (FIG. 19g). Therefore, CMPF is transported into the beta-cell through OAT3, and blockage of this transporter prevents CMPF from impairing GSIS and insulin biosynthesis.

Discussion

The underlying cause of both GDM and T2D is a failure of the beta-cell to respond to changing metabolic demands; namely increased insulin resistance (Buchanan, 2001; Kahn 2003; Prenki and Nolan, 2006). Here we demonstrate that the furan fatty acid metabolite CMPF impairs pancreatic beta-cell function at concentrations observed in patients with GDM, T2D, and impaired glucose tolerance during the transition from GDM to T2D, consistent with a progressive decline in beta-cell function during this period (Retnakaran et al., 2010). Treatment with CMPF recapitulates many key characteristics of diabetes, including basal hyperinsulinemia (Wijendran et al., 1999) with impaired GSIS and reduced whole-body glucose utilization (Kuhl, 1991; Bowes, 1996). In vitro, we demonstrate that CMPF metabolism causes beta-cell dysfunction through impairment of mitochondrial function and glucose metabolism, as well as inducing oxidative stress. Elevated ROS levels altered the activity of key kinases AKT and GSK3β, changing transcriptional activity, and ultimately reducing insulin transcription and post-translational processing. Therefore elevated plasma CMPF may play an important causal role in beta-cell dysfunction associated with GDM, T2D and the progression from GDM to T2D.

The effect of CMPF can be rescued by two distinct approaches: blocking CMPF entry into the beta-cell, and reducing ROS accumulation. Here we show for the first time that CMPF enters the beta-cell through the OAT3 transporter, which has previously only been functionally characterized on the basolateral membrane of kidney proximal tubules cells (Deguchi et al., 2005), with low levels of expression reported in the liver and brain (Sweet et al., 2002; Deguchi et al., 2006). We show that CMPF transport can be blocked using the commonly prescribed drugs probenecid and benzylpenicillin, which non-specifically and specifically inhibit OAT3 transport respectively. Interestingly, we show that while human beta-cells express influx transporter OAT3, the efflux transporter OAT4 is absent. Thus during diabetes when plasma CMPF is elevated, potentially due to altered OAT activity in the kidney, it can presumably enter the beta-cell but not exit, promoting its metabolism and associated effects. Therefore, preventing CMPF influx through blockage of the OAT transporters, or increasing CMPF efflux from the beta-cell is are attractive avenues for future research into the prevention of beta-cell failure.

Once inside the beta-cell, CMPF is metabolized, causing impaired glucose utilization and increased ROS production. Low-level ROS production potentiates GSIS, aiding the beta-cell in responding to acute increases in nutrients including FFAs (Robson-Doucette et al., 2011; Saadeh et al., 2012; Poitout and Robertson, 2008). However, longer-term, the beta-cell is particularly vulnerable to oxidative stress due to relatively low expression of antioxidant enzymes relative to other tissue types (Robson-Doucette et al., 2011; Robertson, 2004). Treatment with anti-oxidants has been proposed as a promising approach for the treatment of T2D, and has been shown to attenuate islet fibrosis and apoptosis and improve glucose tolerance and insulin sensitivity in rodent models (Lee et al., 2011). Our finding that pre-treatment with the antioxidant NAC prevents CMPF from inducing beta-cell failure suggests that antioxidant treatment may also be used in the prevention and/or treatment of GDM.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Arkhammar P., et al. Glucose-stimulated efflux of FURA-2 in pancreatic beta-cells is prevented by probenecid. *Biochemical and Biophysical Research Communications*. 1989. 159(1): p. 223-228.

Basford, C. L., et al., *The functional and molecular characterisation of human embryonic stem cell-derived insulin-positive cells compared with adult pancreatic beta cells*. Diabetologia, 2012. 55(2): p. 358-71

Baudoux T. E. R., et al. Probenecid prevents acute tubular necrosis in a mouse model of aristolochic acid nephropathy. *Kidney International*. 2012. 82(10).

Boucher, M. J., et al., *Phosphorylation marks IPF1/PDX1 protein for degradation by glycogen synthase kinase 3-dependent mechanisms*. J Biol Chem, 2006. 281(10): p. 6395-403.

Bowes, S. B., et al., *Measurement of glucose metabolism and insulin secretion during normal pregnancy and pregnancy complicated by gestational diabetes*. Diabetologia, 1996. 39(8): p. 976-83.

Buchanan, T. A., *Pancreatic B-cell defects in gestational diabetes: implications for the pathogenesis and prevention of type 2 diabetes*. J Clin Endocrinol Metab, 2001. 86(3): p. 989-93.

Butler, D., Wartime tactic doubles power of scarce bird-flu drug. Nature, 2005. 438(7064): p. 6.

Costigan, M. G. and W. E. Lindup, Plasma clearance in the rat of a furan dicarboxylic acid which accumulates in uremia. Kidney Int, 1996. 49(3): p. 634-8.

Deguchi, T., et al., *Characterization of uremic toxin transport by organic anion transporters in the kidney*. Kidney Int, 2004. 65(1): p. 162-74.

Deguchi T., et al., Renal clearance of endogenous hippurate correlates with expression levels of renal organic anion transporters in uremic rats. J Pharmacol Exp Ther, 2005. 314(2): p. 932-8.

Deguchi, T., et al., Differential contributions of rOat1 (Slc22a6) and rOat3 (Slc22a8) to the in vivo renal uptake of uremic toxins in rats. Pharm Res, 2005. 22(4): p. 619-27.

Deguchi, T., et al., *Involvement of organic anion transporters in the efflux of uremic toxins across the blood-brain barrier*. J Neurochem, 2006. 96(4): p. 1051-9.

Diao, J., et al., *UCP2 is highly expressed in pancreatic alpha-cells and influences secretion and survival*. Proc Natl Acad Sci USA, 2008. 105(33): p. 12057-62.

Dominguez V., et al., Class II phosphoinositide 3-kinase regulates exocytosis of insulin granules in pancreatic beta cells. J Biol Chem, 2011. 286(6): p. 4216-25.

Elks, M. L., *Chronic perifusion of rat islets with palmitate suppresses glucose-stimulated insulin release*. Endocrinology, 1993. 133(1): p. 208-14.

Everts et al. Effects of a furan fatty acid and indoxyl sulfate on thyroid hormone uptake in cultured anterior pituitary cells. The American Physiological Society (1995).

Hue, L. and H. Taegtmeyer, *The Randle cycle revisited: a new head for an old hat*. Am J Physiol Endocrinol Metab, 2009. 297(3): p. E578-91.

Humphrey, R. K., et al., *Glucose regulates steady-state levels of PDX1 via the reciprocal actions of GSK3 and AKT kinases*. J Biol Chem, 2010. 285(5): p. 3406-16.

Joseph, J. W., et al., *Free fatty acid-induced beta-cell defects are dependent on uncoupling protein 2 expression*. J Biol Chem, 2004. 279(49): p. 51049-56.

Kahn, S. E., *The relative contributions of insulin resistance and beta-cell dysfunction to the pathophysiology of Type 2 diabetes*. Diabetologia, 2003. 46(1): p. 3-19.

Kamoda, T., et al., *The serum levels of proinsulin and their relationship with IGFBP-1 in obese children*. Diabetes Obes Metab, 2006. 8(2): p. 192-6.

Kaneto, H., et al., *PDX-1 and MafA play a crucial role in pancreatic beta-cell differentiation and maintenance of mature beta-cell function*. Endocr J, 2008. 55(2): p. 235-52.

Kashemsant, N. and C. B. Chan, *Impact of uncoupling protein-2 overexpression on proinsulin processing*. J Mol Endocrinol, 2006. 37(3): p. 517-26.

Kawamori, D., et al., *Oxidative stress induces nucleocytoplasmic translocation of pancreatic transcription factor PDX-1 through activation of c-Jun NH(2)-terminal kinase*. Diabetes, 2003. 52(12): p. 2896-904.

Kawamori, D., et al., *The forkhead transcription factor Foxo1 bridges the JNK pathway and the transcription factor PDX-1 through its intracellular translocation*. J Biol Chem, 2006. 281(2): p. 1091-8.

Kitamura, Y. I., et al., *FoxO1 protects against pancreatic beta cell failure through NeuroD and MafA induction*. Cell Metab, 2005. 2(3): p. 153-63.

Kuhl, C., *Insulin secretion and insulin resistance in pregnancy and GDM. Implications for diagnosis and management*. Diabetes, 1991. 40 Suppl 2: p. 18-24.

Kutlu B., et al., Detailed transcriptome atlas of the pancreatic beta cell. BMC Med Genomics, 2009. 2: p. 3.

Lee, S. C., C. A. Robson-Doucette, and M. B. Wheeler, *Uncoupling protein 2 regulates reactive oxygen species formation in islets and influences susceptibility to diabetogenic action of streptozotocin*. J Endocrinol, 2009. 203(1): p. 33-43.

Lee, E., et al., *Antioxidant treatment may protect pancreatic beta cells through the attenuation of islet fibrosis in an animal model of type 2 diabetes*. Biochem Biophys Res Commun, 2011. 414(2): p. 397-402.

Lim C F, Stockigt J R, Curtis A J, Wynne K N, Barlow J W, and Topliss D J. A naturally occurring furan fatty acid enhances drug inhibition of thyroxine binding in serum. Metabolism (1993). 42(11); 1468-74.

Liu, Y., et al., *Adiponectin Corrects High-Fat Diet-Induced Disturbances in Muscle Metabolomic Profile and Whole-Body Glucose Homeostasis*. Diabetes, 2012.

Mabuchi H, and Nakahashi H. A major endogenous ligand substance involved in renal failure. Nephron (1988). 49(4); 277-80.

Mason, R. M., Studies on the effect of probenecid (benemid) in gout. Ann Rheum Dis, 1954. 13(2): p. 120-30.

Mishra R., et al., Adipose differentiation—related protein and regulators of lipid homeostasis identified by gene expression profiling in the murine db/db diabetic kidney. Am J Physiol Renal Physiol, 2004. 286(5): p. F913-21.

Miyamoto, Y., et al., *A uremic toxin, 3-carboxy-4-methyl-5-propyl-2-furanpropionate induces cell damage to proximal tubular cells via the generation of a radical intermediate*. Biochem Pharmacol, 2012. 84(9): p. 1207-14.

More V. R., et al., Severe diabetes and leptin resistance cause differential hepatic and renal transporter expression in mice. Comp Hepatol, 2012. 11(1): p. 1.

Poitout, V. and R. P. Robertson, *Glucolipotoxicity: fuel excess and beta-cell dysfunction*. Endocr Rev, 2008. 29(3): p. 351-66.

Niwa T, Aiuchi T, Nakaya K, Emoto Y, Miyazaki T, and Maeda K. Inhibition of mitochondrial respiration by furancarboxylic acid accululated in uremic serum in its albumin-bound and non-diabyzable form. Clin Nephrol (1993). 39(2); 92-96.

Prentki, M. and C. J. Nolan, *Islet beta cell failure in type 2 diabetes*. J Clin Invest, 2006. 116(7): p. 1802-12.

Retnakaran, R., et al., *Beta-cell function declines within the first year postpartum in women with recent glucose intolerance in pregnancy*. Diabetes Care, 2010. 33(8): p. 1798-804.

Robertson, R. P., *Chronic oxidative stress as a central mechanism for glucose toxicity in pancreatic islet beta cells in diabetes*. J Biol Chem, 2004. 279(41): p. 42351-4.

Robson-Doucette, C. A., et al., *Beta-cell uncoupling protein 2 regulates reactive oxygen species production, which influences both insulin and glucagon secretion*. Diabetes, 2011. 60(11): p. 2710-9.

Saadeh, M., et al., *Reactive oxygen species stimulate insulin secretion in rat pancreatic islets: studies using mono-oleoyl-glycerol*. PLoS One, 2012. 7(1): p. e30200.

Sassa T, Matsuno H, Niwa M, Kazawa O, Takeda N, Niwa T, Kumada T, and Uematsu T. Measurement of furancarboxylic acid, a candidate for uremic toxin, in human serum, hair, and sweat, and analysis of pharmacological actions in vitro. Arch Toxicol (2000)

Sato M, Koyama M, Miyazaki T, and Niwa T. Reduced renal clearance of furancarboxylic acid, a major albumin-bound organic acid, in undialyzed uremic patients. Nephron (1996). 74(2); 419-21.

Sekine, T., H. Miyazaki, and H. Endou, Molecular physiology of renal organic anion transporters. Am J Physiol Renal Physiol, 2006. 290(2): p. F251-61.

Sweet, D. H., et al., *Impaired organic anion transport in kidney and choroid plexus of organic anion transporter 3 (Oat3 (Slc22a8)) knockout mice*. J Biol Chem, 2002. 277 (30): p. 26934-43.

Tsutsumi Y, Maruyama T, Takadate A, Goto M, Matsunaga H, and Otagiri M. Interaction between two dicarboxylate endogenous substances, bilirubin and an uremic toxin, 3-carboxy-4-methyl-5-propyl-2-furanpropanoic acid, on human serum albumin. Pharmaceutical Research (1999). 16(6); 916.

Wijendran, V., et al., *Maternal plasma phospholipid polyunsaturated fatty acids in pregnancy with and without gestational diabetes mellitus: relations with maternal factors*. Am J Clin Nutr, 1999. 70(1): p. 53-61.

The invention claimed is:

1. A method of treating impaired glucose homeostasis comprising:
    (a) detecting a test level of 3-carboxy-4-methyl-5-propyl-2-furanpropanoic acid (CMPF) in a sample from a subject; and
    (b) comparing the test level of CMPF to a control level wherein:
        i) the control level is representative of a level of CMPF in subjects without impaired glucose homeostasis and a subject having an increase in the level of CMPF relative to the control level is identified as having, or at risk of developing, impaired glucose homeostasis; or
        ii) the control level is representative of a level of CMPF in subjects with impaired glucose homeostasis and a subject having a similarity in the level of CMPF relative to the control level is identified as having, or at risk of developing impaired glucose homeostasis; and
    (c) administering to the subject identified as having, or at risk of developing, impaired glucose homeostasis in part b) an agent suitable for the treatment of impaired glucose homeostasis selected from the group consisting of a CMPF inhibitor, insulin, metformin, GLP-1 receptor agonist, GLP-1 analog, sulfonylureas, or insulin sensitizer.

2. The method of claim 1, wherein the impaired glucose homeostasis is gestational diabetes mellitus, type 2 diabetes, impaired glucose tolerance, pre-diabetes, or insulin resistance.

3. The method of claim 2, wherein the control level is:
    i) representative of a level of CMPF in subjects without gestational diabetes mellitus, type 2 diabetes, impaired glucose tolerance, pre-diabetes, or insulin resistance and an increased test level of CMPF relative to the control is indicative of the subject having, or at risk of developing gestational diabetes mellitus, type 2 diabetes, impaired glucose tolerance pre-diabetes, or insulin resistance; or
    ii) representative of a level of CMPF in subjects with gestational diabetes mellitus, type 2 diabetes, impaired glucose tolerance, pre-diabetes, or insulin resistance and a similar or greater test level of CMPF relative to the control is indicative of the subject having, or at risk of developing gestational diabetes mellitus, type 2 diabetes, impaired glucose tolerance, pre-diabetes, or insulin resistance.

4. The method of claim 1, wherein the control level is representative of a level of CMPF in subjects with normal glucose tolerance.

5. The method of claim 1, wherein the control level is a pre-determined standardized control level.

6. The method of claim 1, wherein the control level is a level of CMPF in plasma greater than 50 µM.

7. The method of claim 1, wherein detecting CMPF in the sample comprises using mass spectrometry (MS), gas chromatography/mass spectrometry (GC-MS) or liquid chromatography mass spectrometry (LC-MS).

8. The method of claim 1, wherein detecting CMPF in the sample comprises using High Performance Liquid Chromatography (HPLC) or Nuclear Magnetic Resonance (NMR) spectroscopy.

9. The method of claim 1, wherein detecting CMPF in the sample comprises using antibodies that specifically bind CMPF.

10. The method of claim 9, wherein detecting CMPF in the sample comprises using an Enzyme-Linked Immunosorbent Assay (ELISA).

11. The method of claim 1, wherein the sample is a blood sample.

12. The method of claim 1, wherein the sample is sweat or urine.

13. The method of claim 1, wherein the subject is human.

14. The method of claim 1 wherein the control level is a level of CMPF from the subject at an earlier time point, and an increase in the level of CMPF is indicative of more severe impaired glucose homeostasis in the subject or a decrease in the level of CMPF is indicative of improved glucose homeostasis in the subject.

* * * * *